US011883386B2

(12) United States Patent
Kawamoto et al.

(10) Patent No.: US 11,883,386 B2
(45) Date of Patent: Jan. 30, 2024

(54) PROLYL HYDROXYLASE INHIBITORS AND METHODS OF USE

(71) Applicant: Akebia Therapeutics, Inc., Cambridge, MA (US)

(72) Inventors: Richard Masaru Kawamoto, Divide, CO (US); Shengde Wu, West Chester, OH (US); Artem G. Evdokimov, Foristell, MO (US); Kenneth D Greis, Fort Thomas, KY (US); Angelique Sun Boyer, West Chester, OH (US); Namal C. Warshakoon, Cary, NC (US)

(73) Assignee: Akebia Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/815,391

(22) Filed: Jul. 27, 2022

(65) Prior Publication Data
US 2023/0201178 A1    Jun. 29, 2023

Related U.S. Application Data

(60) Continuation of application No. 16/908,092, filed on Jun. 22, 2020, now Pat. No. 11,426,393, which is a continuation of application No. 16/119,146, filed on Aug. 31, 2018, now Pat. No. 10,729,681, which is a continuation of application No. 15/420,617, filed on Jan. 31, 2017, now abandoned, which is a continuation of application No. 14/854,080, filed on Sep. 15, 2015, now Pat. No. 9,598,370, which is a continuation of application No. 14/568,200, filed on Dec. 12, 2014, now abandoned, which is a continuation of application No. 14/062,011, filed on Oct. 24, 2013, now Pat. No. 8,940,773, which is a division of application No. 13/681,876, filed on Nov. 20, 2012, now Pat. No. 8,598,210, which is a continuation of application No. 12/860,073, filed on Aug. 20, 2010, now Pat. No. 8,343,952, which is a continuation of application No. 11/821,936, filed on Jun. 26, 2007, now Pat. No. 7,811,595.

(60) Provisional application No. 60/816,522, filed on Jun. 26, 2006.

(51) Int. Cl.
| | | |
|---|---|---|
| C07D 213/81 | (2006.01) |
| C07D 213/65 | (2006.01) |
| A61K 31/4418 | (2006.01) |
| C07C 235/60 | (2006.01) |
| C07C 237/42 | (2006.01) |
| C07C 255/57 | (2006.01) |
| C07D 405/10 | (2006.01) |
| C07D 405/04 | (2006.01) |
| C07D 295/192 | (2006.01) |
| C07D 401/04 | (2006.01) |
| C07D 401/10 | (2006.01) |
| C07D 417/04 | (2006.01) |
| A61K 31/4433 | (2006.01) |

(52) U.S. Cl.
CPC ...... *A61K 31/4418* (2013.01); *A61K 31/4433* (2013.01); *C07C 235/60* (2013.01); *C07C 237/42* (2013.01); *C07C 255/57* (2013.01); *C07D 213/65* (2013.01); *C07D 213/81* (2013.01); *C07D 295/192* (2013.01); *C07D 401/04* (2013.01); *C07D 401/10* (2013.01); *C07D 405/04* (2013.01); *C07D 405/10* (2013.01); *C07D 417/04* (2013.01); *Y02A 50/30* (2018.01)

(58) Field of Classification Search
CPC .......................... C07D 213/65; C07D 213/81
See application file for complete search history.

(56) References Cited

U.S. PATENT DOCUMENTS

| | | | |
|---|---|---|---|
| 3,894,920 A | 7/1975 | Kondo et al. |
| 4,016,287 A | 4/1977 | Ebhardt et al. |
| 4,044,049 A | 8/1977 | Ruyle et al. |
| 5,397,799 A | 3/1995 | Kress et al. |
| 5,405,613 A | 4/1995 | Rowland et al. |
| 5,607,954 A | 3/1997 | Weidmann et al. |
| 5,610,172 A | 3/1997 | Weidmann et al. |
| 5,620,995 A | 4/1997 | Weidmann et al. |
| 5,620,996 A | 4/1997 | Weidmann et al. |
| 5,643,957 A | 7/1997 | Leone-Bay et al. |
| 5,658,933 A | 8/1997 | Weidmann et al. |
| 5,719,164 A | 2/1998 | Weidmann et al. |
| 5,726,305 A | 3/1998 | Weidmann et al. |
| 6,020,350 A | 2/2000 | Wiedmann et al. |

(Continued)

FOREIGN PATENT DOCUMENTS

| | | |
|---|---|---|
| CA | 2098158 A1 | 12/1993 |
| CA | 2253282 A1 | 11/1997 |

(Continued)

OTHER PUBLICATIONS

Alesso et al., Improving resins for solid phase synthesis: incorporation of I-[2-(2-methoxyethoxy) ethoxy]4-vinyl-benzene, Tetrahedron, vol. 59, 7163-7169, 2003.

(Continued)

*Primary Examiner* — Daniel R Carcanague
(74) *Attorney, Agent, or Firm* — Proskauer Rose LLP

(57) ABSTRACT

The present disclosure relates to HIF-1α prolyl hydroxylase inhibitors, compositions which comprise the HIF-1α prolyl hydroxylase inhibitors described herein and to methods for controlling, inter alia, Peripheral Vascular Disease (PVD), Coronary Artery Disease (CAD), heart failure, ischemia, and anemia.

5 Claims, 2 Drawing Sheets
Specification includes a Sequence Listing.

(56) References Cited

U.S. PATENT DOCUMENTS

| | | | |
|---|---|---|---|
| 6,093,730 A | 7/2000 | Weidmann et al. |
| 6,323,227 B1 | 11/2001 | Klein et al. |
| 6,420,427 B1 | 7/2002 | Takahashi et al. |
| 6,566,088 B1 | 5/2003 | McKnight et al. |
| 6,589,758 B1 | 7/2003 | Zhu et al. |
| 6,855,510 B2 | 2/2005 | Kaelin et al. |
| 7,183,287 B2 | 2/2007 | Durley et al. |
| 7,323,475 B2 | 1/2008 | Arend et al. |
| 7,402,696 B2 | 7/2008 | Suzuki et al. |
| 7,588,824 B2 | 9/2009 | Wudl et al. |
| 7,588,924 B2 | 9/2009 | Evdokimov et al. |
| 7,618,940 B2 | 11/2009 | Fourney et al. |
| 7,811,595 B2 | 10/2010 | Kawamoto et al. |
| 7,897,612 B2 | 3/2011 | Fitch et al. |
| 8,050,873 B2 | 11/2011 | Evdokimov et al. |
| 8,124,582 B2 | 2/2012 | Guenzler-Pukall et al. |
| 8,323,671 B2 | 12/2012 | Wu et al. |
| 8,343,952 B2 | 1/2013 | Kawamoto et al. |
| 8,512,972 B2 | 8/2013 | Evdokimov et al. |
| 8,530,404 B2 | 9/2013 | Seeley et al. |
| 8,598,210 B2 | 12/2013 | Kawamoto et al. |
| 8,722,895 B2 | 5/2014 | Kawamoto et al. |
| 8,865,748 B2 | 12/2014 | Shalwitz et al. |
| 8,940,773 B2 | 1/2015 | Kawamoto et al. |
| 9,145,366 B2 | 9/2015 | Lanthier et al. |
| 9,598,370 B2 | 3/2017 | Kawamoto et al. |
| 9,701,636 B2 | 7/2017 | Copp et al. |
| 9,776,969 B2 | 10/2017 | Lanthier et al. |
| 9,987,262 B2 | 6/2018 | Copp et al. |
| 10,149,842 B2 | 12/2018 | Copp et al. |
| 10,150,734 B2 | 12/2018 | Hanselmann et al. |
| 10,246,416 B2 | 4/2019 | Lanthier et al. |
| 10,596,158 B2 | 3/2020 | Copp et al. |
| 10,729,681 B2 | 8/2020 | Kawamoto et al. |
| 10,738,010 B2 | 8/2020 | Lanthier et al. |
| 11,065,237 B2 | 7/2021 | Copp et al. |
| 11,267,785 B2 | 3/2022 | Lanthier et al. |
| 11,426,393 B2* | 8/2022 | Kawamoto ............ A61P 1/04 |
| 2003/0153503 A1 | 8/2003 | Klaus et al. |
| 2003/0176317 A1 | 9/2003 | Guenzler-Pukall et al. |
| 2004/0146964 A1 | 7/2004 | Maxwell et al. |
| 2004/0254215 A1 | 12/2004 | Arend et al. |
| 2006/0276477 A1 | 12/2006 | Klaus et al. |
| 2007/0154482 A1 | 7/2007 | Sukhatme et al. |
| 2007/0213335 A1 | 9/2007 | Fitch et al. |
| 2008/0213404 A1 | 9/2008 | Johnson et al. |
| 2010/0331303 A1 | 12/2010 | Kawamoto et al. |
| 2010/0331374 A1 | 12/2010 | Wu et al. |
| 2012/0316204 A1 | 12/2012 | Shalwitz et al. |
| 2012/0329836 A1 | 12/2012 | Marsh et al. |
| 2013/0203816 A1 | 8/2013 | Kawamoto et al. |
| 2013/0245076 A1 | 9/2013 | Kawamoto et al. |
| 2014/0045899 A1 | 2/2014 | Kawamoto et al. |
| 2014/0057892 A1 | 2/2014 | Kawamoto et al. |
| 2015/0119425 A1 | 4/2015 | Kawamoto et al. |
| 2016/0009648 A1 | 1/2016 | Kawamoto et al. |
| 2016/0143891 A1 | 5/2016 | Shalwitz et al. |
| 2016/0339005 A1 | 11/2016 | Shalwitz et al. |
| 2017/0189387 A1 | 7/2017 | Kawamoto et al. |
| 2017/0258773 A1 | 9/2017 | Copp et al. |
| 2018/0065933 A1 | 3/2018 | Hanselmann et al. |
| 2018/0092892 A1 | 4/2018 | Smith et al. |
| 2019/0375713 A1 | 12/2019 | Lanthier et al. |
| 2020/0345711 A1 | 11/2020 | Copp et al. |
| 2021/0070709 A1 | 3/2021 | Gorin et al. |
| 2021/0122715 A1 | 4/2021 | Lanthier et al. |
| 2021/0206721 A1 | 7/2021 | Ranjan et al. |
| 2022/0040159 A1 | 2/2022 | Copp et al. |

FOREIGN PATENT DOCUMENTS

| | | |
|---|---|---|
| CN | 111320577 A | 6/2020 |
| EP | 0650960 A1 | 5/1995 |
| EP | 0650961 A1 | 5/1995 |
| EP | 0650960 B1 | 3/1997 |
| EP | 0650961 B1 | 3/1997 |
| EP | 2044005 B1 | 10/2010 |
| JP | H09221476 A | 8/1997 |
| JP | 2001-048786 A | 2/2001 |
| JP | 2006-316054 A | 11/2006 |
| WO | WO 1997/041103 A1 | 11/1997 |
| WO | WO 1997/044333 A1 | 11/1997 |
| WO | WO 1999/000356 A1 | 1/1999 |
| WO | WO 1999/048870 A1 | 9/1999 |
| WO | WO 2000/074725 A1 | 12/2000 |
| WO | WO 2002/074980 A2 | 9/2002 |
| WO | WO 2002/074981 A2 | 9/2002 |
| WO | WO 2002/083688 A1 | 10/2002 |
| WO | WO 2003/028663 A2 | 4/2003 |
| WO | WO 2003/032972 A1 | 4/2003 |
| WO | WO 2003/049686 A2 | 6/2003 |
| WO | WO 2003/053997 A2 | 7/2003 |
| WO | WO 2003/057820 A2 | 7/2003 |
| WO | WO 2004/035812 A2 | 4/2004 |
| WO | WO 2004/048383 A1 | 6/2004 |
| WO | WO 2004/108121 A1 | 12/2004 |
| WO | WO 2005/007192 A2 | 1/2005 |
| WO | WO 2005/115984 A2 | 12/2005 |
| WO | WO 2005/118836 A2 | 12/2005 |
| WO | WO 2006/019831 A1 | 2/2006 |
| WO | WO 2006/030977 A2 | 3/2006 |
| WO | WO 2006/114213 A1 | 11/2006 |
| WO | WO 2007/038571 A2 | 4/2007 |
| WO | WO 2007/047194 A2 | 4/2007 |
| WO | WO 2007/070359 A2 | 6/2007 |
| WO | WO 2007/082899 A1 | 7/2007 |
| WO | WO 2007/084667 A2 | 7/2007 |
| WO | WO 2007/088571 A2 | 8/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/002576 A2 | 1/2008 |
| WO | WO 2008/089051 A1 | 7/2008 |
| WO | WO 2008/089052 A2 | 7/2008 |
| WO | WO 2008/130508 A1 | 10/2008 |
| WO | WO 2008/130527 A1 | 10/2008 |
| WO | WO 2008/137060 A1 | 11/2008 |
| WO | WO 2008/144266 A1 | 11/2008 |
| WO | WO 2009/019656 A1 | 2/2009 |
| WO | WO 2009/037570 A2 | 3/2009 |
| WO | WO 2009/039321 A1 | 3/2009 |
| WO | WO 2009/039323 A1 | 3/2009 |
| WO | WO 2009/043093 A1 | 4/2009 |
| WO | WO 2009/049112 A1 | 4/2009 |
| WO | WO 2009/067790 A1 | 6/2009 |
| WO | WO 2009/070644 A1 | 6/2009 |
| WO | WO 2009/073497 A2 | 6/2009 |
| WO | WO 2009/073669 A1 | 6/2009 |
| WO | WO 2009/086044 A1 | 7/2009 |
| WO | WO 2009/086592 A1 | 7/2009 |
| WO | WO 2009/089547 A1 | 7/2009 |
| WO | WO 2012/170377 A1 | 12/2012 |
| WO | WO 2014/200773 A2 | 12/2014 |
| WO | WO 2015/073779 A1 | 5/2015 |
| WO | WO 2016/153996 A1 | 9/2016 |
| WO | WO 2016/161094 A1 | 10/2016 |
| WO | WO 2019/028150 A1 | 2/2019 |
| WO | WO 2019/217550 A1 | 11/2019 |
| WO | WO 2022/006427 A1 | 1/2022 |

OTHER PUBLICATIONS

Altschul et al., Gapped BLAST and PSI-BLAST: A New Generation of Protein Database Search Programs, Nucleic Acids Res., vol. 25, No. 27, 3389-3402, 1997.

Anderson et al., Antileukemic Activity of Derivatives of I,2-Dimethyl-3,4-bis(hydroxymethyl)-5-phenylpyrrole Bis(N-methylcarbamate), J. Med. Chem.: vol. 22, No. 8, 977-980, 1979.

Annex et al., Growth Factor-Induced Therapeutic Angiogenesis in the Heart: Protein Therapy, Cardiovascular Research, vol. 65, No. 3, 649-655, 2005.

(56) References Cited

OTHER PUBLICATIONS

Ardelt et al., Estradiol Regulates Angiopoietin-1 mRNA Expression Through Estrogen Receptor-a in a Rodent Experimental Stroke Model, Stroke, vol. 36, 337-341, 2005.
Atkinson, G. E. et al., A Versatile Polymer-Supported 4-(4Methylphenyl(chloro)methyl)phenoxy Linker for Solid-Phase Synthesis of Pseudopeptides, Journal of Organic Chemistry, 2000, vol. 65, No. 16, p. 5048-5056.
Auerbach et al., Angiogenesis Assays: A Critical Overview, Clinical Chemistry, vol. 49, 32-40, 2003.
Aucella et al., Synergistic effect of desferrioxamine and recombinant erythropeoietin on erythroid precursor proliferation in chronic renal failure, Nephrol. Dial Transplant. May 1999; 14(5):1171-1175.
Barany et al., Solid-phase Peptide Synthesis: A Silver Anniversary Report, Int. J. Peptide Protein Res., vol. 30, No. 6, 705-739, 1987.
Baringhaus et al., 3D QSAR of prolyl 4-hydroxylase inhibitors, Chapter 23 in "Molecular Modeling and Prediction of Bioactivity" (Springer, Boston, MA), 2000, 345-346.
Bartlett et al., Molecular Recognition in Chemical and Biological Problems, Special Pub., Royal Chem. Soc., vol. 78, 182-196 Caveat: A Program to Facilitate the Structure-derived Design of Biologically Active Molecules, Apr. 1989.
Bohm, The Computer Program LUDI: A New Method for the Novo Design of Enzyme Inhibitors, J. Computer-Aided Molecular Design, vol. 6, 61-78, 1992.
Branden et al., Introduction to Protein Structure Second Edition, Garland Publishing, Inc., New York, pp. 374-375, 1999.
Burger, Isosterism and bioisosterism in drug design, Progress in Drug Research, vol. 37, 287-371,1991.
Bussolino, Molecular Mechanisms of Blood Vessel Formation, Trends Biochem. Sci., vol. 22, No. 7, 251-256, 1997.
Catrina et al., Hyperglycemia Regulates Hypoxia-Inducible Factor-Ia Protein Stability and Function, Diabetes, vol. 53, 3226-3232, 2004.
Cheeseright, The identification of bioisosteres as drug development candidates, Innovations in Pharmeceutical Technology, 22-26, 2009.
Cunliffe et al., Novel Inhibitors of Prolyl4-Hydroxylase. 3. Inhibition by the Substrate Analogue N-Oxaloglycine and Its Derivatives, J. Med. Chem. vol. 35, 2652-2658, 1992.
Elson et al., Induction of Hypervascularity Without Leakage or Inflammation in Transgenic Mice Overexpressing Hypoxia-Indicible Factor-la, Genes & Dev., vol. 15, 2520-2532, 2001.
Enoch et al., ABC of wound healing: non-surgical and drug treatments, BMJ, vol. 332, 900-903, 2006.
Exhibit SW2 to the first report of Simon Ward, filed on behalf of the Claimants in Claim No. HP-2018-000036 and the First and Second Defendants in IL-2019-000031, and the Claimants in Claim No. HP-2018-000032, in the High Court of Justice Business and Property Courts of England and Wales Intellectual Property List (ChD) Patent Court, Jan. 3, 2020 (23 pages).
Flower, Modelling G-protein-coupled receptors for drug design, Biochimica et Biophysica Acta, vol. 1422, 207-234, 1999.
Folkman et al., Tumor Angiogenesis, The Molecular Basis of Cancer, Mendelsohn et al., eds., W. B. Saunders, Chapter 10, pp. 206-232, 1995.
Franklin et al., Approaches to the Design of Anti-Fibrotic Drugs, Biochem. Soc. Trans., vol. 19, No. 4, :812-5, Nov. 1991.
Gavhane et al., Solid tumors: facts, challenges and solutions, International Journal of Pharma Sciences and Research, vol. 2, No. 1, 1-12, 2011.
Gaunt et al., Rational design of benzyl-type protecting groups allows sequential deprotection of hydroxyl groups by catalytic hydrogenolysis, J. Org. Chem., vol. 63, 4172-4173, 1998.
Goodford, A Computational Procedure for Determining Energetically Favorable Binding Sites on Biologically Important Macromolecules, J. Med. Chem., vol. 28, No. 7, 849-857, 1985.
Gunzler et al., Prolyl 4-hydroxylase inhibitors, Chapter 2 in Prolyl hydroxylase, protein disulfide isomerase, and other structurally related proteins (Marcel Dekker), 1998, 65-95.
Goodsell et al., Automated Docking of Substrates to Proteins by Simulated Annealing, Proteins: Structure, Function, and Genetics, vol. 8, 195-202, 1990.
Gupta et al., Hypoxia-Inducible Factor Prolyl Hydroxylase Inhibitors: A Potential New Treatment for Anemia in Patients With CKD, Am J Kidney Dis. 2017, vol. 69, issue 6, pp. 815-826. DOI: 10.1053/j.ajkd.2016.12.011 (Year: 2017).
Hardcastle et al., Discovery of potent chromen-4-one inhibitors of the DNA-dependent protein kinase (DNA-PK) using a small molecule library approach, J. Med. Chem., vol. 48, 7829-7846, 2005.
Hippuric acid sodium salt. Science Lab.com: Chemicals & Laboratory Equipment. (http://web.archive.org/web/20041107121553/http://www.sciencelab.com/page/S/PVAR/10415/SLH2620, accessed Mar. 11, 2010). 1 page.
Hirsila et al., Characterization of the Human Prolyl 4-Hyrdoxylases That Modify the Hypoxia-inducible Factor, The Journal of Biological Chemistry, vol. 278, No. 33, 30772-30780, Aug. 2003.
Hoeksema et al., Structure of Rubradirin, Journal of American Chemical Society, vol. 104, 5173-5181, 1982.
Ikura; Bioorganic & Medicinal Chemistry 14 (2006) 4241-4252. doi: 10.1016/j.bmc.2006.01.059 (Year: 2006).
Ingersoll et al., Organic Syntheses, CV 2, 328, "Hippuric acid". (http://web.archive.org/web/20020724135719/http://www.orgsyn.org/orgsyn/orgysn/prepContent.asp?prep=cv2p0328, accessed Mar. 11, 2010). 4 pages.
International Search Report dated May 8, 2008 for PCT/US2007/014832. 3 pages.
International Union of Pure and Applied Chemistry; Glossary of Class Names of Organic Compounds and Reactive Intermediates Based on Structure; Pure & D Appl. Chem., vol. 67, Nos. 8/9, 1307-1375, 1995.
Ivan et al., Biochemical purification and pharmacological inhibition of a mammalian prolyl hydroxylase acting on hypoxia-inducible factor, Proceedings of the National Academy of Science; vol. 99, No. 21, 13459-13464, 2002.
Ivan et al., HIFa Targeted for VHL-Mediated Destruction by Praline Hydroxylation: Implications for 02 Sensing, Science vol. 292, 464-468, 2001.
Jaakkola et al., Targeting of HIF-a to the von Rippel-Lindau Ubiquitylation Complex by O2-Regulated Prolyl Hydroxylation, Science, vol. 292, 468-472, 2001.
Jones et al., Molecular Recognition of Receptor Sites Using a Genetic Algorithm with a Description of Desolvation, J. Mol. Biol., vol. 245, 43-53, 1995.
Kaelin, Praline Hydroxylation and Gene Expression, Annu. Rev. Biochem., vol. 74, 115-125, 2005.
Kawashima et al., Suppressive effect of quinolinic acid and hippuric acid on bone marrow erythroid growth and lymphocyte blast formation in uremia, Advances in Experimental Medicine and Biology, vol. 223, 69-72, 1987.
Ke et al., Hypoxia-Inducible Factor-1 (HIF-1), Molecular Pharmacology, vol. 70, No. 5, 1469-1480, Aug. 2006.
Kim et al., Recent Advances in Developing Inhibitors for Hypoxia-Inducible Factor Prolyl Hydroxylases and Their Therapeutic Implications, Molecules, vol. 20, No. 11, 20551-20568, Nov. 2015.
Krantz, "Erythropoietin," Blood, vol. 77, 419-434, 1991.
Kuntz et al., A Geometric Approach to Macromolecule-Ligand Interactions, J. Mol. Biol., vol. 161,269-288, 1982.
Langsetmo, Inhibition of HIF-Prolyl Hydroxylases with FG-4539 Is Neuroprotective in a Mouse Model of Permanent Focal Ischemia, International Stroke Conference, Kissimmee, Florida, Presentation No. 427, 2006. 1 page.
Lee et al., Structure of Human FIH-1 Reveals a Unique Active Site Pocket and Interaction Sites for HIF-1 and von Hinnel Lindau, JBC, vol. 278, 7558-7563, 2003.
Li et al., PR39, A Peptide Regulator of Angiogenesis, Nat Med., vol. 6, No. 1, 49-55, 2000.
Lima et al., Bioisosterism: a useful strategy for molecular modification and drug design, Current Medicinal Chemistry, vol. 12, 23-49, 2005.
Mancini et al., Effect of Erythropoietin on Exercise Capacity in Patients with Moderate to Severe Chronic Heart Failure, Circulation, vol. 107, 294-299, 2003.

(56) References Cited

OTHER PUBLICATIONS

McDonough et al., Cellular Oxygen Sensing: Crystal Structure of Hypoxia-Inducible Factor Prolyl Hydroxylase (PHD2), Pnas, vol. 103 No. 26, 9814-9819, 2006.
Miranker et al., Functionality Maps of Binding Sites: A Multiple Copy Simultaneous Search Method, Proteins: Structure, Function and Genetics, vol. 11, 29-34, 1991.
Nguyen et al., Cellular Interactions in Vascular Growth and Differentiation, Int. Review of Cytology, vol. 204, 1-48, 2001.
Nishibata et al., Automatic Creation of Drug Candidate Structures Based on Receptor Structure. Starting Point for Artificial Lead Generation, Tetrahedron, vol. 47, No. 43, 8985-8990, 1991.
Notice of Opposition communication for European Patent No. 3357911, dated Feb. 23, 2023. 26 pages.
O'Reilly et al., Angiostatin: A Novel Angiogenesis Inhibitor that Mediates the Suppression of Metastases bv a Lewis Lung Carcinoma, Cell, vol. 79, 315-328, 1994.
O'Reilly et al., "Endostatin: An Endogenous Inhibitor of Angiogenesis and Tumor Growth," Cell, 88:277-285 (1997).
Pergola et al., Vadadustat, a novel oral HIF stabilizer, provides effective anemia treatment in nondialysis-dependent chronic kidney disease, Kidney International, vol. 90, No. 5, 1115-1122, Sep. 2016.
Peyssonnaux et al., HIF-Ia Expression Regulates the Bactericidal Capacity of Phagocytes, J. Clinical Invest., vol. 115, No. 7, 1806-1815, 2005.
Piyamongkol et al., Amido-3-hydroxypyridin-4-ones as iron(III) ligands, Chemistry, A European Journal, vol. 16, 6374-6381, 2010.
Qian et al., A Randomized, Double-Blind, Placebo Controlled Trial ofFG-4592 for Correction of Anemia in Subjects with Chronic Kidney Disease in China, Oral Abstract FR-ORO11, J. Am. Soc. Nephrol., vol. 24:38A, 2013. 1 page.
Rahtu-Korpela, HIF Prolyl 4-Hydroxylase-2 Inhibition Improves Glucose and Lipid Metabolism and Protects Against Obesity and etabolic Dysfunction, Diabetes, vol. 63, 3324-3333, 2014.
Schelhaas et al., Protecting group strategies in organic synthesis, Angew, Chem. Int. Ed. Engl., vol. 35, 2056-2083, 1996.
Schoneberg et al., Structural Basis of G Protein-Coupled Receptor Function, Molecular and Cellular Endocrinology, vol. 151, 181-193, 1999.
Search Report dated Apr. 28, 2011 for European Pat. App. No. 11000872.9. 3 pages.
Semenza, HIF-1 and human disease: one highly involved factor, Genes and Development, vol. 14, No. 16, 1983-1991, Aug. 2000.
Semenza et al., Transcriptional Regulation of Genes Encoding Glycolytic Enzymes by Hypoxia-Inducible Factor I , J. Biol. Chem., vol. 269, 23757-23763, 1994.
Semenza, Regulation of Erythropoietin Porduction: New Insights into Molecular Mechanisms of Oxygen Homeostasis, Hematol. Oncol. Clin. North Am., vol. 8, 863-884, 1994.
Semenza, Signal Transduction to Hypoxia-inducible Factor I , Biochem. Pharmacol, vol. 64, 993-998, 2002.
Sexton, Recent advances in our understanding of peptide hormone receptors and RAMPS, Current Opinion in Drug Discovery and Development, vol. 2, No. 5. 440-448, 1999.
Sheehan, 3-Hydroxypicolinic Acid and Some of its Derivatives, J. Organic Chemistry, vol. 31, No. 3, 636-638, 1996.
Siddiq et al., Hypoxia-inducible Factor Prolyl 4-Hydroxylase Inhibition, The Journal of Biological Chemistry, vol. 280, No. 50, 41732-41743, Dec. 2005.
Silverman, The Organic Chemistry of Drug Design and Drug Action, 2nd Edition, 2004, Elsevier, Section 2.2, E.4, pp. 29-34.
Standards of Medical Care in Diabetes-2006, Diabetes Care, vol. 29. 4-s42, 2006. 39 pages.
Sutter et al., Hypoxia-inducible factor 1α protein expression is controlled by oxygen-regulated ubiquitination that is disrupted by deletions and missense mutations, PNAS, vol. 97, No. 9, 4748-4753, 2000.
Teicher et al., Potentiation of Cytotoxic Cancer Therapies by TNP-470 Alone and with Other Anti-Angiogenic Agents, Int. J. Cancer, vol. 57, 920-925, 1994.
Thornber, Isosterism and molecular modification in drug design, Chem Soc. Rev., vol. 8, 563-580, 1979.
Tzschucke et al., Fluorous-Silica-Supported Perfluoro-Tagged Palladium Complexes Catalyze Suzuki Coupling in Water, Helvetica Chimica Acta; vol. 87, 2882-2889, 2004.
Vickerstaffe et al., Fully Automated Polymer-Assisted Synthesis of 1,5-Biaryl Pyrazoles, J. Comb. Chem., vol. 6, 332-33, 2004.
Vincent et al., Angiogenesis is Induced in a Rabbit Model of Hindlimb Ischemia by Naked DNA Encoding an HIF-I aNP16 Hybrid Transcription Factor, Circulation, vol. 102, 2255-2261, 2000.
Warnecke et al., Activation of the Hypoxia-Inducible Factor Pathway and Stimulation of Angiogenesis by Application of Prolyl Hydroxylase Inhibitors, FASEB Journal, vol. 17, 1186-1188, 2003.
Warshakoon et al., Design and synthesis of substituted pyridine derivatives as HIF-1alpha prolyl hydroxylase inhibitors, Bioorganic & Medicinal Chemistry Letters, vol. 16, 5616-5620, 2006.
Wax et al., SM-20 is a Novel20-kd Protein Whose Expression in the Arterial Wall is Restricted to Smooth Muscle, Lab. Invest., vol. 74, No. 4, 797-808, 1996.
Weidner et al., Tumor Angiogenesis and Metastasis—Correlation in Invasive Breast Carcinoma, New Eng. J. Med., vol. 324, No. 1, 1-8, 1991.
Wright et al., Activation of the Prolyl Hydroxylase Oxygen-Sensor Results in Induction of GLUTI, Heme Oxygenase-1, and Nitric-Oxide Synthase Proteins and Confers Protection from Metabolic Inhibition to Cardiomyocytes, J. Bio. Chem., vol. 278, No. 22, 20235-20239, 2003.
European Patent No. 2044005, Opposition Filed, Jul. 20, 2011. 51 pages.
European Patent No. 2044005, Response to Opposition, Dec. 28, 2011. 9 pages.
European Patent No. 2044005, Summons to Attend Oral Proceedings and Preliminary Opinion of the Opposition Division, Oct. 31, 2012. 5 pages.
European Patent No. 2044005, Decision of the Opposition Division, Instruction, and Grounds for the Decision, May 3, 2013. 21 pages.
European Patent No. 2044005, Patent Owner Statement of Grounds of Appeal, Sep. 13, 2013. 14 pages.
European Patent Office, Interlocutory Decision in Opposition Proceedings, mailed May 3, 2013, 76 pages.
European Patent Office, Minutes of the Oral Proceedings Before the Opposition Division, mailed May 3, 2013, 6 pages.
European Patent No. 2044005, Opponent Statement of Grounds of Appeal, Sep. 13, 2013. 16 pages.
European Patent No. 2044005, Opponent Reply to Appeal, Jan. 29, 2014. 30 pages.
European Patent No. 2044005, Patent Owner Reply to Appeal, Jan. 29, 2014. 26 pages.
European Patent No. 2044005, Patent Owner Response to the Opponent's Communication, Aug. 28, 2014. 50 pages.
European Patent No. 2044005, Communication of the Board of Appeal, Aug. 29, 2017. 12 pages.
European Patent No. 2044005, Response of Opponent to Communication of the Board of Appeal, Nov. 8, 2017. 30 pages.
Withdrawal of an Appeal by Proprietor in the Opposition Against European Patent No. 2044005, Feb. 27, 2018. 3 pages.
Decision of the Board of Appeal of the European Patent Office in the Opposition Against European Patent No. 2044005, Mar. 6, 2018. 6 pages.
Termination of Opposition Proceedings of European Patent No. 2044005, Apr. 18, 2018. 1 page.
Notice of Opposition u/s 25(2) filed on Sep. 25, 2018 by Dr. Reddy's Laboratories Limited against Indian Patent No. 287720. 237 pages.
Reply Statement of Patentee, filed Jan. 15, 2019, in the Post Grant Opposition against Indian Patent No. 287720 (39 pages).
Reply on Behalf of Opponent to the Counterstatement by the Patentee and Reply Evidence, submitted Feb. 14, 2019, in the Post Grant Opposition against Indian Patent No. 287720 (237 pages).

\* cited by examiner

Immunoblot analysis of nuclear extracts demonstrating stabilization of HIF-1α in mouse liver by {[5-(3-chlorophenyl)-3-hydroxypyridine-2-carbonyl]amino}-acetic acid Elevated erythropoietin levels in mouse serum following oral dosing of a compound, {[5-(3-chlorophenyl)-3-hydroxypyridine-2-carbonyl]amino}-acetic acid as compared with a vehicle.

mean ± SEM, n = 4

```
                        SEQUENCE LISTING

Sequence total quantity: 1
SEQ ID NO: 1           moltype = AA   length = 19
FEATURE                Location/Qualifiers
REGION                 1..19
                       note = HIF-1 alphapeptide corresponding to aa residues
                       556-574 for useas substrate to measure EGLN-1 (or EGLN-3)
                       activity
source                 1..19
                       mol_type = protein
                       organism = unidentified
SEQUENCE: 1
DLDLEALAPY IPADDDFQL                                                       19
```

PROLYL HYDROXYLASE INHIBITORS AND METHODS OF USE

PRIORITY

This application is a Continuation Application of U.S. application Ser. No. 16/908,092, filed Jun. 22, 2020, which is a Continuation Application of U.S. application Ser. No. 16/119,146, filed Aug. 31, 2018, now U.S. Pat. No. 10,729,681, issued on Aug. 4, 2020, which is a Continuation Application of U.S. application Ser. No. 15/420,617, filed Jan. 31, 2017, now abandoned, which is a Continuation Application of U.S. application Ser. No. 14/854,080, filed Sep. 15, 2015, now U.S. Pat. No. 9,598,370, issued on Mar. 21, 2017, which is a Continuation Application of U.S. application Ser. No. 14/568,200, filed on Dec. 12, 2014, now abandoned, which is a Continuation Application of U.S. application Ser. No. 14/062,011, filed Oct. 24, 2013, now U.S. Pat. No. 8,940,773, issued on Jan. 27, 2015, which is a Divisional Applications of U.S. application Ser. No. 13/681,876, filed on Nov. 20, 2012, now U.S. Pat. No. 8,598,210, issued on Dec. 3, 2013, which is a Continuation of U.S. application Ser. No. 12/860,073, filed on Aug. 20, 2010, now U.S. Pat. No. 8,343,952, issued on Jan. 1, 2013, which is a Continuation Application of U.S. application Ser. No. 11/821,936, filed Jun. 26, 2007, now U.S. Pat. No. 7,811,595, issued on Oct. 12, 2010, which claims the benefit of Provisional Application No. 60/816,522 filed on Jun. 26, 2006, the entire disclosures of which are incorporated herein by reference in their entirety.

INCORPORATION BY REFERENCE OF SEQUENCE LISTING

The contents of the file named "AKE_001US13_SequenceListing.xml", which was created on Jul. 26, 2022 and is 2,359 bytes in size, are hereby incorporated by reference in their entirety.

FIELD OF THE DISCLOSURE

The present disclosure relates, in some aspects, to HIF-1 α prolyl hydroxylase inhibitor compounds and pharmaceutically acceptable salts thereof, compositions comprising the HIF-1 α prolyl hydroxylase inhibitor compounds, and to methods for treating or controlling, inter alia, Peripheral Vascular Disease (PVD), Coronary Artery Disease (CAD), heart failure, ischemia, and anemia.

BACKGROUND OF THE DISCLOSURE

HIF-1 α under normal healthy conditions wherein the cells have a sufficient supply of oxygen is readily converted to a degraded form by one of several prolyl hydroxylase enzymes, inter alia, EGLIN. When cells undergo hypoxia, this enzymatic transformation is slow or entirely stopped and HIF-1 α begins to build up in the cell. When this build up of HIF-1 α occurs, this protein combines with another factor, HIF-1 β which together form an active transcription factor complex. This transcription factor then activates several biological pathways which are present as a response to and a means for alleviating the body's state of hypoxia. These responses include, inter alia, angiogenic, erythropoietic (EPO), glucose metabolism, and matrix alteration responses.

In patients where there is a need for stimulating one or more of these responses, for example, in patients in need of increased tissue oxygen due to peripheral vascular disease (PVD), inhibiting the EGLIN enzyme will stimulate the body's own angiogenic response without the consequences of oxygen deficiency. In addition, in diseases of ischemia, inter alia, CAD and anemia, stimulation of angiogenic, erythropoietic, and metabolic adaptation would be expected to provide therapeutic benefits.

Therefore there continues to be a long felt need for compounds that inhibit prolyl hydroxylase enzymes and thereby regulate the concentration of HIF-1α in cells so as to induce angiogenic or erythropoietic responses and therefore treat diseases related to hypoxia or anemia.

SUMMARY OF THE DISCLOSURE

The substituted aryl or heteroaryl amide compounds of the present disclosure are a new class of compounds that can inhibit HIF-1α prolyl hydroxylase, thus resulting in improvement in blood flow, oxygen delivery and energy utilization in ischemic tissues, or upregulate the production of erythropoietin so as to treat anemia.

Disclosed herein are compounds and pharmaceutically acceptable salts thereof, and/or pharmaceutical compositions thereof comprising:
  a) an effective amount of one or more compounds according to the present disclosure; and
  b) an excipient.

The present disclosures also relate to methods for controlling, inter alia, Peripheral Vascular Disease (PVD), Coronary Artery Disease (CAD), heart failure, ischemia, and/or anemia.

The present disclosures also relate to methods for regulating blood flow, oxygen delivery and/or energy utilization in ischemic tissues, wherein the methods can comprise administering to a human an effective amount of one or more compounds or pharmaceutically acceptable salts disclosed herein.

These and other objects, features, and advantages will become apparent to those of ordinary skill in the art from a reading of the following detailed description and the appended claims. All documents cited herein are in relevant part, incorporated herein by reference; the citation of any document is not to be construed as an admission that it is prior art with respect to the present disclosure.

DETAILED DESCRIPTION OF THE DISCLOSURE

Figure 1:
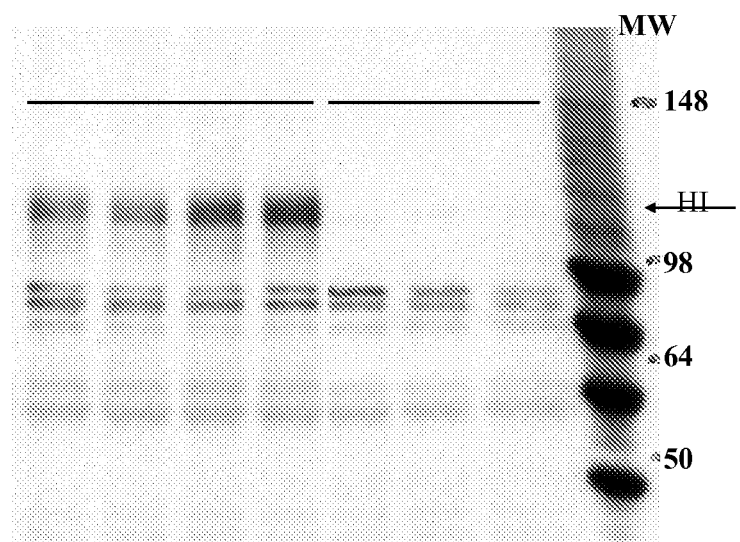
FIG. 1. Immunoblot analysis of nuclear extracts demonstrating stabilization of HIF-1α in mouse liver by {[5-(3-chlorophenyl)-3-hydroxypyridine-2-carbonyl]amino}-acetic acid FIG. 2. An example of how the erythropoietin level is elevated versus vehicle in mouse serum after oral dosing of {[5-(3-chlorophenyl)-3-hydroxypyridine-2-carbonyl]-amino}-acetic acid.
Figure 2:
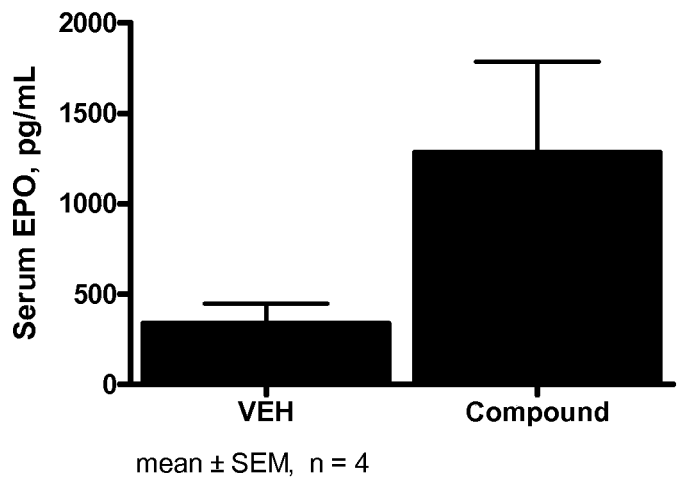

In this specification and in the claims that follow, reference will be made to a number of terms, which shall be defined to have the following meanings:

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "organic unit" as described herein refers to groups or moieties that comprise one or more carbon atoms and which form a portion of one of the compounds or pharmacetucally acceptable salts thereof. For example, many of the substitutent units referred to elsewhere herein are organic units. In order to effectively function in the context of their presence in the compounds and/or salts disclosed herein, the organic units should often have variable ranges of restricted size and/or molecular weight, so as to provide desired binding to the target enzymes, solublility, bioabsorption characteristics. For example, organic unit can have, for example, 1-26 carbon atoms, 1-18 carbon atoms, 1-12 carbon atoms, 1-8 carbon atoms, or 1-4 carbon atoms. Organic units often have hydrogen bound to at least some of the carbon atoms of the organic units, and can optionally contain the common heteroatoms found in substituted organic compounds, such as oxygen, nitrogen, sulfur, and the like, or inorganic atoms such as halogens, phosphorus, and the like. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Substituted and unsubstituted linear, branched, or cyclic alkyl units include the following non-limiting examples: methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$), cyclobutyl ($C_4$), cyclopentyl ($C_5$), cyclohexyl ($C_6$), and the like; whereas substituted linear, branched, or cyclic alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 2,2,2-trifluoroethyl ($C_3$), 3-carboxypropyl ($C_3$), 2,3-dihydroxycyclobutyl ($C_4$), and the like.

Substituted and unsubstituted linear, branched, or cyclic alkenyl include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

Substituted and unsubstituted linear or branched alkynyl include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

Substituted and unsubstituted "alkoxy" are used herein denotes a unit having the general formula —$OR^{100}$ wherein $R^{100}$ is an alkyl, alkylenyl, or alkynyl unit as defined herein above, for example, methoxy, methoxymethyl, methoxymethyl.

Substituted and unsubstituted "haloalkyl" are used herein denotes an alkyl unit having a hydrogen atom substituted by one or more halogen atoms, for example, trifluoromethyl, 1,2-dicloroethyl, and 3,3,3-trifluoropropyl.

The term "aryl" as used herein denotes cyclic organic units that comprise at least one benzene ring having a conjugated and aromatic six-membered ring, non-limiting examples of which include phenyl ($C_6$), naphthylen-1-yl ($C_{10}$), naphthylen-2-yl ($C_{10}$). Aryl rings can have one or more hydrogen atoms substituted by another organic or inorganic radical. Non-limiting examples of substituted aryl rings include: 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyanonaphthylen-1-yl ($C_{10}$).

The term "heteroaryl" denotes an organic unit comprising a five or six membered conjugated and aromatic ring wherein at least one of the ring atoms is a heteroatom selected from nitrogen, oxygen, or sulfur. The heteroaryl rings can comprise a single ring, for example, a ring having 5 or 6 atoms wherein at least one ring atom is a heteroatom not limited to nitrogen, oxygen, or sulfur, such as a pyridine ring, a furan ring, or thiofuran ring. A "heteroaryl" can also be a fused multicyclic and heteroaromatic ring system having wherein at least one of the rings is an aromatic ring and at least one atom of the aromatic ring is a heteroatom including nitrogen, oxygen, or sulfur The following are non-limiting examples of heteroaryl rings according to the present disclosure:

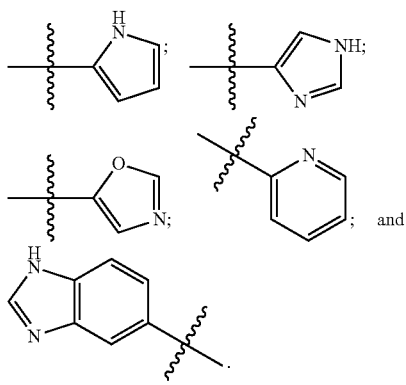

The term "heterocyclic" denotes a ring system having from 3 to 10 atoms wherein at least one of the ring atoms is a heteroatom not limited to nitrogen, oxygen, or sulfur. The rings can be single rings, fused rings, or bicyclic rings. Non-limiting examples of heterocyclic rings include:

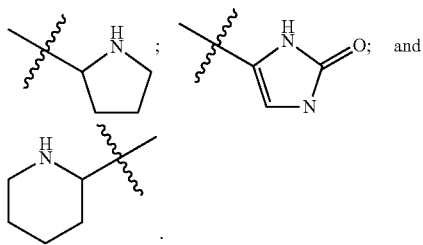

All of the aforementioned heteroaryl or heterocyclic rings can be optionally substituted with one or more substitutes for hydrogen as described herein further.

Throughout the description of the present disclosure the terms having the spelling "thiophene-2-yl and thiophene-3-yl" are used to describe the heteroaryl units having the respective formulae:

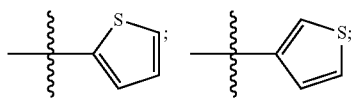 [SMILES: *c1cccs1 ; *c1ccsc1]

whereas in naming the compounds of the present disclosure, the chemical nomenclature for these moieties are typically spelled "thiophen-2-yl and thiophen-3-yl" respectively.

Herein the terms "thiophene-2-yl and thiophene-3-yl" are used when describing these rings as units or moieties which make up the compounds of the present disclosure solely to make it unambiguous to the artisan of ordinary skill which rings are referred to herein.

The following are non-limiting examples of units which can substitute for hydrogen atoms on a hydrocarbyl or other unit:

i) linear, branched, or cyclic alkyl, alkenyl, and alkynyl; for example, methyl ($C_1$), ethyl ($C_2$), n-propyl ($C_3$), iso-propyl ($C_3$), cyclopropyl ($C_3$), propylen-2-yl ($C_3$), propargyl ($C_3$), n-butyl ($C_4$), iso-butyl ($C_4$), sec-butyl ($C_4$), tert-butyl ($C_4$), cyclobutyl ($C_4$), n-pentyl ($C_5$), cyclopentyl ($C_5$), n-hexyl ($C_6$), and cyclohexyl ($C_6$);

ii) substituted or unsubstituted aryl; for example, phenyl, 2-fluorophenyl, 3-chlorophenyl, 4-methylphenyl, 2-aminophenyl, 3-hydroxyphenyl, 4-trifluoromethylphenyl, and biphenyl-4-yl;

iii) substituted or unsubstituted heterocyclic; examples of which are provided herein below;

iv) substituted or unsubstituted heteroaryl; examples of which are provided herein below;

v) $-(CR^{12a}R^{12b})_q OR^{11}$; for example, $-OH$, $-CH_2OH$, $-OCH_3$, $-CH_2OCH_3$, $-OCH_2CH_3$, $-CH_2OCH_2CH_3$, $-OCH_2CH_2CH_3$, and $-CH_2OCH_2CH_2CH_3$;

vi) $-(CR^{12a}R^{12b})_q C(O)R^{11}$; for example, $-COCH_3$, $-CH_2COCH_3$, $-OCH_2CH_3$, $-CH_2COCH_2CH_3$, $-COCH_2CH_2CH_3$, and $-CH_2COCH_2CH_2CH_3$;

vii) $-(CR^{12a}R^{12b})_q C(O)OR^{11}$; for example, $-CO_2CH_3$, $-CH_2CO_2CH_3$, $-CO_2CH_2CH_3$, $-CH_2CO_2CH_2CH_3$, $-CO_2CH_2CH_2CH_3$, and $-CH_2CO_2CH_2CH_2CH_3$;

viii) $-(CR^{12a}R^{12b})_q OC(O)N(R^{11})_2$; for example, $-CONH_2$, $-CH_2CONH_2$, $-CONHCH_3$, $-CH_2CONHCH_3$, $-CON(CH_3)_2$, and $-CH_2CON(CH_3)_2$;

ix) $-(CR^{12a}R^{12b})_q OC(O)N(R^{11})_2$; for example, $-OC(O)NH_2$, $-CH_2OC(O)NH_2$, $-OC(O)NHCH_3$, $-CH_2OC(O)NHCH_3$, $-OC(O)N(CH_3)_2$, and $-CH_2OC(O)N(CH_3)_2$;

x) $(CR^{12a}R^{12b})_q N(R^{11})_2$; for example, $-NH_2$, $-CH_2NH_2$, $-NHCH_3$, $-N(CH_3)_2$, $-NH(CH_2CH_3)$, $-CH_2NHCH_3$, $-CH_2N(CH_3)_2$, and $-CH_2NH(CH_2CH_3)$;

xi) halogen: $-F$, $-Cl$, $-Br$, and $-I$;

xii) $-CH_mX_n$; wherein X is halogen, m is from 0 to 2, m+n=3; for example, $-CH_2F$, $-CHF_2$, $-CF_3$, $-CCl_3$, or $-CBr_3$;

xiii) $-(CR^{12a}R^{12b})_q CN$; for example; $-CN$, $-CH_2CN$, and $-CH_2CH_2CN$;

xiv) $-(CR^{12a}R^{12b})_q NO_2$; for example; $-NO_2$, $-CH_2NO_2$, and $-CH_2CH_2NO_2$;

xv) $-(CR^{12a}R^{12b})_q SO_2R^{11}$; for example, $-SO_2H$, $-CH_2SO_2H$, $-SO_2CH_3$, $-CH_2SO_2CH_3$, $-SO_2C_6H_5$, and $-CH_2SO_2C_6H_5$; and xvi) $-(CR^{12a}R^{12b})_q SO_3R^{11}$; for example, $-SO_3H$, $-CH_2SO_3H$, $-SO_3CH_3$, $-CH_2SO_3CH_3$, $-SO_3C_6H_5$, and $-CH_2SO_3C_6H_5$;

xvii) hydroxyl groups or thiol groups, xviii) amino groups, monosubstituted amino, or disubstituted amino, wherein each $R^{11}$ is independently hydrogen, substituted or unsubstituted $C_1$-$C_4$ linear, branched, or cyclic alkyl; or two $R^{11}$ units can be taken together to form a ring comprising 3-7 atoms; $R^{12a}$ and $R^{12b}$ are each independently hydrogen or $C_1$-$C_4$ linear or branched alkyl; the index q is from 0 to 4.

The compounds and compositions recited herein can have a number of utilities, and address several unmet medical needs, inter alia;

1) Providing compositions effective as inhibitors of human protein prolyl hydroxylase, thereby stimulating an angiogenic response in human tissue, thereby providing a method for increasing blood flow, oxygen delivery and energy utilization in ischemic tissues;
2) Providing compositions effective as human protein HIF-1α prolyl hydroxylase inhibitors, and thereby increasing the concentration of HIF-1α leading to greater activation and sustaining the of various biological pathways that are the normal response to cellular hypoxia;
3) Providing compositions effective in stimulating an erythropoietic (EPO) response in cells and thereby enhancing the maintenance of red blood cells by controlling the proliferation and differentiation of erythroid progenitor cells into red blood cells;
4) Providing compositions effective in stimulating an angiogenic response and thereby increasing the number and density of blood vessels and thus alleviating the adverse consequences of hypertension and diabetes, inter alia, claudication, ischemic ulcers, accelerated hypertension, and renal failure;
5) Providing compositions that activate Vascular Endothelial Growth Factor (VEGF) gene transcription in hypoxic cells thus increasing stimulus of important biological responses, inter alia, vasodilation, vascular permeability, and endothelial cell migration and proliferation.

Therefore, these and other unmet medical needs are resolved by the HIF-1α prolyl hydroxylase inhibitors of the present disclosure, which are capable of regulating blood flow, oxygen delivery and energy utilization in ischemic tissues that are caused by insufficient regulation of HIF-1α prolyl hydroxylase. Those of skill in the art will also recognize that inhibition of HIF-1α prolyl hydroxylase enzymes will have other positive medical effects on human tissue and the alleviation of symptoms and disease states other than those symptoms or diseases states that are specifically pointed out in the present disclosure. However, as greater details arise concerning disease states and conditions related to the angiogenic process, these yet undisclosed or yet unknown conditions will be positively affected by compositions which stimulate the body own response to hypoxia and other low blood oxygen conditions.

For the purposes of the present disclosure the terms "compound," "analog," and "composition of matter" stand equally well for the HIF-1α prolyl hydroxylase enzyme inhibitors described herein, including all enantiomeric forms, diastereomeric forms, salts, and the like, and the terms "compound," "analog," and "composition of matter" are used interchangeably throughout the present specification.

The compounds disclosed herein include all salt forms, for example, salts of both basic groups, inter alia, amines, as well as salts of acidic groups, inter alia, carboxylic acids. The following are non-limiting examples of anions that can form pharmaceutically acceptable salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form pharmaceutically acceptable salts of the anionic form of acidic substituent groups on the compounds described herein: sodium, lithium, potassium, calcium, magnesium, zinc, bismuth, and the like.

The HIF-1α prolyl hydroxylase inhibitor compounds described herein are substituted aryl or heteroaryl amides, having the core structure shown in Formula (I) below.

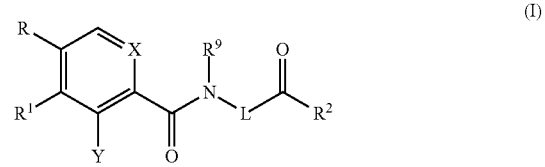

wherein X can be N or CH; L is an organic linking unit as further described, below, and Y, R, R¹ and R² can be any of the units further described below.

When X is a nitrogen atom the compounds of the present disclosure are 2-amidopyridines and when X is CH the compounds of the present disclosure are arylamides, as shown below:

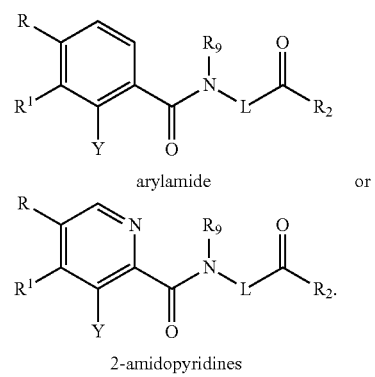

R and R¹ are optional substituent groups that can be independently chosen from a wide variety of inorganic (hydrogen, hydroxyl, amino, halogen or the like) or organic substituent units, such as alkyls, cycloalkyls, heterocyclic, heteroaryls, and the like, wherein such substituent units can optionally have from 1 to 12 carbon atoms, or 1 to 10 carbon atoms, or 1 to six carbon atoms. In many aspects of the invention, R and R¹ can each be independently a chosen from:

i) hydrogen;
ii) substituted or unsubstituted phenyl; and
iii) substituted or unsubstituted heteroaryl.

wherein the optional substituent units for the phenyl and heteroaryl rings can be chosen from a wide variety of inorganic and $C_1$-$C_4$ organic radicals, and there are typically zero, one, two, or three of such substituent groups. In many such aspects, one, two, or three substituents for the above-mentioned phenyl and heteroaryl rings can be independently selected from:

i) $C_1$-$C_4$ linear, branched, or cyclic alkyl;
ii) $C_1$-$C_4$ linear, branched, or cyclic alkoxy;
iii) $C_1$-$C_4$ linear, branched, or cyclic haloalkyl;
iv) halogen;
v) —CN;
vi) —NHC(O)R⁴ vii) —C(O)NR$^{5a}$R$^{5b}$;
viii) heteroaryl; or
ix) two substitutions can be taken together to form a fused ring having from 5 to 7 atoms;

wherein the above-mentioned R$^4$ unit can be hydrogen or a C$_1$-C$_4$ linear, branched, or cyclic alkyl; and wherein the R$^{5a}$ and R$^{5b}$ units can be independently selected from:
i) hydrogen;
ii) C$_1$-C$_4$ linear, branched, or cyclic alkyl; or
iii) R$^{5a}$ and R$^{5b}$ can be taken together to form a ring having from 3 to 7 atoms.

In some aspects of the compounds of Formula (I), the R units can be chosen from substituted or unsubstituted phenyl; or substituted or unsubstituted heteroaryls; and the R$^1$ units are hydrogen.

In other aspects of the compounds of Formula (I), R can be a substituted or unsubstituted phenyl, having one, two, or three optional inorganic or organic substituents, which in some embodiments are chosen from:
i) C$_1$-C$_4$ linear, branched, or cyclic alkyl;
ii) C$_1$-C$_4$ linear, branched, or cyclic alkoxy;
iii) C$_1$-C$_4$ linear, branched, or cyclic haloalkyl;
iv) halogen; or
v) —CN.

Non-limiting examples of R units include 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-ethylphenyl, 3-ethylphenyl, 4-ethylphenyl, 2-iso-propylphenyl, 3-iso-propylphenyl, 4-iso-propylphenyl, 2-cyanophenyl, 3-cyanophenyl, 4-cyanophenyl, 2-methoxyphenyl, 3-methoxyphenyl, 4-methoxyphenyl, 2-ethoxyphenyl, 3-ethoxyphenyl, 4-ethoxyphenyl, 2-iso-propoxyphenyl, 3-iso-propoxyphenyl, 4-iso-propoxyphenyl, 2-cyanophenyl, 3-cyanophenyl, 4-cyanophenyl, 2-trifluoromethylphenyl, 3-trifluoromethylphenyl, and 4-trifluoromethylphenyl.

In additional aspects of the compounds of Formula (I) the R units can have the formula —NH(C(O)R$^4$ wherein R$^4$ is C$_1$-C$_4$ linear, branched, or cyclic alkyl. Non limiting examples of such R units include:
i) —NH(C(O)CH$_3$;
ii) —NH(C(O)CH$_2$CH$_3$;
ii) —NH(C(O)CH$_2$CH$_2$CH$_3$;
ii) —NH(C(O)CH(CH$_3$)$_2$;
ii) —NH(C(O)(cyclopropyl); and
ii) —NH(C(O)CH$_2$CH$_2$CH$_2$CH$_3$.

In additional aspects of the compounds of Formula (I), the R units can have the formula:

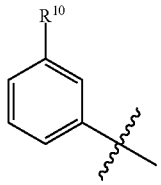

wherein R$^{10}$ has the formula —C(O)NR$^{5a}$R$^{5b}$; wherein R$^{5a}$ and R$^{5b}$ can be independently selected from hydrogen, C$_1$-C$_4$ linear or branched alkyls, or R$^{5a}$ and R$^{5b}$ are taken together to from a ring having 5 or 6 atoms. In some such aspects, the R$^{10}$ units can have the formula: —C(O)NR$^{5a}$R$^{5b}$ wherein R$^{5a}$ and R$^{5b}$ are each independently selected from hydrogen, methyl, ethyl, n-propyl, iso-propyl, and cyclopropyl. Non-limiting examples of such R$^{10}$ units include:

i) —C(O)NH$_2$;
ii) —C(O)NHCH$_3$;
iii) —C(O)N(CH$_3$)$_2$;
iv) —C(O)NH(CH$_2$CH$_3$);
v) —C(O)N(CH$_2$CH$_3$)$_2$;
vi) —C(O)N(CH$_3$)(CH$_2$CH$_3$).
vii) —C(O)NH(CH$_2$CH$_2$CH$_3$);
viii) —C(O)N(CH$_2$CH$_2$CH$_3$)$_2$;
ix) —C(O)NH[CH(CH$_3$)$_2$];
x) —C(O)N[CH(CH$_3$)$_2$]$_2$;
xi) —C(O)N(CH$_2$CH$_2$CH$_3$)[CH(CH$_3$)$_2$]; and
xii) —C(O)NH(cyclopropyl).

In additional aspects of the compounds of Formula (I), R$^{5a}$ and R$^{5b}$ together to form a ring having 5 or 6 ring atoms, non-limiting examples of R$^{10}$ units are heteroaryl units chosen from pyrrolidin-1-yl, piperidin-1-yl, piperazin-1-yl, and morpholin-4-yl.

In additional aspects of the compounds of Formula (I), the R$^{10}$ units can be heteroaryl units, non limiting examples of which are thiazol-2-yl, thiazol-4-yl, 1,2,3,4-tetrazol-5-yl, [1,2,4]triazol-5-yl, imidazol-2-yl, furan-2-yl, furan-3-yl, thiophene-2-yl, thiophene-3-yl, 1,2,3,4-tetrazol-5-yl, [1,2,4]triazol-5-yl, imidazol-2-yl, furan-2-yl, furan-3-yl, pyridin-2-yl, pyridin-3-yl, pyridin-4-yl, pyrimidin-2-yl, pyrimidin-4-yl, pyrimidin-5-yl, isoquinolin-1-yl, isoquinolin-3-yl, and isoquinolin-4-yl.

In additional aspects of the compounds of Formula (I), the R units can include substituted phenyl units wherein two substitutions can be taken together to form a fused ring having from 5 to 7 ring atoms, for example a 2,3-dihydrobenzo[1,4]dioxin-6-yl ring which would provide a compound having the formula:

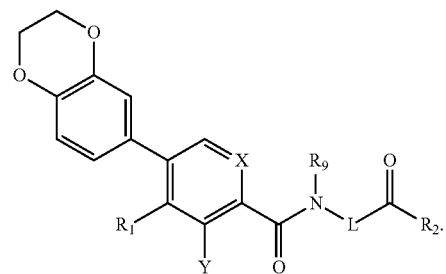

Other examples of R include units wherein R is hydrogen and R$^1$ is hydrogen.

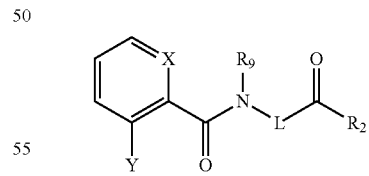

wherein R$^2$, X, Y, L, and R$^9$ can be independently chosen in any manner as otherwise taught herein with respect to the compounds of Formula (I).

As described previously above, the R$^1$ substituents for compounds of Formula (I) can be chosen from a wide variety of inorganic and organic units. In some embodiments, R$^1$ is a phenyl ring, which can optionally be substituted with 1, 2, or 3 substituent units, independently selected from inorganic or C$_1$-C$_4$ organic units. In some are chosen from:

i) $C_1$-$C_4$ linear, branched, or cyclic alkyl;
ii) $C_1$-$C_4$ linear, branched, or cyclic alkoxy;
iii) $C_1$-$C_4$ linear, branched, or cyclic haloalkyl;
iv) halogen; or
v) —CN.

Non-limiting examples of $R^1$ include 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-ethylphenyl, 3-ethylphenyl, 4-ethylphenyl, 2-iso-propylphenyl, 3-iso-propylphenyl, 4-iso-propylphenyl, 2-cyanophenyl, 3-cyanophenyl, 4-cyanophenyl, 2-methoxyphenyl, 3-methoxyphenyl, 4-methoxyphenyl, 2-ethoxyphenyl, 3-ethoxyphenyl, 4-ethoxyphenyl, 2-iso-propoxyphenyl, 3-iso-propoxyphenyl, 4-iso-propoxyphenyl, 2-cyanophenyl, 3-cyanophenyl, 4-cyanophenyl, 2-trifluoromethylphenyl, 3-trifluoromethylphenyl, and 4-trifluoromethylphenyl.

Another example of $R^1$ units includes compounds wherein R is hydrogen and $R^1$ units are hydrogen.

In some aspects of the compounds of Formula (I), R is hydrogen and $R^1$ is a substituted or unsubstituted phenyl, wherein the substitutions are chosen from:
i) $C_1$-$C_4$ linear, branched, or cyclic alkyl;
ii) $C_1$-$C_4$ linear, branched, or cyclic alkoxy;
iii) $C_1$-$C_4$ linear, branched, or cyclic haloalkyl;
iv) halogen; and
v) —CN.

In connection with the compounds of Formula (I), Y is a unit that can be chosen from a wide variety of inorganic units, such as H, —OH, —$NH_2$, or a halogen, and $C_1$-$C_4$ organic units. For example, Y can be chosen from:
i) hydrogen;
ii) —$OR^3$, wherein $R^3$ is hydrogen, or a lower alkyl, such as methyl, or ethyl.

In connection with the compounds of Formula (I), the $R^2$ units can be chosen from a wide variety of inorganic units, such as —OH, or —$NH_2$ units, or a variety of organic units.

In some aspects fo the compounds of the invention, $R^2$ is chosen from:
i) —$OR^6$; or
ii) —$NR^{7a}R^{7b}$;
wherein $R^6$ is hydrogen or $C_1$-$C_4$ linear, branched, or cyclic alkyl; and $R^{7a}$ and $R^{7b}$) are each independently chosen from:
i) hydrogen;
ii) $C_1$-$C_4$ linear, branched, or cyclic alkyl; or
iii) $R^{7a}$ and $R^{7b}$ can be taken together to form a ring having from 3 to 7 atoms.

In certain favored aspects of the invention the $R^2$ units are hydroxyl (—OH) wherein the compounds are carboxylic acids, or may also be present in the form of a salt as the corresponding hydroxyl/carboxylate anion, i.e. R2 can be a —$O^-$ unit, so as to form a compound having a carboxylate group, as shown below.

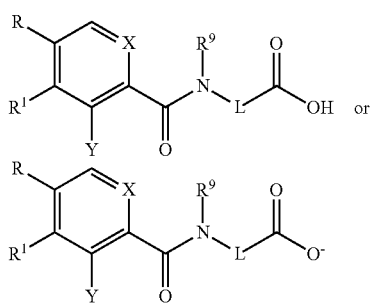

wherein R, $R^1$, $R^2$, X, Y, L, and $R^9$ can be independently chosen in any manner as otherwise taught herein with respect to the compounds of Formula (I).

Another example of $R^2$ includes compounds wherein $R^6$ is $C_1$-$C_4$ linear, branched, or cyclic alkyl providing $R^2$ units which are alkoxy wherein the compounds formed are organic esters having $C_1$-$C_4$ linear, branched, or cyclic alkyl groups. Non-limiting examples of $R^2$ units are:
i) —$OCH_3$;
ii) —$OCH_2CH_3$; and
iii) —$OCH_2CH_2CH_3$.

Yet further examples of $R^2$ units include compounds wherein $R^2$ has the formula —$NR^{7a}R^{7b}$; and $R^{7a}$ and $R^{7b}$ are each independently chosen from:
i) hydrogen; and
ii) $C_1$-$C_4$ linear, branched, or cyclic alkyl.

Non-limiting examples of $R^2$ units include:
i) —$NH_2$;
ii) —$NHCH_3$;
iii) —$N(CH_3)_2$;
iv) —$NH(CH_2CH_3)$;
v) —$N(CH_2CH_3)_2$;
vi) —$N(CH_3)(CH_2CH_3)$.
vii) —$NH(CH_2CH_2CH_3)$;
viii) —$N(CH_2CH_2CH_3)_2$;
ix) —$NH[CH(CH_3)_2]$;
x) —$N[CH(CH_3)_2]_2$;
xi) —$N(CH_2CH_2CH_3)[CH(CH_3)_2]$; and
xii) —NH(cyclopropyl).

A yet further example of $R^2$ units includes compounds wherein $R^2$ has the formula —$NR^{7a}R^{7b}$; and $R^{7a}$ and $R^{7b}$ are taken together to form a ring having from 3 to 7 atoms, wherein the non-limiting examples of $R^2$ units include aziridin-1-yl, axetidin-1-yl, pyrolidin-1-yl, piperidin-1-yl, piperazin-1-yl, and morpholin-4-yl.

In connection with the compounds of Formula (I), L is a unit that links the nitrogen atom of the carboxyamide group to the neighboring carbonyl group. L is typically a $C_1$-$C_6$ or $C_1$-$C_4$ organic linking unit. In some embodiments, L comprises a one or more optionally substituted methylene units having the formula:

wherein $R^{8a}$ and $R^{8b}$ are each independently hydrogen, $C_1$-$C_6$ linear or branched alkyl, or phenyl; and the index y is from 1 to 4.

An example of L units includes units wherein $R^{8a}$ and $R^{8b}$ are both hydrogen and the index n is equal to 1, the L unit has the formula:

and are referred to herein as methylene linking units, so as to form compounds having the structure shown below:

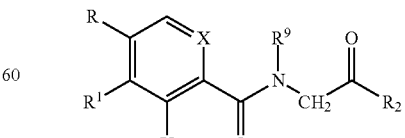

wherein R, $R^1$, $R^2$, X, Y, and $R^9$ can be independently chosen in any manner as otherwise taught herein with respect to the compounds of Formula (I).

Another example of L units includes units wherein $R^{8a}$ and $R^{8b}$ are each hydrogen or methyl and the index n is equal to 1, these units having the formula:

—CH(CH$_3$)— or —C(CH$_3$)$_2$—.

A further example of L units includes units wherein all $R^{8a}$ and $R^{8b}$ units are hydrogen and the index n is equal to 2, these units having the formula:

—CH$_2$CH$_2$— and are referred to herein as ethylene linking units.

In connection with the compounds of Formula I, the $R^9$ substituent for the amide nitrogen atom can be hydrogen or a $C_1$-$C_4$ organic substituent, such as a $C_1$-$C_4$ alkyl group, such as methyl, or a $C_1$-$C_4$ haloalkyl, such as a trifluoromethyl group.

The compounds of Formula (I) can be organized into several categories for the strictly non-limiting purpose of describing alternatives for synthetic strategies for the preparation of subgenera of compounds within the scope of Formula (I) that are not expressly exemplified herein. This mental organization into categories does not imply anything with respect to increased or decreased biological efficacy with respect to any of the compounds or compositions of matter described herein.

One such subgenus of the compounds of Formula (I) relates to compounds having the formula:

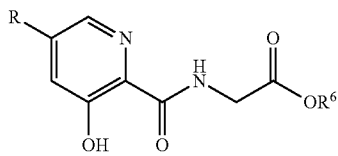

which can be more specifically described by methyl ester compounds having the formula:

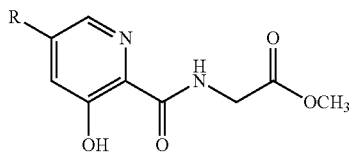

wherein R units can be substituted or unsubstituted phenyl, non-limiting examples of which are described in Table I herein below.

TABLE I

| No. | R |
| --- | --- |
| 1 | 2-fluorophenyl |
| 2 | 3-fluorophenyl |
| 3 | 4-fluorophenyl |
| 4 | 2-chlorophenyl |
| 5 | 3-chlorophenyl |
| 6 | 4-chlorophenyl |
| 7 | 2-cyanophenyl |
| 8 | 3-cyanophenyl |
| 9 | 4-cyanophenyl |
| 10 | 2-methylphenyl |
| 11 | 3-methylphenyl |
| 12 | 4-methylphenyl |
| 13 | 2-ethylphenyl |
| 14 | 3-ethylphenyl |
| 15 | 4-ethylphenyl |

TABLE I-continued

| No. | R |
| --- | --- |
| 16 | 2-methoxyphenyl |
| 17 | 3-methoxyphenyl |
| 18 | 4-methoxyphenyl |
| 19 | 2-ethoxyphenyl |
| 20 | 3-ethoxyphenyl |
| 21 | 4-ethoxyphenyl |
| 22 | 2-iso-propoxyphenyl |
| 23 | 3-iso-propoxyphenyl |
| 24 | 4-iso-propoxyphenyl |
| 25 | 2-carbamoylphenyl |
| 26 | 3-carbamoylphenyl |
| 27 | 4-carbamoylphenyl |
| 28 | 2-(aziridine-1-carbonyl)phenyl |
| 29 | 3-(aziridine-1-carbonyl)phenyl |
| 30 | 4-(aziridine-1-carbonyl)phenyl |
| 31 | 2-(azetidine-1-carbonyl)phenyl |
| 32 | 3-(azetidine-1-carbonyl)phenyl |
| 33 | 4-(azetidine-1-carbonyl)phenyl |
| 34 | 2-(pyrrolidine-1-carbonyl)phenyl |
| 35 | 3-(pyrrolidine-1-carbonyl)phenyl |
| 36 | 4-(pyrrolidine-1-carbonyl)phenyl |
| 37 | 2-(piperidine-1-carbonyl)phenyl |
| 38 | 3-(piperidine-1-carbonyl)phenyl |
| 39 | 4-(piperidine-1-carbonyl)phenyl |
| 40 | 2-(acetylamino)phenyl |
| 41 | 3-(acetylamino)phenyl |
| 42 | 4-(acetylamino)phenyl |
| 43 | 2-(ethanecarbonylamino)phenyl |
| 44 | 3-(ethanecarbonylamino)phenyl |
| 45 | 4-(ethanecarbonylamino)phenyl |
| 46 | 2-(cyclopropanecarbonylamino)phenyl |
| 47 | 3-(cyclopropanecarbonylamino)phenyl |
| 48 | 4-(cyclopropanecarbonylamino)phenyl |

Such compounds can be prepared by the procedure outlined in Scheme I and further described in Example 1 herein below.

Scheme I

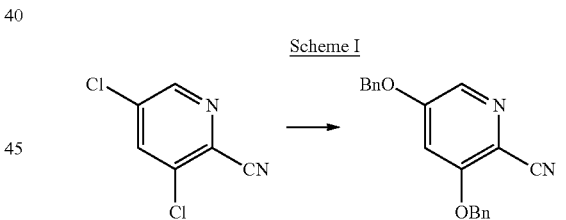

Reagents and conditions: (a) C$_6$H$_5$OH, NaH, THF; microwave 190° C., 5 hr.

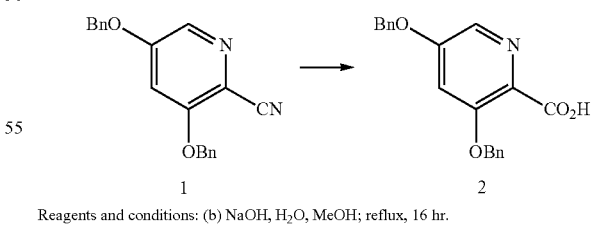

Reagents and conditions: (b) NaOH, H$_2$O, MeOH; reflux, 16 hr.

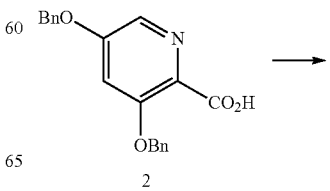

15

-continued

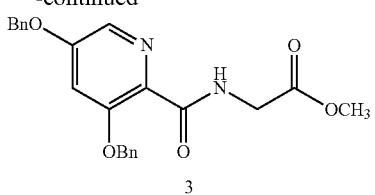

Reagents and conditions: (c) GlyOMe•HCl, EDCI, HOBt, DMF; 0° C. to rt, 3 days.

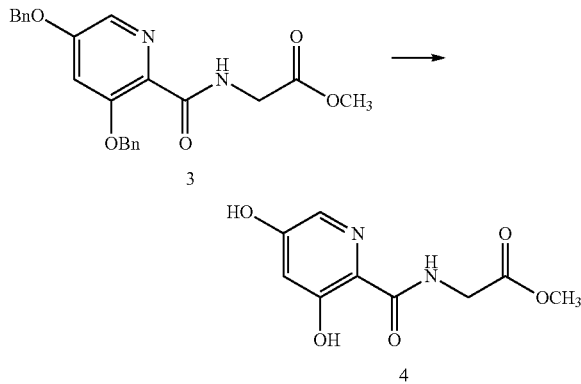

Reagents and conditions: (d) H$_2$: Pd/C, MeOH, rt, 16 hr.

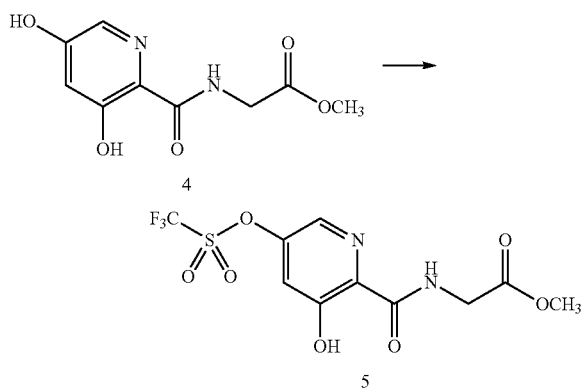

Reagents and conditions: (e) (CF$_3$SO$_2$)$_2$NC$_6$H$_5$, MeOH, rt, 16 hr.

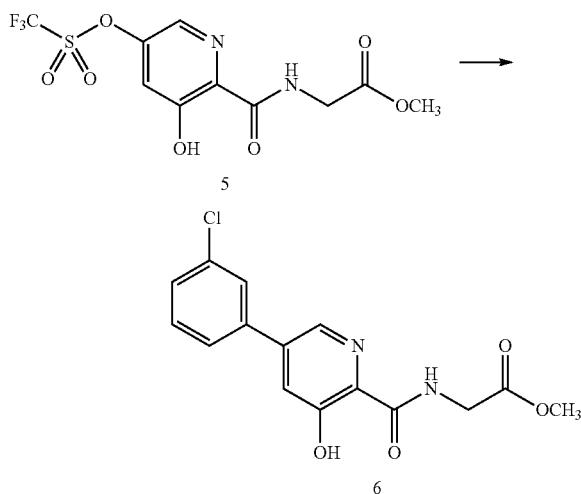

Reagents and conditions: (f) 3-chlorophenylboronic acid, Pd(dppf)Cl$_2$, K$_3$PO$_4$, dioxane; 85° C., 16 hr.

16

Example 1

{[5-(3-Chloro-phenyl)-3-hydroxy-pyridine-2-carbonyl]-amino} acetic acid methyl ester (6)

Preparation of 3,5-bis-benzyloxy-pyridine-2-carbonitrile (1): To an 80 mL microwave pressure vessel is charged dry THF (30 mL) and benzyl alcohol (6.32 mL, 61.1 mmol). The solution is cooled to 0° C. and sodium hydride (2.44 g of a 60% dispersion in mineral oil, 61.1 mmol) is added in portions. The reaction mixture is gradually allowed to warm to room temperature with efficient stirring until the evolution of hydrogen gas ceases. The solution is re-cooled to 0° C. and 3,5-dichloro-2-cyanopyridine (5.00 g, 29.1 mmol) is added, and the solution is transferred to an unfocussed Mars 5 CEM microwave reactor to 190° C., 300 W and held for 5 hours. The reaction mixture is quenched with H$_2$O, concentrated under reduced pressure, diluted with EtOAc and washed with 2M Na$_2$CO$_3$, H$_2$O and saturated aqueous NaCl. The organic layer is dried (MgSO$_4$), filtered and concentrated under reduced pressure to give a brown solid. The crude solid is purified over silica (EtOAc:heptane, gradient 1:1 to 1:0) to afford 8.6 g (94% yield) of the desired compound as an orange solid. $^1$H NMR (400 MHz, CDCl$_3$) δ ppm 7.96 (1H, d, J=2.2 Hz), 7.25-7.37 (10H, m), 6.78 (1H, d, J=2.2 Hz), 5.10 (2H, s), 5.03 (2H, s). HPLC-MS: m/z 317 [M+H]$^+$.

Preparation of 3,5-bis-benzyloxy-pyridine-2-carboxylic acid (2): To a solution of 3,5-bis-benzyloxy-pyridine-2-carbonitrile, 1, (26.0 g, 82.3 mmol) in MeOH (217 mL) is added 30% w/v sodium hydroxide (320 mL) and the reaction mixture is refluxed for 16 hours. The solvent is removed under reduced pressure and the resulting suspension is acidified with conc. HCl until the pH is between 1 and 2. The precipitate that results is collected by filtration, washed with H$_2$O (10 mL) and dried overnight in a vacuum oven to afford 30 g (quantitative) of the desired product as the hydrochloride salt. $^1$H NMR (250 MHz, DMSO-d$_6$) δ ppm 8.02 (1H, d, J=2.4 Hz), 7.29-7.53 (11H, m), 5.96 (1H, br s), 5.28 (4H, s). HPLC-MS: m/z 336 [M+H]$^+$.

Preparation of [(3,5-bis-benzyloxy-pyridine-2-carbonyl)-amino]-acetic acid methyl ester (3): To a solution of 3,5-bis-benzyloxy-pyridine-2-carboxylic acid HCl, 2, (8.06 g, 21.7 mmol) in DMF (100 mL) at 0° C. under N$_2$ is added diisopropylethylamine (11.35 mL, 65.1 mmol), 1-(3-dimethylaminopropyl)-3-ethylcarbodiimide (EDCI) (6.23 g, 32.6 mmol) and 1-hydroxybenzotriazole (HOBt) (0.294 g, 2.2 mmol). The solution is stirred for 5 minutes and glycine methyl ester hydrochloride (4.09 g, 32.6 mmol) is added. The reaction is allowed to warm slowly to room temperature and stirred 3 days. The reaction volume is partially concentrated under reduced pressure then diluted with EtOAc and washed with saturated aqueous NaHCO$_3$ and saturated aqueous NaCl. The organic layer is dried (MgSO$_4$), filtered and concentrated under reduced pressure to afford a yellow oil that is purified over silica (EtOAc:heptane gradient 1:1 to 1:0) to afford 3.5 g (40% yield) of the desired product as a yellow oil. $^1$H NMR (400 MHz, CDCl$_3$) δ ppm 8.12 (1H, t, J=4.9 Hz), 7.95 (1H, d, J=1.8 Hz), 7.38-7.44 (2H, m), 7.22-7.35 (8H, m), 6.85 (1H, d, J=2.6 Hz), 5.14 (2H, s), 5.03 (2H, s), 4.18 (2H, d, J=5.5 Hz), 3.69 (3H, s). HPLC-MS: m/z 407 [M+H]$^+$.

Preparation of [(3,5-dihydroxy-pyridine-2-carbonyl)-amino]-acetic acid methyl ester (4): To a solution [(3,5-bis-benzyloxy-pyridine-2-carbonyl)-amino]-acetic acid methyl ester (3.50 g, 8.62 mmol) in MeOH (100 mL) is added 10% Pd/C (0.350 g, 0.862 mmol) and the reaction mixture stirred under an atmosphere of H$_2$ at room temperature for 16 hours. The suspension is filtered through Celite™ and the filtrate concentrated under reduced pressure. The crude material is purified over silica (MeOH:CH$_2$Cl$_2$ gradient 1% to 5%) to afford 1.95 g (quantitative yield) of the desired compound as an off-white solid. $^1$H NMR (250 MHz, MeOD) δ ppm 7.62 (1H, d, J=2.4 Hz), 6.53 (1H, d, J=2.4 Hz), 4.04 (2H, s), 3.64 (3H, s). HPLC-MS: m/z 227 [M+H]$^+$.

Preparation of [(3-hydroxy-5-trifluoromethanesulfonyloxy-pyridine-2-carbonyl)-amino]-acetic acid methyl ester (5): To a solution of [(3,5-dihydroxy-pyridine-2-carbonyl)-amino]-acetic acid methyl ester, 4, (1.95 g, 8.62 mmol) in MeOH (60 mL) is added diisopropylethylamine (DIPEA) (1.62 mL, 9.3 mmol). The mixture is cooled to 0° C. and N-phenyl trifluoromethansulfonimide (3.32 g, 9.3 mmol) is added. The resulting solution is slowly warmed to room temperature and stirred for an additional 16 hours. The solvent is removed under reduced pressure and the crude material is purified over silica (EtOAc:hexane 1:4) to afford 2.27 g (73% yield) of the desired product as an off-white solid. $^1$H NMR (400 MHz, CDCl$_3$) δ ppm 12.17 (1H, s), 8.27 (1H, t, J=5.5 Hz), 8.08 (1H, d, J=2.2 Hz), 7.28 (1H, d, J=2.2 Hz), 4.24 (2H, d, J=5.5 Hz), 3.82 (3H, s). HPLC-MS: m/z 359 [M+H]$^+$.

Preparation of {[5-(3-chloro-phenyl)-3-hydroxy-pyridine-2-carbonyl]-amino}-acetic acid methyl ester (6): To a degassed solution of [(3-hydroxy-5-trifluoromethane-sulfonyloxy-pyridine-2-carbonyl)-amino]-acetic acid methyl ester, 5, (0.30 g, 0.84 mmol) in 1,4-dioxane (10 mL) at room temperature under N$_2$ is added 3-chlorophenylboronic acid (0.196 g, 1.26 mmol), Pd(dppf)Cl$_2$ (0.068 g, 0.0084 mmol) and K$_3$PO$_4$ (0.195 g, 0.92 mmol). The resulting suspension is heated in a sealed tube at 85° C. for 16 hours. After this time, the mixture is cooled to room temperature and concentrated under reduced pressure. The residue is then treated with 1M HCl (1 mL) and diluted with EtOAc. The organic layer is separated, washed with H$_2$O, saturated aqueous NaCl and concentrated under reduced pressure. The crude material is purified over silica (EtOAc:heptane 3:7). The resulting solid can be crystallized from EtOAc/heptane to afford 0.143 g (53% yield) of the desired compound as a colorless solid. $^1$H NMR (400 MHz, CDCl$_3$) δ ppm 11.77 (1H, s), 8.36 (1H, t, J=5.7 Hz), 8.24 (1H, d, J=1.8 Hz), 7.50-7.53 (1H, m), 7.39-7.42 (2H, m), 7.34-7.37 (2H, m), 4.20 (2H, d, J=5.9 Hz), 3.76 (3H, s). HPLC-MS: m/z.

The procedure outlined in Scheme I can be modified by substituting in step (f) other reagents for 3-chlorophenylboronic acid. Non-limiting examples include 4-chlorophenylboronic acid, 2-chlorophenylboronic acid, 2-fluorophenylboronic acid, 3-fluorophenylboronic acid, 4-fluorophenylboronic acid, 2-methylphenylboronic acid, 3-methylphenylboronic acid, and 4-methylphenylboronic acid.

The following are further non-limiting examples of compounds encompassed within first aspect of Category I of the present disclosure.

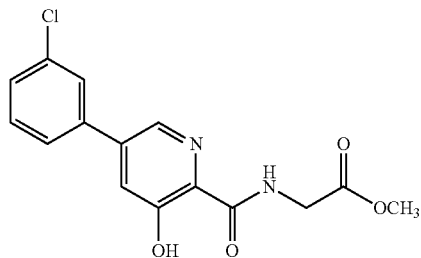 [SMILES: COC(=O)CNC(=O)c1ncc(-c2cccc(Cl)c2)cc1O]

{[5-(4-Chlorophenyl)-3-hydroxy-pyridine-2-carbonyl]-amino}-acetic acid methyl ester: $^1$H NMR (400 MHz, CDCl$_3$) δ ppm 11.77 (1H, s), 8.36 (1H, t, J=5.5 Hz), 8.23 (1H, d, J=1.8 Hz), 7.44-7.49 (2H, m), 7.38-7.42 (3H, m), 4.20 (2H, d, J=5.9 Hz), 3.76 (3H, s). HPLC-MS: m/z 321 [M+H]$^+$.

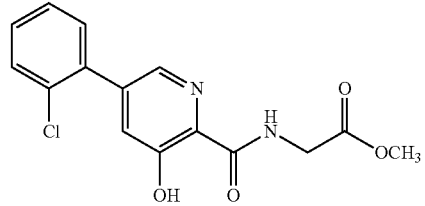 [SMILES: COC(=O)CNC(=O)c1ncc(-c2ccccc2Cl)cc1O]

{[5-(2-Chlorophenyl)-3-hydroxy-pyridine-2-carbonyl]-amino}-acetic acid methyl ester: $^1$H NMR (400 MHz, MeOD) δ ppm 8.10 (1H, d, J=1.8 Hz), 7.46 (1H, dd, J=7.5, 2.4 Hz), 7.30-7.35 (4H, m), 4.11 (2H, s), 3.68 (3H, s). HPLC-MS: m/z 321 [M+H]$^+$.

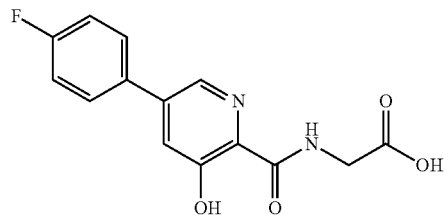 [SMILES: O=C(O)CNC(=O)c1ncc(-c2ccc(F)cc2)cc1O]

{[5-(4-Fluorophenyl)-3-hydroxy-pyridine-2-carbonyl]-amino}-acetic acid methyl ester: $^1$H NMR (250 MHz, CDCl$_3$) δ ppm 11.88 (1H, s), 8.48 (1H, t, J=5.6 Hz), 8.33 (1H, d, J=2.1 Hz), 7.55-7.65 (2H, m), 7.49 (1H, d, J=2.1 Hz), 7.17-7.27 (2H, m), 4.28-4.32 (2H, m), 3.86 (3H, s). HPLC-MS: m/z 305 [M+H]$^+$.

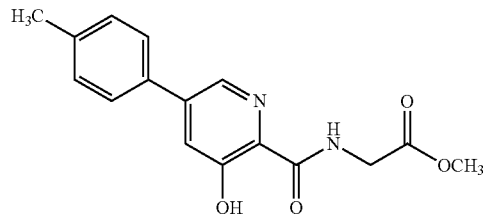 [SMILES: COC(=O)CNC(=O)c1ncc(-c2ccc(C)cc2)cc1O]

[(3-Hydroxy-5-(4-methylphenyl)-pyridine-2-carbonyl)-amino]-acetic acid methyl ester: $^1$H NMR (400 MHz, CDCl$_3$) δ ppm 11.72 (1H, s), 8.36 (1H, t, J=5.1 Hz), 8.26 (1H, d, J=1.8 Hz), 7.43 (2H, d, J=8.0 Hz), 7.40 (1H, d, J=1.8 Hz), 7.23 (2H, d, J=8.1 Hz), 4.19 (2H, d, J=5.9 Hz), 3.75 (3H, s), 2.35 (3H, s). HPLC-MS: m/z 301 [M+H]$^+$.

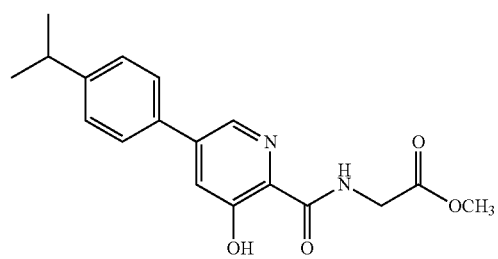 [SMILES: COC(=O)CNC(=O)c1ncc(-c2ccc(C(C)C)cc2)cc1O]

{[3-Hydroxy-5-(4-isopropylphenyl)-pyridine-2-carbonyl]-amino}-acetic acid methyl ester: ¹H NMR (250 MHz, CDCl₃) δ ppm 11.88 (1H, s), 8.54 (1H, t, J=5.6 Hz), 8.38 (1H, d, J=1.8 Hz), 7.55-7.60 (2H, m), 7.54 (1H, d, J=2.1 Hz), 7.36-7.42 (2H, m), 4.30 (2H, d, J=5.8 Hz), 3.85 (3H, s), 2.93-3.07 (1H, m), 1.33 (6H, d, J=7.0 Hz). HPLC-MS: m/z 329 [M+H]⁺.

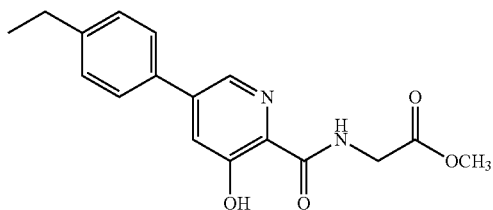 [SMILES: CCc1ccc(-c2cnc(C(=O)NCC(=O)OC)c(O)c2)cc1]

{[5-(4-Ethylphenyl)-3-hydroxy-pyridine-2-carbonyl]-amino}-acetic acid methyl ester: ¹H NMR (250 MHz, CDCl₃) δ ppm 11.86 (1H, s), 8.51 (1H, t, J=5.8 Hz), 8.37 (1H, d, J=1.8 Hz), 7.56 (2H, d, J=8.2 Hz), 7.53 (1H, d, J=1.8 Hz), 7.36 (2H, d, J=8.5 Hz), 4.30 (2H, d, J=5.8 Hz), 3.85 (3H, s), 2.75 (2H, q, J=7.6 Hz), 1.31 (3H, t, J=7.6 Hz). HPLC-MS: m/z 315 [M+H]⁺.

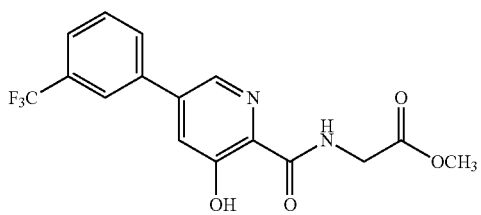

{[3-Hydroxy-5-(3-trifluoromethyl-phenyl)-pyridine-2-carbonyl]-amino}-acetic acid methyl ester: ¹H NMR (250 MHz, CDCl₃) δ ppm 11.91 (1H, s), 8.48 (1H, t, J=6.1 Hz), 8.37 (1H, d, J=1.8 Hz), 7.60-7.92 (4H, m), 7.54 (1H, d, J=2.1 Hz), 4.31 (2H, d, J=5.8 Hz), 3.86 (3H, s). HPLC-MS: m/z 355 [M+H]⁺.

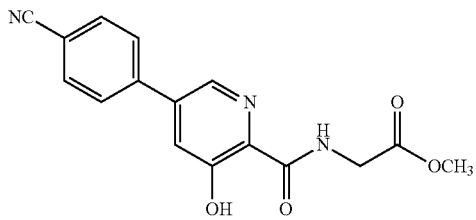 [SMILES: COC(=O)CNC(=O)c1ncc(-c2ccc(C#N)cc2)cc1O]

{[5-(4-Cyanophenyl)-3-hydroxy-pyridine-2-carbonyl]-amino}-acetic acid methyl ester: ¹H NMR (400 MHz, CDCl₃) δ ppm 11.83 (1H, s), 8.36 (1H, t, J=5.12 Hz), 8.26 (1H, d, J=1.83 Hz), 7.70-7.75 (2H, m), 7.62-7.66 (2H, m), 7.43 (1H, d, J=1.83 Hz), 4.21 (2H, d, J=5.49 Hz), 3.76 (3H, s). HPLC-MS: m/z 312 [M+H]⁺.

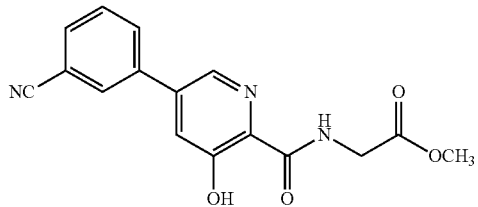 [SMILES: COC(=O)CNC(=O)c1ncc(-c2cccc(C#N)c2)cc1O]

{[5-(3-Cyanophenyl)-3-hydroxy-pyridine-2-carbonyl]-amino}-acetic acid methyl ester: ¹H NMR (250 MHz, DMSO-d₆) δ ppm 12.30 (1H, s), 9.51 (1H, t, J=5.8 Hz), 8.55 (1H, d, J=1.8 Hz), 8.32 (1H, s), 8.14 (1H, d, J=8.5 Hz), 7.89 (1H, d, J=7.8 Hz), 7.81 (1H, d, J=1.9 Hz), 7.68 (1H, t, J=7.8 Hz), 4.06 (2H, d, J=6.1 Hz), 3.63 (3H, s). HPLC-MS: m/z 312 [M+H]⁺.

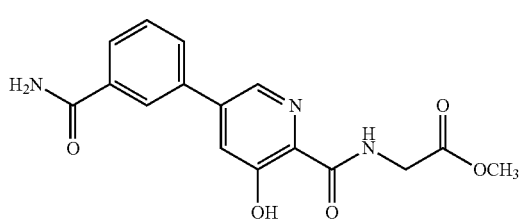 [SMILES: COC(=O)CNC(=O)c1ncc(-c2cccc(C(N)=O)c2)cc1O]

{[5-(3-Carbamoylphenyl)-3-hydroxy-pyridine-2-carbonyl]-amino}-acetic acid methyl ester: ¹H NMR (250 MHz, DMSO-d₆) δ ppm 12.30 (1H, s), 9.54 (1H, t, J=6.0 Hz), 8.61 (1H, d, J=1.8 Hz), 8.29 (1H, s), 8.18 (1H, br s), 7.98 (2H, t, J=8.1 Hz), 7.84 (1H, d, J=1.7 Hz), 7.62 (1H, t, J=7.8 Hz), 7.53 (1H, br s), 4.12 (2H, d, J=6.0 Hz), 3.69 (3H, s). HPLC-MS: m/z 330 [M+H]⁺.

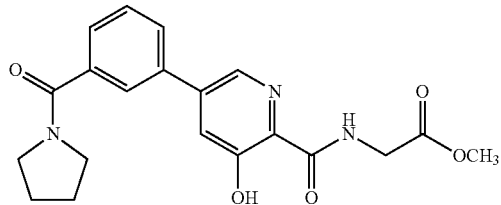 [SMILES: COC(=O)CNC(=O)c1ncc(-c2cccc(C(=O)N3CCCC3)c2)cc1O]

({3-Hydroxy-5-[3-(pyrrolidine-1-carbonyl)-phenyl]-pyridine-2-carbonyl}-amino)-acetic acid methyl ester: ¹H NMR (250 MHz, CDCl₃) δ ppm 11.80 (1H, s), 8.44 (1H, t, J=5.3 Hz), 8.35 (1H, s), 7.77 (1H, s), 7.47-7.70 (4H, m), 4.28 (2H, d, J=5.7 Hz), 3.83 (3H, s), 3.64-3.76 (2H, m), 3.42-3.55 (2H, m), 1.84-2.07 (4H, m). HPLC-MS: m/z 384 [M+H]⁺.

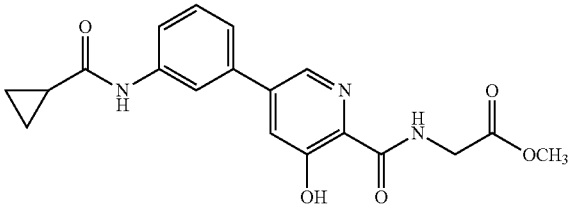 [SMILES: COC(=O)CNC(=O)c1ncc(-c2cccc(NC(=O)C3CC3)c2)cc1O]

({5-[3-(Cyclopropanecarbonyl-amino)-phenyl]-3-hydroxy-pyridine-2-carbonyl}-amino)-acetic acid methyl ester: ¹H NMR (250 MHz, CDCl₃) δ ppm 11.80 (1H, s), 8.45

(1H, br s), 8.29 (1H, s), 7.65-7.88 (2H, m), 7.29-7.60 (4H, m), 4.18-4.31 (3H, m), 3.83 (3H, s), 1.05-1.17 (2H, m), 0.81-0.98 (2H, m). HPLC-MS: m/z 370 [M+H]$^+$.

The following heteroaryl substituted phenyl compound can be prepared from {[5-(3-cyano-phenyl)-3-hydroxy-pyridine-2-carbonyl]-amino}acetic acid methyl ester by treatment with trimethylsilyl azide and di-butyl tin oxide in DME and heating the mixture to 140° C., 150 W, 200 psi in a microwave reactor.

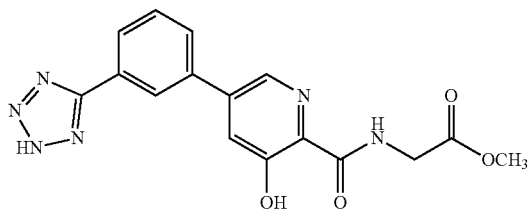 [SMILES: COC(=O)CNC(=O)c1ncc(-c2cccc(-c3nn[nH]n3)c2)cc1O]

({3-Hydroxy-5-[3-(2H-tetrazol-5-yl)-phenyl]-pyridine-2-carbonyl}-amino)-acetic acid methyl ester: $^1$H NMR (400 MHz, DMSO-d$_6$) δ ppm 12.33 (1H, s), 9.55 (1H, t, J=6.1 Hz), 8.62 (1H, d, J=1.8 Hz), 8.43 (1H, s), 8.14 (1H, d, J=7.9 Hz), 8.05 (1H, d, J=8.1 Hz), 7.83 (1H, d, J=1.9 Hz), 7.76 (1H, t, J=7.8 Hz), 4.12 (2H, d, J=6.1 Hz), 3.69 (3H, s). HPLC-MS: m/z 355 [M+H]$^+$.

For the purposes of describing synthetic methods, another mental subgenus of the compounds of Formula (I) have the formula:

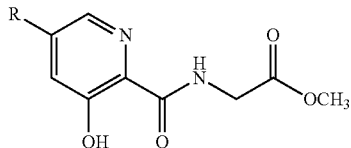

wherein R units which are substituted or unsubstituted heteroaryl, non-limiting examples of which are described in Table II herein below.

TABLE II

| No. | R |
|---|---|
| 49 | pyridin-2-yl |
| 50 | pyridin-3-yl |
| 51 | pyridin-4-yl |
| 52 | pyrimidin-2-yl |
| 53 | pyrimidin-4-yl |
| 54 | pyrimidin-5-yl |
| 55 | isoquinolin-1-yl |
| 56 | isoquinolin-3-yl |
| 57 | isoquinolin-4-yl |
| 58 | thiazol-2-yl |
| 59 | thiazol-4-yl |
| 60 | 1,2,3,4-tetrazol-5-yl |
| 61 | [1,2,4]triazol-5-yl |
| 62 | imidazol-2-yl |
| 63 | furan-2-yl |
| 64 | furan-3-yl |
| 65 | thiophene-2-yl |
| 66 | thiophene-3-yl |

The compounds encompassed within the compounds described immediately above can be prepared by the procedure outlined in Scheme I and described in Example 1 herein above.

The procedure outlined in Scheme I can be modified by substituting in step (f) other reagents for 3-chlorophenylboronic acid. Non-limiting examples of substitutes include 3-(thiazol-2-yl)phenylboronic acid, 3-(thiazol-4-yl)phenylboronic acid, 4-(thiazol-2-yl)phenylboronic acid, 4-(thiazol-4-yl)phenylboronic acid, 3-(imidazol-2-yl)phenylboronic acid, 4-(imidazol-2-yl)phenylboronic acid, 3-(furan-2-yl)phenylboronic acid, 3-(furan-3-yl)phenylboronic acid, and 3-(thiophene-2-yl)phenylboronic acid.

The following are non-limiting examples of such compounds.

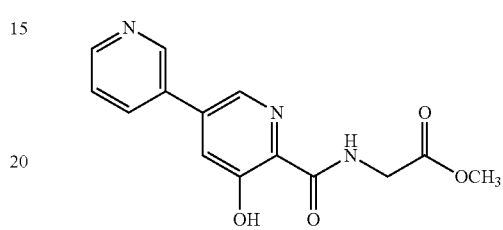

[(5-Hydroxy-[3,3']bipyridinyl-6-carbonyl)-amino]-acetic acid methyl ester $^1$H NMR (250 MHz, CDCl$_3$) δ ppm 11.80 (1H, s), 8.87 (1H, d, J=1.7 Hz), 8.70 (1H, dd, J=4.8, 1.6 Hz), 8.45 (1H, t, J=5.8 Hz), 8.33 (1H, d, J=1.9 Hz), 7.91 (1H, ddd, J=8.0, 2.3, 1.7 Hz), 7.51 (1H, d, J=1.9 Hz), 7.45 (1H, ddd, J=7.9, 4.8, 0.7 Hz), 4.28 (2H, d, J=5.8 Hz), 3.83 (3H, s). HPLC-MS: m/z 288 [M+H]$^+$.

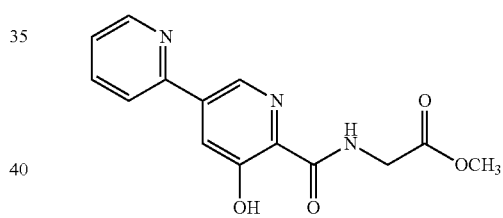

[(5'-Hydroxy-[2,3']bipyridinyl-6'-carbonyl)-amino]-acetic acid methyl ester: $^1$H NMR (250 MHz, CDCl$_3$) δ ppm 8.70-8.79 (2H, m), 8.49 (1H, t, J=5.8 Hz), 7.72-7.92 (3H, m), 7.31-7.39 (1H, m), 4.28 (2H, d, J=5.8 Hz), 3.83 (3H, s). HPLC-MS: m/z 288 [M+H]$^+$.

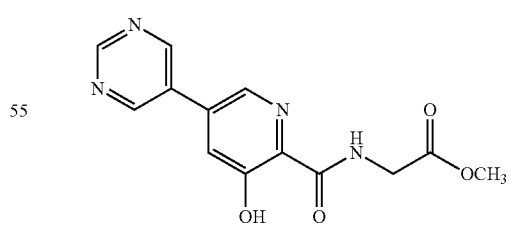

[(3-Hydroxy-5-pyrimidin-5-yl-pyridine-2-carbonyl)-amino]-acetic acid methyl ester: $^1$H NMR (250 MHz, CDCl$_3$) δ ppm 11.90 (1H, s), 9.32 (1H, s), 9.00 (2H, s), 8.45 (1H, br s), 8.34 (1H, d, J=1.8 Hz), 7.53 (1H, d, J=1.8 Hz), 4.29 (2H, d, J=5.7 Hz), 3.84 (3H, s). HPLC-MS: m/z 289 [M+H]$^+$.

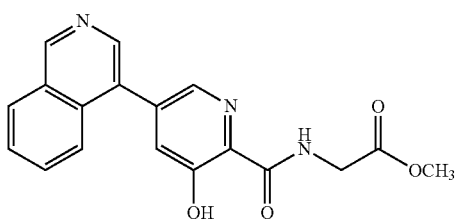 [SMILES: COC(=O)CNC(=O)c1ncc(-c2cncc3ccccc23)cc1O]

[(3-Hydroxy-5-isoquinolin-4-yl-pyridine-2-carbonyl)-amino]-acetic acid methyl ester: ¹H NMR (250 MHz, CDCl₃) δ ppm 11.80 (1H, s), 9.38 (1H, br s), 8.51 (2H, t, J=5.7 Hz), 8.27 (1H, s), 8.13 (1H, d, J=7.2 Hz), 7.67-7.93 (3H, m), 7.51 (1H, s), 4.31 (2H, d, J=5.7 Hz), 3.85 (3H, s). HPLC-MS: m/z 338 [M+H]⁺.

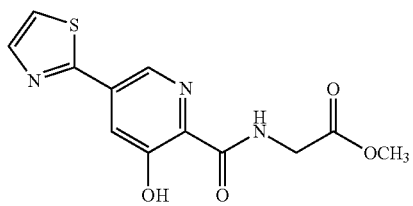 [SMILES: COC(=O)CNC(=O)c1ncc(-c2nccs2)cc1O]

[(3-Hydroxy-5-thiazol-2-yl-pyridine-2-carbonyl)-amino]-acetic acid methyl ester: ¹H NMR (250 MHz, CDCl₃) δ ppm 11.80 (1H, s), 8.67 (1H, d, J=1.8 Hz), 8.39 (1H, br s), 7.93 (1H, d, J=3.3 Hz), 7.78 (1H, d, J=1.7 Hz), 7.43 (1H, d, J=3.2 Hz), 4.22 (2H, d, J=5.8 Hz), 3.78 (3H, s). HPLC-MS: m/z 294 [M+H]⁺.

Another mental subgenus of the compounds of Formula (I) encompasses compounds having the formula:

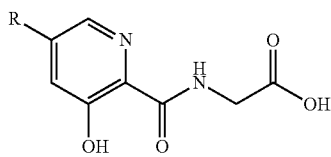

wherein R units which are substituted or unsubstituted phenyl, non-limiting examples of which are described in Table III herein below.

TABLE III

| No. | R |
|-----|---|
| 67 | 2-fluorophenyl |
| 68 | 3-fluorophenyl |
| 69 | 4-fluorophenyl |
| 70 | 2-chlorophenyl |
| 71 | 3-chlorophenyl |
| 72 | 4-chlorophenyl |
| 73 | 2-cyanophenyl |
| 74 | 3-cyanophenyl |
| 75 | 4-cyanophenyl |
| 76 | 2-methylphenyl |
| 77 | 3-methylphenyl |
| 78 | 4-methylphenyl |
| 79 | 2-ethylphenyl |
| 80 | 3-ethylphenyl |
| 81 | 4-ethylphenyl |
| 82 | 2-methoxyphenyl |
| 83 | 3-methoxyphenyl |

TABLE III-continued

| No. | R |
|-----|---|
| 84 | 4-methoxyphenyl |
| 85 | 2-ethoxyphenyl |
| 86 | 3-ethoxyphenyl |
| 87 | 4-ethoxyphenyl |
| 88 | 2-iso-propoxyphenyl |
| 89 | 3-iso-propoxyphenyl |
| 90 | 4-iso-propoxyphenyl |
| 91 | 2-carbamoylphenyl |
| 92 | 3-carbamoylphenyl |
| 93 | 4-carbamoylphenyl |
| 94 | 2-(aziridine-1-carbonyl)phenyl |
| 95 | 3-(aziridine-1-carbonyl)phenyl |
| 96 | 4-(aziridine-1-carbonyl)phenyl |
| 97 | 2-(azetidine-1-carbonyl)phenyl |
| 98 | 3-(azetidine-1-carbonyl)phenyl |
| 99 | 4-(azetidine-1-carbonyl)phenyl |
| 100 | 2-(pyrrolidine-1-carbonyl)phenyl |
| 101 | 3-(pyrrolidine-1-carbonyl)phenyl |
| 102 | 4-(pyrrolidine-1-carbonyl)phenyl |
| 103 | 2-(piperidine-1-carbonyl)phenyl |
| 104 | 3-(piperidine-1-carbonyl)phenyl |
| 105 | 4-(piperidine-1-carbonyl)phenyl |
| 106 | 2-(acetylamino)phenyl |
| 107 | 3-(acetylamino)phenyl |
| 108 | 4-(acetylamino)phenyl |
| 109 | 2-(ethanecarbonylamino)phenyl |
| 110 | 3-(ethanecarbonylamino)phenyl |
| 111 | 4-(ethanecarbonylamino)phenyl |
| 112 | 2-(cyclopropanecarbonylamino)phenyl |
| 113 | 3-(cyclopropanecarbonylamino)phenyl |
| 114 | 4-(cyclopropanecarbonylamino)phenyl |

The compounds described immediately above can be prepared by the procedure outlined in Scheme II and described in Example 2.

Scheme II

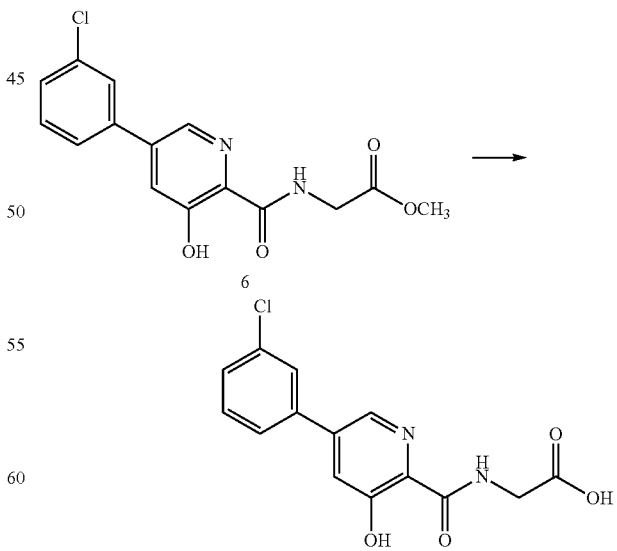

Reagents and conditions: (a) NaOH, H₂O/THF; rt, 1 hr.

Example 2

{[5-(3-Chlorophenyl)-3-hydroxypyridine-2-carbonyl]amino}-acetic acid (7)

Preparation of {[5-(3-chlorophenyl)-3-hydroxypyridine-2-carbonyl]amino}-acetic acid (7): To a solution of {[5-(3-chloro-phenyl)-3-hydroxy-pyridine-2-carbonyl]-amino}-acetic acid methyl ester, 6, (0.163 g, 0.509 mmol) in THF (5 mL) is added 1M NaOH (1.5 ml, 1.27 mmol) and the reaction mixture stirred at room temperature for 1 hour. The solution is acidified using 1M HCl (3 mL), the solvent removed under reduced pressure and the resulting solid suspended in CHCl$_3$:iso-propanol (1:1), filtered and the filtrate dried (MgSO$_4$), filtered and re-concentrated under reduced pressure. The crude material is triturated with a small amount of MeOH to afford 0.10 g (64% yield) of the desired product as a colorless solid. $^1$H NMR (400 MHz, MeOD) δ ppm 8.31 (1H, d, J=1.8 Hz), 7.47 (2H, d, J=1.8 Hz), 7.30-7.65 (4H, m), 4.07 (2H, s). HPLC-MS: m/z 307 [M+H]$^+$.

The following are further non-limiting examples.

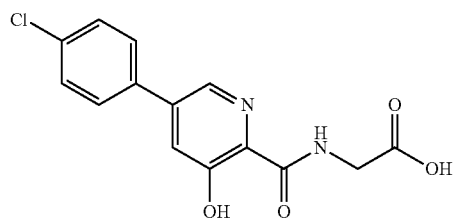 [SMILES: O=C(O)CNC(=O)c1ncc(-c2ccc(Cl)cc2)cc1O]

{[5-(4-Chlorophenyl)-3-hydroxypyridine-2-carbonyl]amino}-acetic acid: $^1$H NMR (400 MHz, MeOD) δ ppm 8.33 (1H, d, J=1.5 Hz), 7.61 (2H, d, J=8.4 Hz), 7.48 (1H, d, J=1.8 Hz), 7.42 (2H, d, J=8.4 Hz), 4.06 (2H, s). HPLC-MS: m/z 307 [M+H]$^+$.

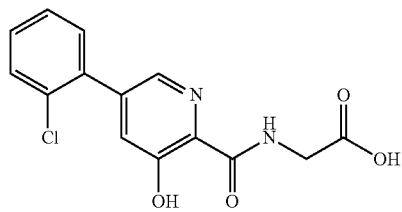 [SMILES: O=C(O)CNC(=O)c1ncc(-c2ccccc2Cl)cc1O]

{[5-(2-Chlorophenyl)-3-hydroxypyridine-2-carbonyl]amino}-acetic acid: $^1$H NMR (400 MHz, MeOD) δ ppm 8.10 (1H, d, J=1.8 Hz), 7.40-7.56 (1H, m), 7.09-7.40 (4H, m), 4.07 (2H, s). HPLC-MS: m/z 307 [M+H]$^+$.

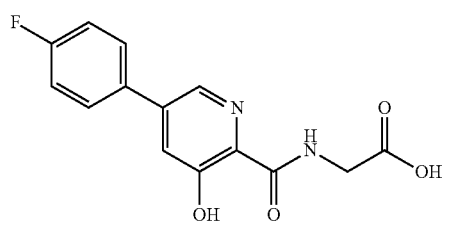

{[5-(4-Fluorophenyl)-3-hydroxypyridine-2-carbonyl]amino}-acetic acid: $^1$H NMR (250 MHz, DMSO-d$_6$) δ ppm 12.39 (1H, br s), 9.38 (1H, t, J=6.2 Hz), 8.53 (1H, d, J=2.1 Hz), 7.91 (2H, dd, J=8.8, 5.5 Hz), 7.74 (1H, d, J=2.1 Hz), 7.38 (2H, t, J=8.8 Hz), 4.02 (2H, d, J=6.4 Hz). HPLC-MS: m/z 291 [M+H]$^+$.

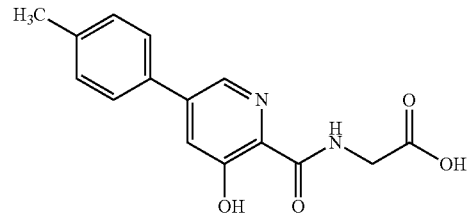 [SMILES: Cc1ccc(-c2cnc(C(=O)NCC(=O)O)c(O)c2)cc1]

[(3-Hydroxy-5-(4-methylphenyl)pyridine-2-carbonyl)amino]-acetic acid: $^1$H NMR (400 MHz, MeOD) δ ppm 8.40 (1H, s), 7.68 (1H, s), 7.53 (2H, d, J=8.42 Hz), 7.26 (2H, d, J=8.05 Hz), 4.10 (2H, s), 2.31 (3H, s). HPLC-MS: m/z 287 [M+H]$^+$.

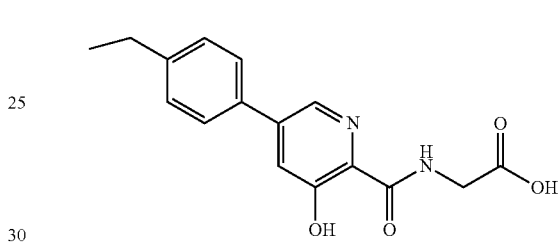

{[5-(4-Ethylphenyl)-3-hydroxypyridine-2-carbonyl]amino}-acetic acid: $^1$H NMR (250 MHz, DMSO-d$_6$) δ ppm 12.40 (1H, s), 9.35 (1H, t, J=6.1 Hz), 8.52 (1H, d, J=2.1 Hz), 7.76 (2H, d, J=8.2 Hz), 7.71 (1H, d, J=1.8 Hz), 7.38 (2H, d, J=8.2 Hz), 4.02 (2H, d, J=6.1 Hz), 2.68 (2H, q, J=7.6 Hz), 1.22 (3H, t, J=7.5 Hz). HPLC-MS: m/z 301 [M+H]$^+$.

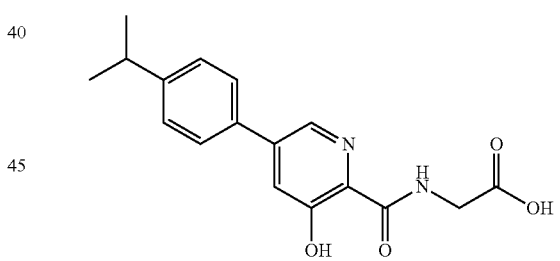

{[3-Hydroxy-5-(4-isopropylphenyl)pyridine-2-carbonyl]amino}-acetic acid: $^1$H NMR (250 MHz, DMSO-d$_6$) δ ppm 12.40 (1H, s), 9.36 (1H, t, J=6.2 Hz), 8.52 (1H, d, J=1.8 Hz), 7.70 (2H, d, J=1.8 Hz), 7.76 (2H, d, J=8.2 Hz), 7.41 (2H, d, J=8.2 Hz), 4.02 (2H, d, J=6.1 Hz), 2.97 (1H, m, J=7.0 Hz), 1.25 (6H, d, J=7.0 Hz). HPLC-MS: m/z [M+H]$^+$ 315.

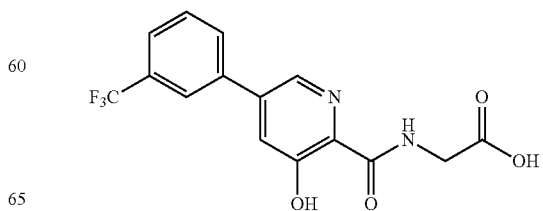

{[3-Hydroxy-5-(3-trifluoromethylphenyl)pyridine-2-carbonyl]amino}-acetic acid: ¹H NMR (250 MHz, DMSO-d₆) δ ppm 12.42 (1H, br s), 9.41 (1H, t, J=6.4 Hz), 8.61 (1H, d, J=1.8 Hz), 8.10-8.22 (2H, m), 7.88 (1H, d, J=1.8 Hz), 7.73-7.86 (2H, m), 4.03 (2H, d, J=6.1 Hz). HPLC-MS: m/z 341 [M+H]⁺.

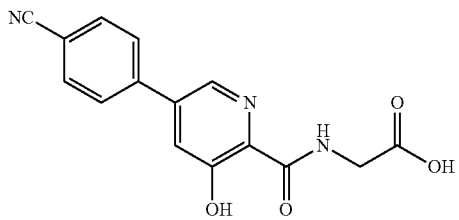 [SMILES: N#Cc1ccc(-c2cnc(C(=O)NCC(=O)O)c(O)c2)cc1]

{[5-(4-Cyanophenyl)-3-hydroxypyridine-2-carbonyl]amino}-acetic acid: ¹H NMR (400 MHz, MeOD) δ ppm 8.38 (1H, d, J=1.8 Hz), 7.75-7.83 (4H, m), 7.56 (1H, d, J=1.8 Hz), 4.06 (2H, s). HPLC-MS: m/z 298 [M+H]⁺.

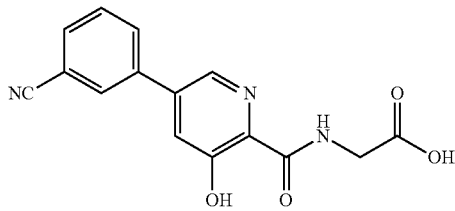 [SMILES: N#Cc1cccc(-c2cnc(C(=O)NCC(=O)O)c(O)c2)c1]

{[5-(3-Cyanophenyl)-3-hydroxypyridine-2-carbonyl]amino}-acetic acid: ¹H NMR (250 MHz, DMSO-d₆) δ ppm 12.40 (1H, s), 9.40 (1H, t, J=6.17 Hz), 8.59 (1H, d, J=1.71 Hz), 8.37 (1H, s), 8.19 (1H, d, J=7.77 Hz), 7.93 (1H, d, J=7.88 Hz), 7.86 (1H, d, J=1.94 Hz), 7.73 (1H, t, J=7.77 Hz), 4.00 (2H, d, J=6.17 Hz). HPLC-MS: m/z 298 [M+H]⁺.

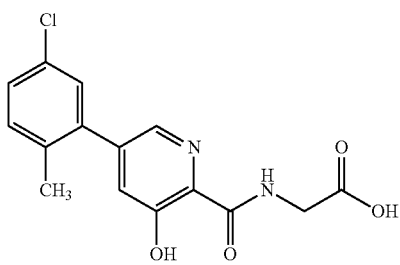 [SMILES: Cc1ccc(Cl)cc1-c1cnc(C(=O)NCC(=O)O)c(O)c1]

{[5-(5-Chloro-2-methylphenyl)-3-hydroxypyridine-2-carbonyl]amino}-acetic acid: ¹H NMR (250 MHz, DMSO-d₆) δ ppm 12.35 (1H, br s), 9.34 (1H, t, J=6.0 Hz), 8.17 (1H, d, J=1.8 Hz), 7.47 (1H, d, J=1.8 Hz), 7.33-7.45 (3H, m), 3.95 (2H, d, J=5.9 Hz), 2.22 (3H, s). HPLC-MS: m/z 321 [M+H]⁺.

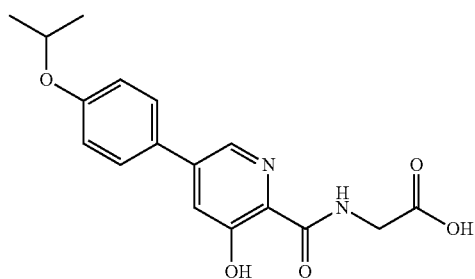 [SMILES: CC(C)Oc1ccc(-c2cnc(C(=O)NCC(=O)O)c(O)c2)cc1]

{[3-Hydroxy-5-(4-isopropoxyphenyl)pyridine-2-carbonyl]amino}-acetic acid: ¹H NMR (250 MHz, DMSO-d₆) δ ppm 12.36 (1H, br s), 9.35 (1H, t, J=5.9 Hz), 8.50 (1H, d, J=1.8 Hz), 7.71 (1H, d, J=1.8 Hz), 7.27-7.46 (3H, m), 7.02 (1H, d, J=8.5 Hz), 4.70-4.85 (1H, m), 4.01 (2H, d, J=6.1 Hz), 1.29 (6H, d, J=5.9 Hz). HPLC-MS: m/z 331 [M+H]⁺.

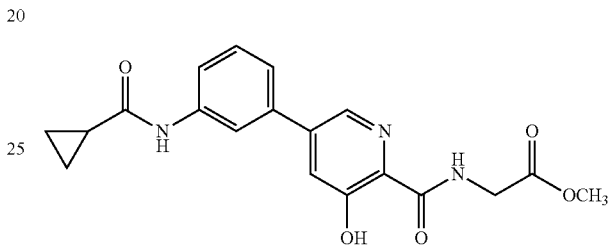

({5-[3-(Cyclopropanecarbonylamino)phenyl]-3-hydroxypyridine-2-carbonyl}-amino)-acetic acid: ¹H NMR (250 MHz, DMSO-d₆) δ ppm 12.40 (1H, br s), 10.39 (1H, s), 9.37 (1H, t, J=6.1 Hz), 8.43 (1H, d, J=1.9 Hz), 7.97 (1H, s), 7.64-7.71 (1H, m), 7.60 (1H, d, J=1.8 Hz), 7.41-7.49 (2H, m), 3.99 (2H, d, J=6.1 Hz), 1.73-1.86 (1H, m), 0.74-0.84 (4H, m). HPLC-MS: m/z 356 [M+H]⁺.

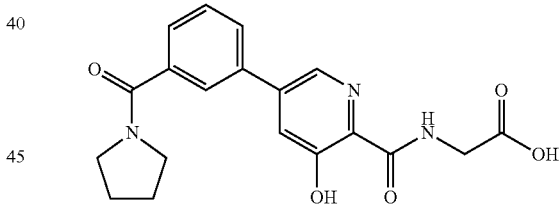

({3-Hydroxy-5-[3-(pyrrolidine-1-carbonyl)phenyl]-pyridine-2-carbonyl}amino)-acetic acid: ¹H NMR (250 MHz, DMSO-d₆) δ ppm 12.40 (1H, s), 9.38 (1H, t, J=6.3 Hz), 8.55 (1H, d, J=1.8 Hz), 7.88-7.94 (2H, m), 7.77 (1H, d, J=1.8 Hz), 7.56-7.63 (2H, m), 4.01 (2H, d, J=6.0 Hz), 3.41-3.54 (4H, m), 1.76-1.96 (4H, m). HPLC-MS: m/z 370 [M+H]⁺.

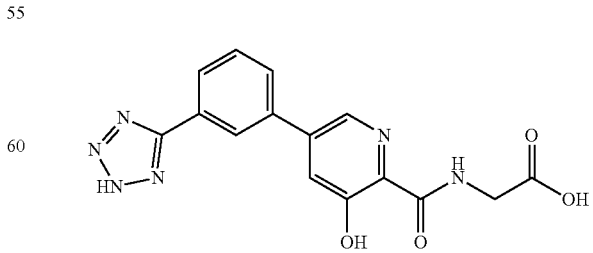

({3-Hydroxy-5-[3-(2H-tetrazol-5-yl)phenyl]-pyridine-2-carbonyl}-amino)-acetic acid: ¹H NMR (250 MHz, DMSO-d$_6$) δ ppm 12.40 (1H, s), 9.51 (1H, br s), 8.50 (1H, s), 8.20 (1H, s), 7.94 (1H, d, J=1.5 Hz), 7.88-7.99 (1H, m), 7.72 (1H, d, J=1.9 Hz), 7.34-7.53 (1H, m), 7.48 (2H, d, J=2.2 Hz), 7.00 (1H, d, J=1.8 Hz), 6.38 (1H, br s), 3.54 (2H, br s). HPLC-MS: m/z 341 [M+H]$^+$.

The fourth aspect of Category I of the present disclosure encompasses compounds having the formula:

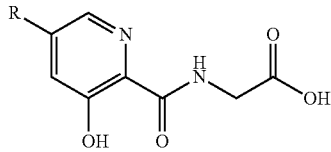

wherein R units are substituted or unsubstituted heteroaryl. Non-limiting examples of these R units are described in Table IV herein below.

TABLE IV

| No. | R |
|---|---|
| 115 | pyridin-2-yl |
| 116 | pyridin-3-yl |
| 117 | pyridin-4-yl |
| 118 | pyrimidin-2-yl |
| 119 | pyrimidin-4-yl |
| 120 | pyrimidin-5-yl |
| 121 | isoquinolin-1-yl |
| 122 | isoquinolin-3-yl |
| 123 | isoquinolin-4-yl |
| 124 | thiazol-2-yl |
| 125 | thiazol-4-yl |
| 126 | 1,2,3,4-tetrazol-5-yl |
| 127 | [1,2,4]triazol-5-yl |
| 128 | imidazol-2-yl |
| 129 | furan-2-yl |
| 130 | furan-3-yl |
| 131 | thiophene-2-yl |
| 132 | thiophene-3-yl |

The compounds which encompass the fourth aspect of Category I of the present disclosure can be prepared by the procedure outlined in Scheme II and described in Example 2 herein beginning with compounds which are members of the first and second aspect of Category I. The following are non-limiting examples of compound encompassed by the fourth aspect of Category I.

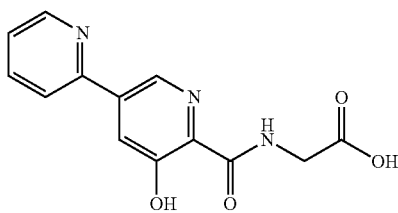 [SMILES: O=C(O)CNC(=O)c1ncc(-c2ccccn2)cc1O]

[(5'-Hydroxy-[2,3']bipyridinyl-6'-carbonyl)-amino]-acetic acid: $^1$H NMR (250 MHz, DMSO-d$_6$) δ ppm 12.45 (1H, s), 9.45 (1H, t, J=6.1 Hz), 8.91 (1H, d, J=1.8 Hz), 8.73-8.79 (1H, m) 8.20 (1H, d, J=8.0 Hz), 8.07 (1H, d, J=1.8 Hz), 8.01 (1H, dt, J=7.8, 1.8 Hz), 7.52 (1H, ddd, J=7.5, 4.8, 0.9 Hz), 4.01 (2H, d, J=6.1 Hz). HPLC-MS: m/z 274 [M+H]$^+$.

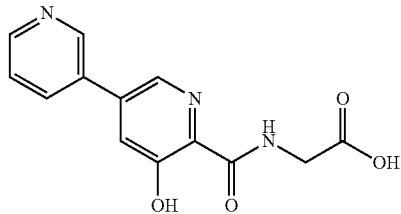 [SMILES: O=C(O)CNC(=O)c1ncc(-c2cccnc2)cc1O]

[(5-Hydroxy-[3,3']bipyridinyl-6-carbonyl)-amino]-acetic acid: $^1$H NMR (250 MHz, DMSO-d$_6$) δ ppm 12.44 (1H, br s), 9.46 (1H, t, J=6.1 Hz), 9.30 (1H, s), 8.86 (1H, d, J=5.3 Hz), 8.76 (1H, d, J=8.2 Hz), 8.67 (1H, d, J=1.9 Hz), 7.92-8.00 (2H, m), 4.02 (2H, d, J=6.1 Hz). HPLC-MS: m/z 274 [M+H]$^+$.

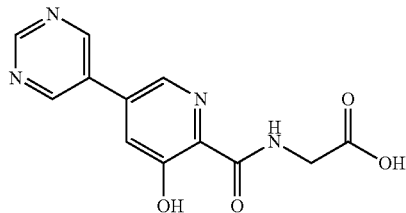 [SMILES: O=C(O)CNC(=O)c1ncc(-c2cncnc2)cc1O]

[(3-Hydroxy-5-pyrimidin-5-yl-pyridine-2-carbonyl)-amino]-acetic acid: $^1$H NMR (250 MHz, DMSO-d$_6$) δ ppm 12.45 (1H, br s), 9.45 (1H, t, J=5.9 Hz), 9.27-9.33 (3H, m), 8.67 (1H, d, J=1.8 Hz), 7.97 (1H, d, J=1.9 Hz), 4.02 (2H, d, J=6.2 Hz). HPLC-MS: m/z 275 [M+H]$^+$.

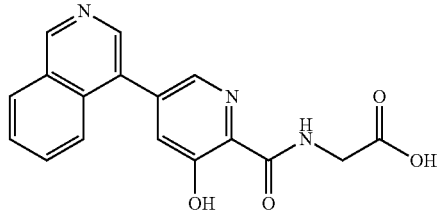 [SMILES: O=C(O)CNC(=O)c1ncc(-c2cncc3ccccc23)cc1O]

[(3-Hydroxy-5-isoquinolin-4-yl-pyridine-2-carbonyl)-amino]-acetic acid: $^1$H NMR (250 MHz, DMSO-d$_6$) δ ppm 12.53 (1H, br s), 9.83 (1H, s), 9.52 (1H, t, J=6.1 Hz), 8.71 (1H, s), 8.54 (1H, d, J=8.1 Hz), 8.38 (1H, d, J=1.7 Hz), 7.92-8.13 (3H, m), 7.73 (1H, d, J=1.7 Hz), 4.04 (2H, d, J=6.1 Hz). HPLC-MS: m/z 324 [M+H]$^+$.

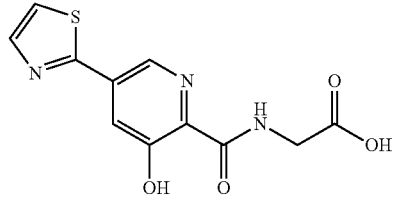 [SMILES: O=C(O)CNC(=O)c1ncc(-c2nccs2)cc1O]

[(3-Hydroxy-5-thiazol-2-yl-pyridine-2-carbonyl)-amino]-acetic acid: $^1$H NMR (250 MHz, DMSO-d$_6$) δ ppm 12.50 (1H, s), 9.46 (1H, t, J=6.1 Hz), 8.76 (1H, d, J=1.8 Hz), 8.07 (1H, d, J=3.2 Hz), 8.00 (1H, d, J=3.2 Hz), 7.90 (1H, d, J=1.8 Hz), 4.00 (2H, d, J=6.1 Hz). HPLC-MS: m/z 280 [M+H]$^+$.

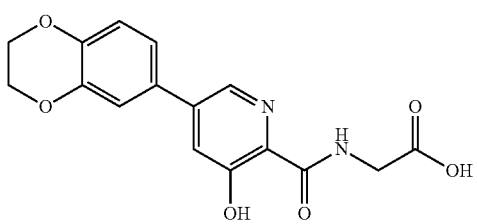 [SMILES: O=C(O)CNC(=O)c1ncc(-c2ccc3c(c2)OCCO3)cc1O]

{[5-(2,3-Dihydro-benzo[1,4]dioxin-6-yl)-3-hydroxy-pyridine-2-carbonyl]-amino}-acetic acid: $^1$H NMR (250 MHz, DMSO-$d_6$) δ ppm 12.83 (1H, br s), 12.32 (1H, s), 9.31 (1H, t, J=6.1 Hz), 8.46 (1H, d, J=1.9 Hz), 7.64 (1H, d, J=1.9 Hz), 7.37 (1H, d, J=2.2 Hz), 7.28-7.34 (1H, m), 6.98 (1H, d, J=8.5 Hz), 4.29 (4H, s), 3.99 (2H, d, J=6.1 Hz). HPLC-MS: m/z 331 [M+H]$^+$.

Category II of the present disclosure relates to compounds having the formula:

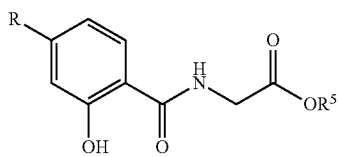

wherein the first aspect encompasses compounds having the formula:

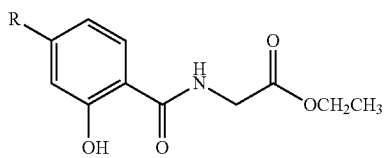

R units are substituted or unsubstituted phenyl. Non-limiting examples of these R units are described in Table V herein below.

TABLE V

| No. | R |
|---|---|
| 133 | 2-fluorophenyl |
| 134 | 3-fluorophenyl |
| 135 | 4-fluorophenyl |
| 136 | 2-chlorophenyl |
| 137 | 3-chlorophenyl |
| 138 | 4-chlorophenyl |
| 139 | 2-cyanophenyl |
| 140 | 3-cyanophenyl |
| 141 | 4-cyanophenyl |
| 142 | 2-methylphenyl |
| 143 | 3-methylphenyl |
| 144 | 4-methylphenyl |
| 145 | 2-ethylphenyl |
| 146 | 3-ethylphenyl |
| 147 | 4-ethylphenyl |
| 148 | 2-methoxyphenyl |
| 149 | 3-methoxyphenyl |
| 150 | 4-methoxyphenyl |
| 151 | 2-ethoxyphenyl |
| 152 | 3-ethoxyphenyl |
| 153 | 4-ethoxyphenyl |
| 154 | 2-iso-propoxyphenyl |
| 155 | 3-iso-propoxyphenyl |

TABLE V-continued

| No. | R |
|---|---|
| 156 | 4-iso-propoxyphenyl |
| 157 | 2-carbamoylphenyl |
| 158 | 3-carbamoylphenyl |
| 158 | 4-carbamoylphenyl |
| 160 | 2-(aziridine-1-carbonyl)phenyl |
| 161 | 3-(aziridine-1-carbonyl)phenyl |
| 162 | 4-(aziridine-1-carbonyl)phenyl |
| 163 | 2-(azetidine-1-carbonyl)phenyl |
| 164 | 3-(azetidine-1-carbonyl)phenyl |
| 165 | 4-(azetidine-1-carbonyl)phenyl |
| 166 | 2-(pyrrolidine-1-carbonyl)phenyl |
| 167 | 3-(pyrrolidine-1-carbonyl)phenyl |
| 168 | 4-(pyrrolidine-1-carbonyl)phenyl |
| 169 | 2-(piperidine-1-carbonyl)phenyl |
| 170 | 3-(piperidine-1-carbonyl)phenyl |
| 171 | 4-(piperidine-1-carbonyl)phenyl |
| 172 | 2-(acetylamino)phenyl |
| 173 | 3-(acetylamino)phenyl |
| 174 | 4-(acetylamino)phenyl |
| 175 | 2-(ethanecarbonylamino)phenyl |
| 176 | 3-(ethanecarbonylamino)phenyl |
| 177 | 4-(ethanecarbonylamino)phenyl |
| 178 | 2-(cyclopropanecarbonylamino)phenyl |
| 179 | 3-(cyclopropanecarbonylamino)phenyl |
| 180 | 4-(cyclopropanecarbonylamino)phenyl |

The compounds that encompass the first aspect of Category II of the present disclosure can be prepared by the procedure outlined in Scheme V and described in Example 3 herein below.

Scheme V

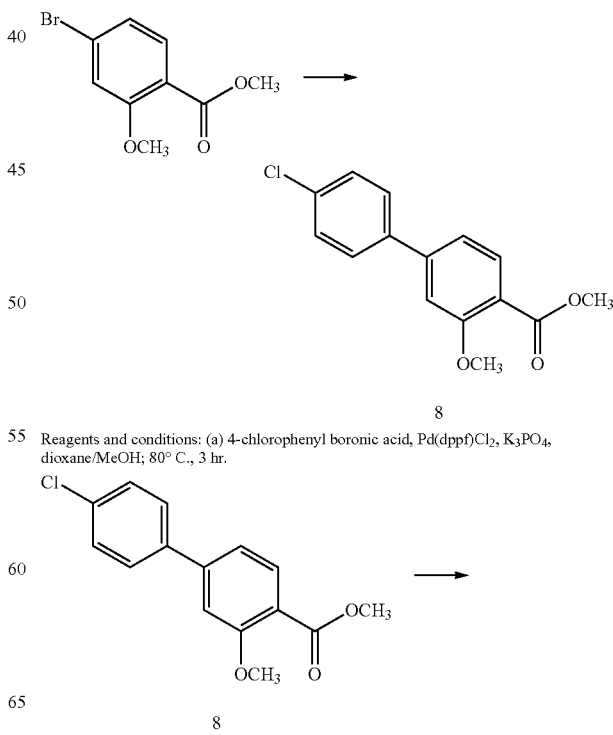

Reagents and conditions: (a) 4-chlorophenyl boronic acid, Pd(dppf)Cl$_2$, K$_3$PO$_4$, dioxane/MeOH; 80° C., 3 hr.

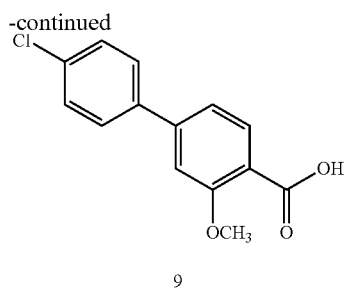

9

Reagents and conditions: (b) 4-chlorophenyl boronic acid, Pd(dppf)Cl₂, K₃PO₄,

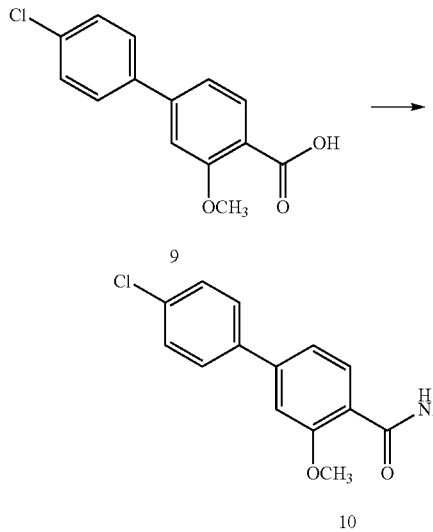

Reagents and conditions: (c) glycine ethyl ester HCl, EDCI, HOBt, DIPEA, DMF, CH₂Cl₂; rt, 16 hr.

Example 3

[(4'-Chloro-3-methoxy-biphenyl-4-carbonyl)-amino]-acetic acid ethyl ester (10)

Preparation of 4'-chloro-3-methoxy-biphenyl-4-carboxylic acid methyl ester (8): To a degassed solution of methyl 4-bromo-2-methoxybenzoate (0.70 g, 2.86 mmol) in 1,4-dioxane (10 mL) and MeOH (2.5 mL) at room temperature under nitrogen blanketing is added 4-chlorophenyl boronic acid (0.536 g, 3.43 mmol), Pd(dppf)Cl₂ (0.233 g, 0.286 mmol) and K₃PO₄ (0.728 g, 3.43 mmol). The resulting suspension is heated to 80° C. and stirred for 3 hours after which the reaction is cooled to room temperature and filtered through Celite™. The collected solids are washed with additional MeOH and the filtrate concentrated under reduced pressure. The crude material is purified over silica (hexanes:EtOAc gradient 6:1 to 4:1) to afford 0.614 g (78% yield) of the desired product as orange crystals. ¹H NMR (400 MHz, CDCl₃) δ ppm 7.89 (1H, d, J=8.0 Hz), 7.52-7.56 (2H, m), 7.44 (2H, d, J=8.7 Hz), 7.17 (1H, d, J=8.0 Hz), 7.12 (1H, d, J=1.6 Hz), 3.99 (3H, s), 3.92 (3H, s). HPLC-MS: m/z 277 [M+H]⁺.

Preparation of 4'-chloro-3-methoxy-biphenyl-4-carboxylic acid (9): To a solution of 4'-chloro-3-methoxy-biphenyl-4-carboxylic acid methyl ester, 8, (0.615 g, 2.22 mmol) in THF (20 mL) and H₂O (5 mL) at room temperature is added LiOH (0.932 g, 22.2 mmol). The resulting suspension is heated to reflux for 2 hours. The reaction is cooled and concentrated under reduced pressure. The crude product is acidified using conc. HCl and the resulting solid is collected by filtration washed with H₂O and dried to afford 0.532 g (91%) of the desired product as a grey solid. ¹H NMR (400 MHz, CDCl₃) δ ppm 10.69 (1H, br s), 8.26 (1H, d, J=8.1 Hz), 7.53-7.58 (2H, m), 7.44-7.50 (2H, m), 7.33 (1H, dd, J=8.1, 1.6 Hz), 7.20 (1H, d, J=1.3 Hz), 4.17 (3H, s). HPLC-MS: m/z 263 [M+H]⁺.

Preparation of [(4'-chloro-3-methoxy-biphenyl-4-carbonyl)-amino]-acetic acid ethyl ester (10): To a solution of 4'-chloro-3-methoxy-biphenyl-4-carboxylic acid, 9, (0.325 g, 1.24 mmol) in CH₂Cl₂ (5 mL) and DMF (1.5 mL) at room temperature under N₂ is added glycine ethyl ester hydrochloride (0.19 g, 1.36 mmol), 1-(3-dimethylamino-propyl)-3-ethylcarbodiimide (EDCI) (0.261 g, 1.36 mmol), 1-hydroxybenzotriazole (HOBt) (0.033 g, 0.248 mmol) and diisopropylethylamine (DIPEA) (0.432 ml, 2.28 mmol). The resulting suspension is stirred for 16 hours after which the reaction mixture is diluted with EtOAc and washed with 1M HCl, 1M NaOH and saturated aqueous NaCl. The organic phase is separated, dried (MgSO₄), filtered and concentrated under reduced pressure. The crude material is purified over silica (hexanes:EtOAc 1:1) to afford 0.364 g (85% yield) of the desired product as a colorless solid. ¹H NMR (400 MHz, CDCl₃) δ ppm 8.51 (1H, br s), 8.28 (1H, d, J=8.1 Hz), 7.53-7.57 (2H, m), 7.42-7.46 (2H, m), 7.27 (1H, dd, J=8.1, 1.6 Hz), 7.14 (1H, d, J=1.5 Hz), 4.29 (2H, d, J=4.8 Hz), 4.28 (2H, q, J=7.1 Hz), 4.09 (3H, s), 1.34 (3H, t, J=7.2 Hz). HPLC-MS: m/z 348 [M+H]⁺.

A further non-limiting example includes the following.

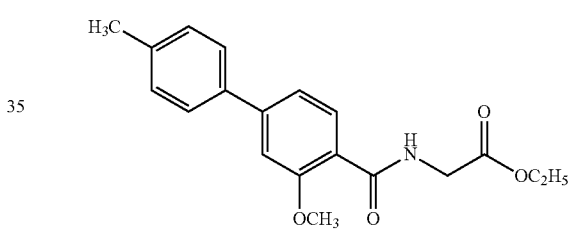

[(3-Methoxy-4'-methyl-biphenyl-4-carbonyl)-amino]-acetic acid ethyl ester: ¹H NMR (400 MHz, CDCl₃) δ ppm 8.52 (br s, 1H), 8.26 (d, J=8.14 Hz, 1H), 7.53 (d, J=8.05 Hz, 2H), 7.28-7.33 (m, 3H), 7.17 (d, J=1.37 Hz, 1H), 4.13-4.45 (m, 4H), 4.08 (s, 3H), 2.42 (s, 3H), 1.33 (t, J=7.18 Hz, 3H). HPLC-MS: m/z 328 [M+H]⁺.

The compounds of Formula (I) also encompasse compounds having the formula:

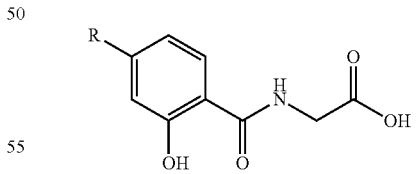

wherein R units are substituted or unsubstituted phenyl. Non-limiting examples of these R units are described in Table VI herein below.

TABLE VI

| No. | R |
| --- | --- |
| 181 | 2-fluorophenyl |
| 182 | 3-fluorophenyl |

TABLE VI-continued

| No. | R |
|---|---|
| 183 | 4-fluorophenyl |
| 184 | 2-chlorophenyl |
| 185 | 3-chlorophenyl |
| 186 | 4-chlorophenyl |
| 187 | 2-cyanophenyl |
| 188 | 3-cyanophenyl |
| 189 | 4-cyanophenyl |
| 190 | 2-methylphenyl |
| 191 | 3-methylphenyl |
| 182 | 4-methylphenyl |
| 193 | 2-ethylphenyl |
| 194 | 3-ethylphenyl |
| 195 | 4-ethylphenyl |
| 196 | 2-methoxyphenyl |
| 197 | 3-methoxyphenyl |
| 198 | 4-methoxyphenyl |
| 199 | 2-ethoxyphenyl |
| 200 | 3-ethoxyphenyl |
| 201 | 4-ethoxyphenyl |
| 202 | 2-iso-propoxyphenyl |
| 203 | 3-iso-propoxyphenyl |
| 204 | 4-iso-propoxyphenyl |
| 205 | 2-carbamoylphenyl |
| 206 | 3-carbamoylphenyl |
| 207 | 4-carbamoylphenyl |
| 208 | 2-(aziridine-1-carbonyl)phenyl |
| 209 | 3-(aziridine-1-carbonyl)phenyl |
| 210 | 4-(aziridine-1-carbonyl)phenyl |
| 211 | 2-(azetidine-1-carbonyl)phenyl |
| 212 | 3-(azetidine-1-carbonyl)phenyl |
| 213 | 4-(azetidine-1-carbonyl)phenyl |
| 214 | 2-(pyrrolidine-1-carbonyl)phenyl |
| 215 | 3-(pyrrolidine-1-carbonyl)phenyl |
| 216 | 4-(pyrrolidine-1-carbonyl)phenyl |
| 217 | 2-(piperidine-1-carbonyl)phenyl |
| 218 | 3-(piperidine-1-carbonyl)phenyl |
| 219 | 4-(piperidine-1-carbonyl)phenyl |
| 220 | 2-(acetylamino)phenyl |
| 221 | 3-(acetylamino)phenyl |
| 222 | 4-(acetylamino)phenyl |
| 223 | 2-(ethanecarbonylamino)phenyl |
| 224 | 3-(ethanecarbonylamino)phenyl |
| 225 | 4-(ethanecarbonylamino)phenyl |
| 226 | 2-(cyclopropanecarbonylamino)phenyl |
| 227 | 3-(cyclopropanecarbonylamino)phenyl |
| 228 | 4-(cyclopropanecarbonylamino)phenyl |

The compounds disclosed immediately above can be prepared by the procedure outlined in Scheme VI and described in Example 4 herein below.

Scheme VI

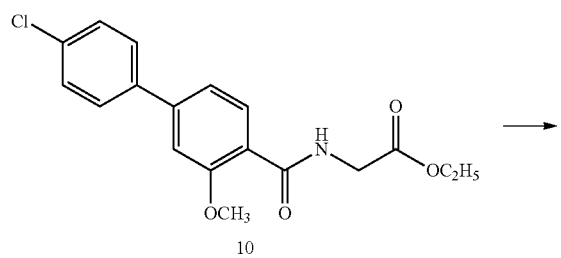

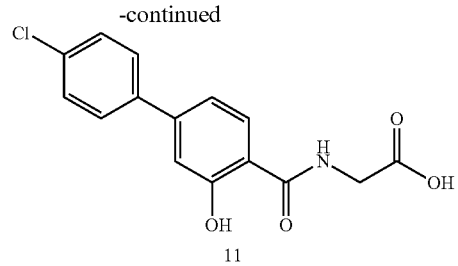

Reagents and conditions: (a) BBr$_3$, CH$_2$Cl; rt, 3 days.

Example 4

[(4'-Chloro-3-hydroxy-biphenyl-4-carbonyl)-amino]-acetic acid (11)

Preparation of [(4'-chloro-3-hydroxy-biphenyl-4-carbonyl)-amino]-acetic acid (11): To a solution of [(4'-chloro-3-methoxy-biphenyl-4-carbonyl)-amino]-acetic acid ethyl ester (0.053 g, 0.152 mmol) in CH$_2$Cl$_2$ (2 mL) at room temperature under nitrogen is added BBr$_3$ (1.52 ml of a 1M solution in CH$_2$Cl$_2$, 1.52 mmol) dropwise. The resulting mixture is stirred for 3 days after which time the reaction is quenched with H$_2$O (0.5 mL) then acidified to pH 1 with conc. HCl. The mixture is extracted with EtOAc (×2), the organic phase separated, dried (MgSO$_4$), filtered and concentrated under reduced pressure. The crude material is purified by preparative HPLC to afford 0.019 g (41% yield) of the desired product as a white solid. $^1$H NMR (400 MHz, DMSO-d$_6$) δ ppm 12.41 (1H, s), 9.19 (1H, s), 7.96 (1H, d, J=8.3 Hz), 7.74 (2H, d, J=8.7 Hz), 7.54 (2H, d, J=8.7 Hz), 7.21 (1H, d, J=1.7 Hz), 7.26 (1H, dd, J=8.3, 1.8 Hz), 3.99 (2H, d, J=5.5 Hz). HPLC-MS: m/z 306 [M+H]$^+$.

The following is a non-limiting example of the second aspect of Category II of the present disclosure.

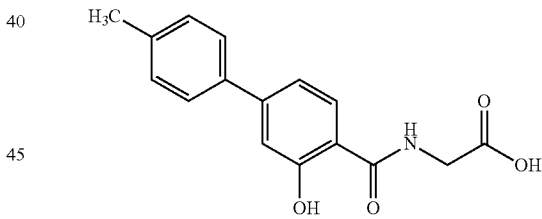

[(3-Hydroxy-4'-methyl-biphenyl-4-carbonyl)-amino]-acetic acid: $^1$H NMR (400 MHz, DMSO-d$_6$) δ ppm 12.37 (1H, s), 9.17 (1H, s), 7.94 (1H, d, J=8.32 Hz), 7.60 (2H, d, J=8.14 Hz), 7.29 (2H, d, J=7.96 Hz), 7.22 (1H, dd, J=8.32, 1.83 Hz), 7.18 (1H, d, J=1.74 Hz), 4.00 (2H, d, J=5.67 Hz), 2.35 (3H, s). HPLC-MS: m/z 286 [M+H]$^+$.

Category III of the present disclosure relates to compounds having the formula:

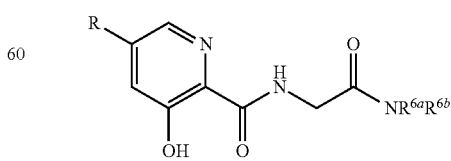

wherein non-limiting examples of R, R$^{6a}$ and R$^{6b}$ are further described herein below in Table VII.

TABLE VII

| No. | R | $R^{6a}$ | $R^{6b}$ |
|---|---|---|---|
| 229 | 2-fluorophenyl | —H | —H |
| 230 | 3-fluorophenyl | —H | —H |
| 231 | 4-fluorophenyl | —H | —H |
| 232 | 2-chlorophenyl | —H | —H |
| 233 | 3-chlorophenyl | —H | —H |
| 234 | 4-chlorophenyl | —H | —H |
| 235 | 2-methylphenyl | —H | —H |
| 236 | 3-methylphenyl | —H | —H |
| 237 | 4-methylphenyl | —H | —H |
| 238 | 2-fluorophenyl | —$CH_3$ | —H |
| 239 | 3-fluorophenyl | —$CH_3$ | —H |
| 240 | 4-fluorophenyl | —$CH_3$ | —H |
| 241 | 2-chlorophenyl | —$CH_3$ | —H |
| 242 | 3-chlorophenyl | —$CH_3$ | —H |
| 243 | 4-chlorophenyl | —$CH_3$ | —H |
| 244 | 2-methylphenyl | —$CH_3$ | —H |
| 245 | 3-methylphenyl | —$CH_3$ | —H |
| 246 | 4-methylphenyl | —$CH_3$ | —H |
| 247 | 2-fluorophenyl | —$CH_3$ | —$CH_3$ |
| 248 | 3-fluorophenyl | —$CH_3$ | —$CH_3$ |
| 249 | 4-fluorophenyl | —$CH_3$ | —$CH_3$ |
| 250 | 2-chlorophenyl | —$CH_3$ | —$CH_3$ |
| 251 | 3-chlorophenyl | —$CH_3$ | —$CH_3$ |
| 252 | 4-chlorophenyl | —$CH_3$ | —$CH_3$ |
| 253 | 2-methylphenyl | —$CH_3$ | —$CH_3$ |
| 254 | 3-methylphenyl | —$CH_3$ | —$CH_3$ |
| 255 | 4-methylphenyl | —$CH_3$ | —$CH_3$ |
| 256 | 2-fluorophenyl | —$CH_2CH_3$ | —H |
| 257 | 3-fluorophenyl | —$CH_2CH_3$ | —H |
| 258 | 4-fluorophenyl | —$CH_2CH_3$ | —H |
| 259 | 2-chlorophenyl | —$CH_2CH_3$ | —H |
| 260 | 3-chlorophenyl | —$CH_2CH_3$ | —H |
| 261 | 4-chlorophenyl | —$CH_2CH_3$ | —H |
| 262 | 2-methylphenyl | —$CH_2CH_3$ | —H |
| 263 | 3-methylphenyl | —$CH_2CH_3$ | —H |
| 264 | 4-methylphenyl | —$CH_2CH_3$ | —H |

The compounds which are encompassed within Category III of the present disclosure can be prepared by the procedures outlined herein below in Schemes VII and VIII and described in Examples 5 and 6.

Scheme VII

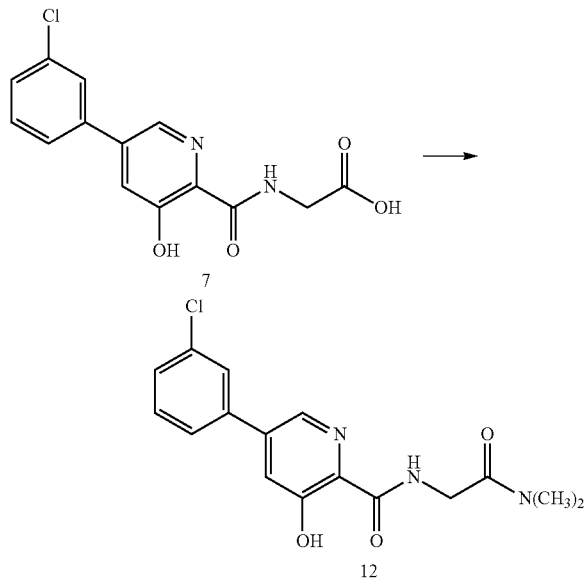

Reagents and conditions: (a)

Example 5

5-(3-Chlorophenyl)-N-(2-dimethylamino-2-oxo-ethyl)-3-hydroxylpyridin-2-yl amide (12)

Preparation of 5-(3-chlorophenyl)-N-(2-dimethylamino-2-oxoethyl) hydroxylpyridin-2-yl amide (12): To a solution of {[5-(3-chlorophenyl)-3-hydroxy-pyridine-2-carbonyl]-amino}-acetic acid, 7, (0.043 g, 0.139 mmol) in DMF (2 mL) at 0° C. under $N_2$ is added diisopropylethylamine (0.072 ml, 0.42 mmol), 1-(3-dimethylamino-propyl)-3-ethylcarbodiimide (EDCI) (0.040 g, 0.21 mmol) and 1-hydroxybenzotriazole (HOBt) (0.002 g, 0.014 mmol). The resulting mixture is stirred for 5 minutes before dimethylamine (0.10 mL of a 2M solution in THF, 0.21 mmol) is added. The reaction is warmed slowly to room temperature and stirred for 3 days. The reaction is diluted with EtOAc, washed with $H_2O$, and saturated aqueous NaCl. The organic phase is dried ($MgSO_4$), filtered, concentrated under reduced pressure and the crude material is purified over silica (EtOAc) to afford 0.20 g (43% yield) of the desired product as a colorless solid. $^1$H NMR (250 MHz, $CDCl_3$) δ ppm 11.90 (1H, s), 8.83 (1H, t, J=4.6 Hz), 8.25 (1H, d, J=1.8 Hz), 7.51 (1H, m), 7.31-7.44 (4H, m), 4.19 (2H, d, J=4.6 Hz), 2.99 (3H, s), 2.98 (3H, s). HPLC-MS: m/z 334 [M+H]$^+$.

Scheme VIII

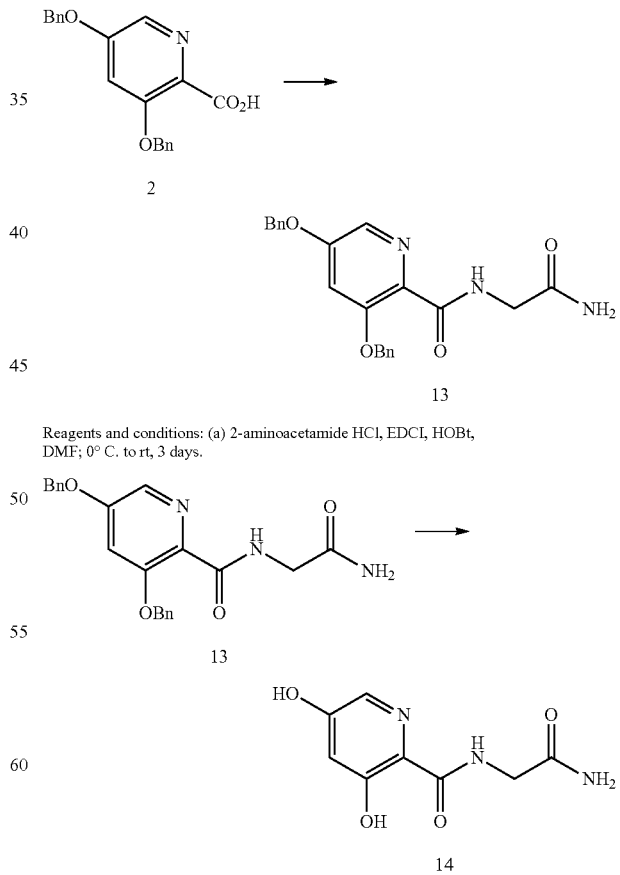

Reagents and conditions: (a) 2-aminoacetamide HCl, EDCI, HOBt, DMF; 0° C. to rt, 3 days.

Reagents and conditions: (b) $H_2$: Pd/C, MeOH, rt, 22 hr.

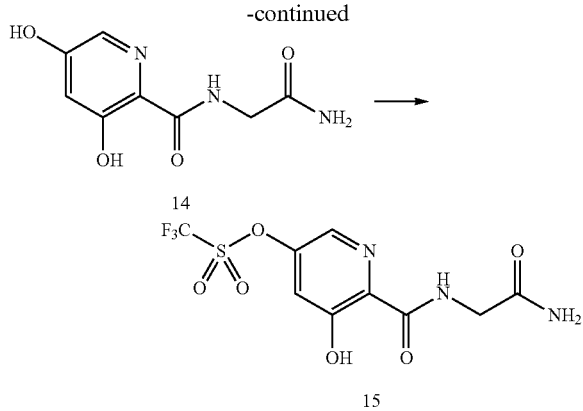

14

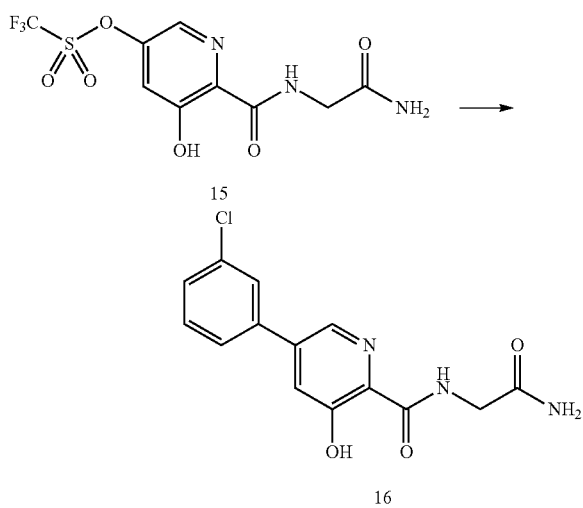

15

Reagents and conditions: (c) (CF₃SO₂)₂NC₆H₅, MeOH; rt, 24 hr.

15

16

Reagents and conditions: (d) 3-chlorophenylboronic acid, Pd(dppf)Cl₂, K₃PO₄, dioxane; 85° C., 48 hr.

Example 6

5-(3-Chlorophenyl)-N-(2-amino-2-oxoethyl)-3-hydroxylpyridin-2-yl amide (16)

Preparation of 3,5-bis-benzyloxy-N-(2-amino-2-oxoethyl)pyridin-2-yl amide (13): To a solution of 3,5-bis-benzyloxy-pyridine-2-carboxylic acid, 2, (1.00 g, 2.99 mmol) in DMF (20 mL) at room temperature under N₂ is added 1-(3-dimethylaminopropyl)-3-ethylcarbodiimide (EDCI) (0.925 g, 5.97 mmol) and 1-hydroxybenzotriazole (HOBt) (0.806 g, 5.97 mmol). The resulting solution is stirred for 15 minutes then 2-aminoacetamide hydrochloride (0.66 g, 5.97 mmol) and diisopropylethylamine (1.56 ml, 8.96 mmol) are added. After 3 days the reaction mixture is concentrated under reduced pressure and H₂O added. The solid which forms is collected by filtration and is washed with water to afford 0.598 g (51% yield) of the desired product as a white solid. $^1$H NMR (250 MHz, DMSO-d₆) δ ppm 8.39 (1H, t, J=5.6 Hz), 8.01 (1H, d, J=2.2 Hz), 7.28-7.56 (12H, m), 7.11 (1H, br s), 5.26 (2H, s), 5.25 (2H, s), 3.81 (2H, d, J=5.6 Hz). HPLC-MS: m/z 392 [M+H]⁺.

Preparation of 3,5-dihydroxy-N-(2-amino-2-oxoethy) pyridin-2-yl amide (14): A solution of 3,5-bis-benzyloxy-N-(2-amino-2-oxoethyl)pyridin-2-yl amide, 13, (0.598 g, 1.53 mmol) in EtOH (100 mL) containing 10% Pd/C (0.120 g) is stirred under an atmosphere of H₂ for 22 hours. The reaction solution is filtered through Celite™ and the collected solids are washed with hot MeOH. The combined filtrate and washings are concentrated under reduced pressure to afford 0.32 g (99% yield) of the desired product cream-colored solid. $^1$H NMR (400 MHz, DMSO-d₆) δ ppm 12.42 (1H, s), 10.84 (1H, br s), 8.75 (1H, t, J=5.8 Hz), 7.75 (1H, d, J=2.3 Hz), 7.47 (1H, br s), 7.13 (1H, br s), 6.67 (1H, d, J=2.3 Hz), 3.85 (2H, d, J=5.9 Hz). HPLC-MS: m/z 212 [M+H]⁺.

Preparation of 5-trifluoromethanesulfonoxy-N-(2-amino-2-oxoethyl)-3-hydroxypyridin-2-yl amide (15): To a solution of 3,5-dihydroxy-N-(2-amino-2-oxoethy)pyridin-2-yl amide, 14, (0.30 g, 1.42 mmol) in MeOH (10 mL) and DMF (5 mL) at 0° C. under N₂ is added diisopropylethylamine (0.247 ml, 1.42 mmol) followed by N-phenyltrifluoromethanesulfonamide (0.508 g, 1.42 mmol). The resulting mixture is warmed slowly to room temperature and stirring is continued for 24 hours. The solvent is then removed under reduced pressure and the crude material is purified over silica (2% MeOH:CH₂Cl₂) to afford 0.404 g (83% yield) of the desired product as a pale yellow solid. $^1$H NMR (250 MHz, DMSO-d₆) δ ppm 12.85 (1H, br s), 9.28 (1H, t, J=5.9 Hz), 8.41 (1H, d, J=2.3 Hz), 7.85 (1H, d, J=2.4 Hz), 7.52 (1H, br s), 7.18 (1H, br s), 3.88 (2H, d, J=6.1 Hz). HPLC-MS: m/z 344 [M+H]⁺.

Preparation of 5-(3-chlorophenyl)-N-(2-amino-2-oxoethyl)-3-hydroxypyridin-2-yl amide (16): To a degassed solution of 5-trifluoromethanesulfonoxy-N-(2-amino-2-oxoethyl)-3-hydroxypyridin-2-yl amide, 15, (0.20 g, 0.58 mmol) in 1,4-dioxane (3.5 mL) at room temperature under N₂ is added 3-chlorophenyl boronic acid (0.109 g, 0.70 mmol), K₃PO₄ (0.148 g, 0.70 mmol) and Pd(dppf)Cl₂ (0.048 g, 0.06 mmol). The resulting suspension is heated to 90° C. in a sealed tube for 22 hours. The reaction is cooled to room temperature and additional 3-chlorophenyl boronic acid (0.055 g, 0.35 mmol) and Pd(dppf)Cl₂ (0.048 g, 0.06 mmol) is added and the reaction reheated to 90° C. for an additional 22 hours. After cooling, the reaction solution is filtered through Celite™ and the collected solids are washed with additional MeOH. The filtrate and washings are concentrated under reduced pressure and the residue dissolved in CH₂Cl₂ and washed with 10% citric acid. The organic layer is dried (Na₂SO₄), filtered and concentrated under reduced pressure. The crude product is purified over silica (2% MeOH:CH₂Cl₂) to afford 0.033 g (18% yield) of the desired product as a colourless solid. $^1$H NMR (250 MHz, DMSO-d₆) δ ppm 12.46 (1H, s), 9.17 (1H, t, J=5.9 Hz), 8.55 (1H, d, J=2.0 Hz), 7.93 (1H, d, J=0.9 Hz), 7.75-7.84 (2H, m), 7.49-7.60 (3H, m), 7.18 (1H, s), 3.91 (2H, d, J=5.9 Hz). HPLC-MS: m/z 306 [M+H]⁺.

The following are non-limiting examples of compounds encompassed within Category III of the present disclosure.

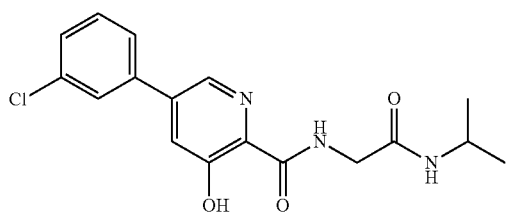 [SMILES: CC(C)NC(=O)CNC(=O)c1ncc(-c2cccc(Cl)c2)cc1O]

5-(3-Chlorophenyl)-N-(2-isopropylamino-2-oxo ethyl)-3-hydroxy-pyridin-2-yl amide: $^1$H NMR (250 MHz, CDCl₃) δ ppm 8.60 (1H, t, J=6.4 Hz), 8.25 (1H, d, J=2.0 Hz), 7.50-7.53 (1H, m), 7.44 (1H, d, J=2.0 Hz), 7.35-7.43 (3H, m), 5.69 (1H, br s), 4.04 (2H, d, J=5.9 Hz), 3.41 (1H, q, J=7.0 Hz), 1.13 (6H, d, J=6.6 Hz). HPLC-MS: m/z 348 [M+H]$^+$.

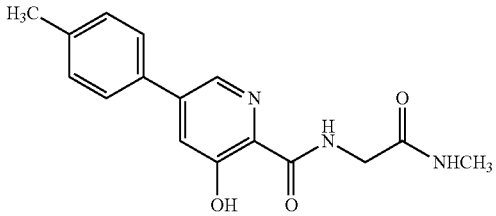 [SMILES: CNC(=O)CNC(=O)c1ncc(-c2ccc(C)cc2)cc1O]

5-(4-Methylphenyl)-N-(2-methylamino-2-oxoethyl)-3-hydroxypyridin-2-yl amide: $^1$H NMR (250 MHz, CDCl$_3$) δ ppm 11.90 (1H, s), 8.47 (1H, t, J=5.9 Hz), 8.25 (1H, d, J=1.8 Hz), 7.33-7.56 (3H, m), 7.12-7.31 (2H, m), 6.07 (1H, br s), 3.90-4.24 (2H, m), 2.66-2.98 (3H, m), 2.35 (3H, s). HPLC-MS: m/z 300 [M+H]$^+$.

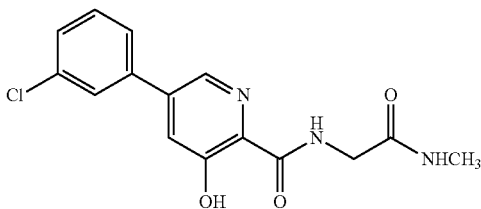 [SMILES: CNC(=O)CNC(=O)c1ncc(-c2cccc(Cl)c2)cc1O]

5-(3-Chlorophenyl)-N-(2-methylamino-2-oxoethyl)-3-hydroxy-pyridin-2-yl amide: $^1$H NMR (250 MHz, CDCl$_3$) δ ppm 11.79 (1H, br s), 8.55 (1H, br s), 8.31 (1H, s), 7.60 (1H, s), 7.41-7.53 (4H, m), 6.01 (1H, br s), 4.15 (2H, d, J=5.8 Hz), 2.90 (3H, d, J=4.7 Hz). HPLC-MS: m/z 320 [M+H]$^+$.

Category IV of the present disclosure relates to compounds having the formula:

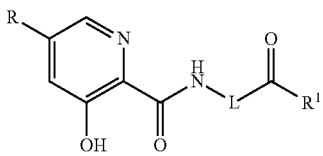

wherein the first aspect relates to compounds having the formula:

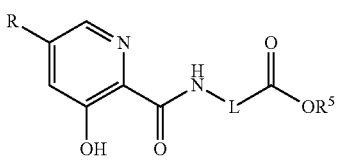

non-limiting examples of R, R$^5$, and L units are further described herein below in Table VIII.

TABLE VIII

| No. | R$^5$ | R | L |
|---|---|---|---|
| 265 | —H | 2-fluorophenyl | —C(CH$_3$)$_2$— |
| 266 | —H | 3-fluorophenyl | —C(CH$_3$)$_2$— |

TABLE VIII-continued

| No. | R$^5$ | R | L |
|---|---|---|---|
| 267 | —H | 4-fluorophenyl | —C(CH$_3$)$_2$— |
| 268 | —H | 2-chlorophenyl | —C(CH$_3$)$_2$— |
| 269 | —H | 3-chlorophenyl | —C(CH$_3$)$_2$— |
| 270 | —H | 4-chlorophenyl | —C(CH$_3$)$_2$— |
| 271 | —H | 2-methylphenyl | —C(CH$_3$)$_2$— |
| 272 | —H | 3-methylphenyl | —C(CH$_3$)$_2$— |
| 273 | —H | 4-methylphenyl | —C(CH$_3$)$_2$— |
| 274 | —CH$_3$ | 2-fluorophenyl | —C(CH$_3$)$_2$— |
| 275 | —CH$_3$ | 3-fluorophenyl | —C(CH$_3$)$_2$— |
| 276 | —CH$_3$ | 4-fluorophenyl | —C(CH$_3$)$_2$— |
| 277 | —CH$_3$ | 2-chlorophenyl | —C(CH$_3$)$_2$— |
| 278 | —CH$_3$ | 3-chlorophenyl | —C(CH$_3$)$_2$— |
| 279 | —CH$_3$ | 4-chlorophenyl | —C(CH$_3$)$_2$— |
| 280 | —CH$_3$ | 2-methylphenyl | —C(CH$_3$)$_2$— |
| 281 | —CH$_3$ | 3-methylphenyl | —C(CH$_3$)$_2$— |
| 282 | —CH$_3$ | 4-methylphenyl | —C(CH$_3$)$_2$— |
| 283 | —CH$_2$CH$_3$ | 2-fluorophenyl | —C(CH$_3$)$_2$— |
| 284 | —CH$_2$CH$_3$ | 3-fluorophenyl | —C(CH$_3$)$_2$— |
| 285 | —CH$_2$CH$_3$ | 4-fluorophenyl | —C(CH$_3$)$_2$— |
| 286 | —CH$_2$CH$_3$ | 2-chlorophenyl | —C(CH$_3$)$_2$— |
| 287 | —CH$_2$CH$_3$ | 3-chlorophenyl | —C(CH$_3$)$_2$— |
| 288 | —CH$_2$CH$_3$ | 4-chlorophenyl | —C(CH$_3$)$_2$— |
| 289 | —CH$_2$CH$_3$ | 2-methylphenyl | —C(CH$_3$)$_2$— |
| 290 | —CH$_2$CH$_3$ | 3-methylphenyl | —C(CH$_3$)$_2$— |
| 291 | —CH$_2$CH$_3$ | 4-methylphenyl | —C(CH$_3$)$_2$— |
| 292 | —H | 2-fluorophenyl | —CH(CH$_3$)— |
| 293 | —H | 3-fluorophenyl | —CH(CH$_3$)— |
| 294 | —H | 4-fluorophenyl | —CH(CH$_3$)— |
| 295 | —H | 2-chlorophenyl | —CH(CH$_3$)— |
| 296 | —H | 3-chlorophenyl | —CH(CH$_3$)— |
| 297 | —H | 4-chlorophenyl | —CH(CH$_3$)— |
| 298 | —H | 2-methylphenyl | —CH(CH$_3$)— |
| 299 | —H | 3-methylphenyl | —CH(CH$_3$)— |
| 300 | —H | 4-methylphenyl | —CH(CH$_3$)— |
| 301 | —CH$_3$ | 2-fluorophenyl | —CH(CH$_3$)— |
| 302 | —CH$_3$ | 3-fluorophenyl | —CH(CH$_3$)— |
| 303 | —CH$_3$ | 4-fluorophenyl | —CH(CH$_3$)— |
| 304 | —CH$_3$ | 2-chlorophenyl | —CH(CH$_3$)— |
| 305 | —CH$_3$ | 3-chlorophenyl | —CH(CH$_3$)— |
| 306 | —CH$_3$ | 4-chlorophenyl | —CH(CH$_3$)— |
| 307 | —CH$_3$ | 2-methylphenyl | —CH(CH$_3$)— |
| 308 | —CH$_3$ | 3-methylphenyl | —CH(CH$_3$)— |
| 309 | —CH$_3$ | 4-methylphenyl | —CH(CH$_3$)— |
| 310 | —CH$_2$CH$_3$ | 2-fluorophenyl | —CH(CH$_3$)— |
| 311 | —CH$_2$CH$_3$ | 3-fluorophenyl | —CH(CH$_3$)— |
| 312 | —CH$_2$CH$_3$ | 4-fluorophenyl | —CH(CH$_3$)— |
| 313 | —CH$_2$CH$_3$ | 2-chlorophenyl | —CH(CH$_3$)— |
| 314 | —CH$_2$CH$_3$ | 3-chlorophenyl | —CH(CH$_3$)— |
| 315 | —CH$_2$CH$_3$ | 4-chlorophenyl | —CH(CH$_3$)— |
| 316 | —CH$_2$CH$_3$ | 2-methylphenyl | —CH(CH$_3$)— |
| 317 | —CH$_2$CH$_3$ | 3-methylphenyl | —CH(CH$_3$)— |
| 318 | —CH$_2$CH$_3$ | 4-methylphenyl | —CH(CH$_3$)— |
| 319 | —H | 2-fluorophenyl | —CH$_2$CH$_2$— |
| 320 | —H | 3-fluorophenyl | —CH$_2$CH$_2$— |
| 321 | —H | 4-fluorophenyl | —CH$_2$CH$_2$— |
| 322 | —H | 2-chlorophenyl | —CH$_2$CH$_2$— |
| 323 | —H | 3-chlorophenyl | —CH$_2$CH$_2$— |
| 324 | —H | 4-chlorophenyl | —CH$_2$CH$_2$— |
| 325 | —H | 2-methylphenyl | —CH$_2$CH$_2$— |
| 326 | —H | 3-methylphenyl | —CH$_2$CH$_2$— |
| 327 | —H | 4-methylphenyl | —CH$_2$CH$_2$— |
| 328 | —CH$_3$ | 2-fluorophenyl | —CH$_2$CH$_2$— |
| 329 | —CH$_3$ | 3-fluorophenyl | —CH$_2$CH$_2$— |
| 330 | —CH$_3$ | 4-fluorophenyl | —CH$_2$CH$_2$— |
| 331 | —CH$_3$ | 2-chlorophenyl | —CH$_2$CH$_2$— |
| 332 | —CH$_3$ | 3-chlorophenyl | —CH$_2$CH$_2$— |
| 333 | —CH$_3$ | 4-chlorophenyl | —CH$_2$CH$_2$— |
| 334 | —CH$_3$ | 2-methylphenyl | —CH$_2$CH$_2$— |
| 335 | —CH$_3$ | 3-methylphenyl | —CH$_2$CH$_2$— |
| 336 | —CH$_3$ | 4-methylphenyl | —CH$_2$CH$_2$— |
| 337 | —CH$_2$CH$_3$ | 2-fluorophenyl | —CH$_2$CH$_2$— |
| 338 | —CH$_2$CH$_3$ | 3-fluorophenyl | —CH$_2$CH$_2$— |
| 339 | —CH$_2$CH$_3$ | 4-fluorophenyl | —CH$_2$CH$_2$— |
| 340 | —CH$_2$CH$_3$ | 2-chlorophenyl | —CH$_2$CH$_2$— |
| 341 | —CH$_2$CH$_3$ | 3-chlorophenyl | —CH$_2$CH$_2$— |
| 342 | —CH$_2$CH$_3$ | 4-chlorophenyl | —CH$_2$CH$_2$— |
| 343 | —CH$_2$CH$_3$ | 2-methylphenyl | —CH$_2$CH$_2$— |

TABLE VIII-continued

| No. | R⁵ | R | L |
| --- | --- | --- | --- |
| 344 | —CH₂CH₃ | 3-methylphenyl | —CH₂CH₂— |
| 345 | —CH₂CH₃ | 4-methylphenyl | —CH₂CH₂— |

The compounds described immediately abover wherein R⁵ is C₁-C₄ linear, branched, or cyclic alkyl can be prepared by the procedures outlined herein below in Scheme IX and described in Example 7.

Scheme IX

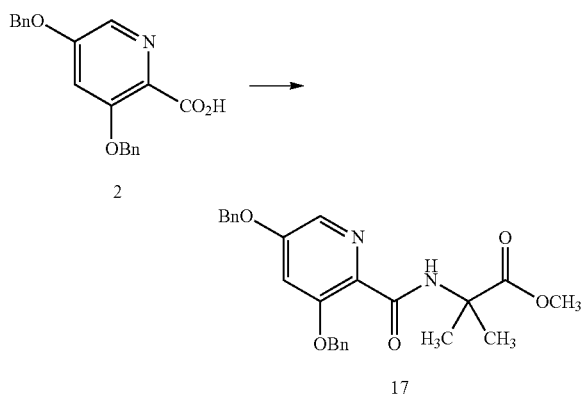

Reagents and conditions: (a) 2-amino-2-methylpropionic acid methyl ester, EDCI, HOBt, DMF; 0° C. to rt, 3 days.

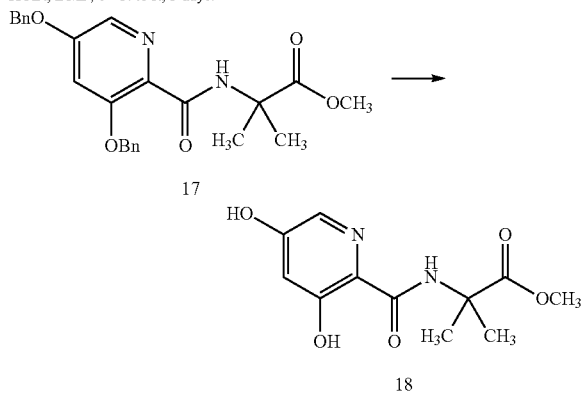

Reagents and conditions: (b) H₂: Pd/C, MeOH, rt, 22 hr.

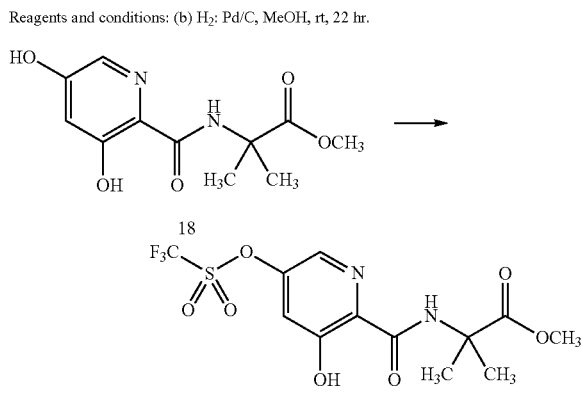

Reagents and conditions: (c) (CF₃SO₂)₂NC₆H₅, MeOH; rt, 24 hr.

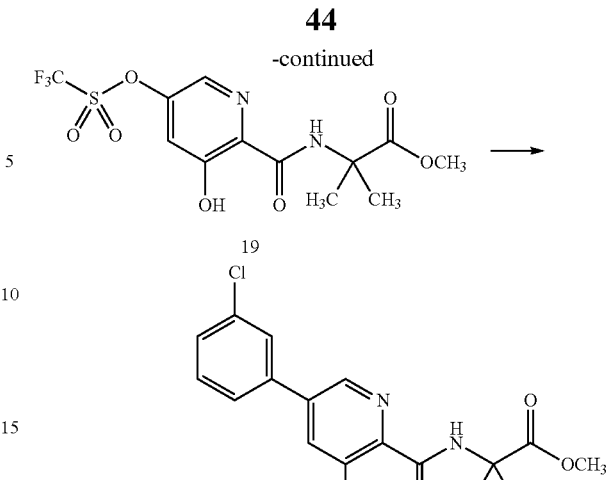

Reagents and conditions: (d) 3-chlorophenylboronic acid, Pd(dppf)Cl₂, K₃PO₄, dioxane; 85° C., 48 hr.

Example 7

2-{[5-(3-Chloro-phenyl)-3-hydroxy-pyridine-2-carbonyl]-amino}-2-methyl-propionic acid methyl ester (20)

Preparation of 2-[(3,5-bis-benzyloxy-pyridine-2-carbonyl)-amino]-2-methyl-propionic acid methyl ester (17): To a solution of 3,5-bis-benzyloxy-pyridine-2-carboxylic acid, 2, (1.0 g, 2.99 mmol) in DMF (20 mL) at room temperature under N₂ is added 1-(3-dimethylaminopropyl)-3-ethylcarbodiimide (EDCI) (0.925 g, 5.97 mmol) and 1-hydroxybenzotriazole (HOBt) (0.806 g, 5.97 mmol). The mixture is stirred for 15 minutes after which α-aminoisobutyric acid (0.917 g, 5.97 mmol) and diisopropylethyl-amine (DIPEA) (1.56 mL, 8.96 mmol) are added. The resulting solution is stirred at room temperature for 16 hours then concentrated under reduced pressure. The resulting brown oil is purified over silica (EtOAc:heptane 1:1) to afford 0.58 g (45% yield) of the desired compound as a colorless solid. ¹H NMR (250 MHz, CDCl₃) δ ppm 8.13 (1H, s), 8.02 (1H, d, J=2.3 Hz), 7.31-7.48 (10H, m), 6.90 (1H, d, J=2.3 Hz), 5.19 (2H, s), 5.10 (2H, s), 3.74 (3H, s), 1.58 (6H, s). HPLC-MS: m/z 435 [M+H]⁺.

Preparation of 2-[(3,5-dihydroxy-pyridine-2-carbonyl)-amino]-2-methyl-propionic acid methyl ester (18): A solution of 2-[(3,5-bis-benzyloxy-pyridine-2-carbonyl)-amino]-2-methylpropionic acid methyl ester, 17, (0.58 g, 1.34 mmol) in MeOH (100 mL) containing 10% Pd/C (0.116 g) is stirred under an atmosphere of H₂ for 22 hours. The reaction solution is filtered through Celite™ and the collected solids are washed with hot MeOH. The combined filtrate and washings are concentrated under reduced pressure to afford 0.321 g (94% yield) of the desired compound as a grey solid. ¹H NMR (250 MHz, MeOD) δ ppm 7.67 (1H, d, J=2.4 Hz), 6.58 (1H, d, J=2.4 Hz), 3.69 (3H, s), 1.56 (6H, s). HPLC-MS: m/z 255 [M+H]⁺.

Preparation of 2-[(3-hydroxy-5-trifluoromethanesulfonyloxy-pyridine-2-carbonyl)-amino]-2-methyl-propionic acid methyl ester (19): To a solution in 2-[(3,5-dihydroxy-pyridine-2-carbonyl)-amino]-2-methyl-propionic acid methyl ester, 18, (0.312 g, 1.23 mmol) in MeOH (10 mL) containing diisopropylethylamine (0.214 mL, 1.23 mmol) at 0° C.

under N₂ is added N-phenyltrifluoromethanesulfonamide (0.439 g, 1.23 mmol). The reaction is warmed slowly to room temperature and stirred for 40 hours. The solvent is removed under reduced pressure and the crude oil which remains is purified over silica (EtOAc:heptane 1:9) to afford 0.170 g (36% yield) of the desired compound as a yellow oil. ¹H NMR (250 MHz, MeOD) δ ppm 8.85 (1H, br s), 8.19 (1H, d, J=2.4 Hz), 7.46 (1H, d, J=2.3 Hz), 3.74 (3H, s), 1.63 (6H, s). HPLC-MS: m/z 387 [M+H]⁺.

Preparation of 2-{[5-(3-chloro-phenyl)-3-hydroxy-pyridine-2-carbonyl]-amino}-2-methyl-propionic acid methyl ester (20): To a degassed solution of 2-[(3-hydroxy trifluoromethanesulfonyloxy-pyridine-2-carbonyl)-amino]-2-methyl-propionic acid methyl ester (0.17 g, 0.44 mmol) in 1,4-dioxane (3 mL) at room temperature under N₂ is added 3-chlorophenyl boronic acid (0.082 g, 0.53 mmol), K₃PO₄ (0.112 g, 0.53 mmol) and Pd(dppf)Cl₂ (0.036 g, 0.04 mmol). The resulting suspension is heated to 85° C. in a sealed tube for 20 hours. After cooling, the reaction solution is filtered through Celite™ and the collected solids are washed with additional MeOH. The filtrate and washings are concentrated under reduced pressure and the residue dissolved in CH₂Cl₂ and washed with 10% citric acid. The organic layer is dried (Na₂SO₄), filtered and concentrated under reduced pressure. The crude product is purified over silica (EtOAc:heptane 1:4) to afford 0.112 g (73% yield) of the desired compound as a colorless oil. ¹H NMR (250 MHz, CDCl₃) δ ppm 11.83 (1H, br s), 8.29 (1H, br s), 8.10 (1H, d, J=2.0 Hz), 7.40 (1H, m), 7.08-7.34 (4H, m), 3.65 (3H, s), 1.55 (6H, s). HPLC-MS: m/z 349 [M+H]⁺.

The compounds of Formula (I) wherein R⁵ is hydrogen can be prepared by the procedures outlined herein below in Scheme X and described in Example 8

Scheme X

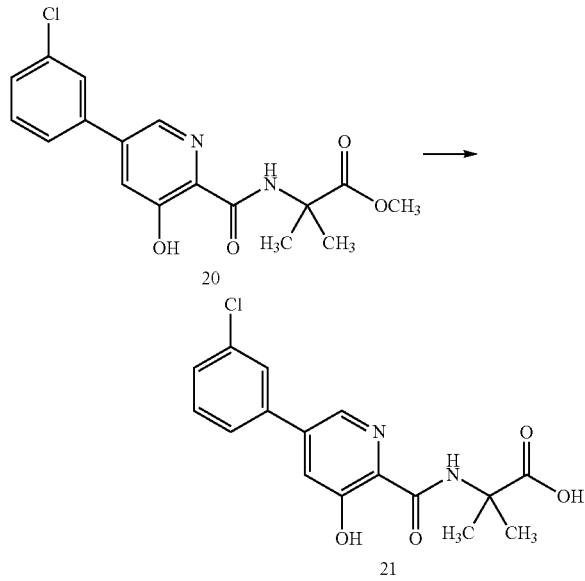

Reagents and conditions: (a) LiOH, THF/H₂O; rt, 3 days.

Example 8

2-{[5-(3-Chlorophenyl)-3-hydroxy-pyridine-2-carbonyl]-amino}-2-methyl-propionic acid (21)

Preparation of 2-{[5-(3-chlorophenyl)-3-hydroxy-pyridine-2-carbonyl]-amino}-2-methyl-propionic acid (21): To a solution of 2-{[5-(3-chlorophenyl)-3-hydroxy-pyridine carbonyl]-amino}-2-methyl-propionic acid methyl ester, 20, (0.082 g, 0.24 mmol) in THF (4 mL) is added LiOH (0.024 g, 0.98 mmol) and H₂O (1 mL) and the resulting solution stirred for 3 days at room temperature. The solvent is removed under reduced pressure and the pale yellow solid that remains is then acidified with 1M HCl to until the pH is approximately 1 and the solution extracted twice with EtOAc. The combined organic layers are combined, dried (Na₂SO₄), filtered and concentrated under reduced pressure to afford 0.064 g (81% yield) of the desired compound as a white solid. ¹H NMR (250 MHz, DMSO-d₆) δ ppm 12.99 (1H, br s), 12.25 (1H, s), 9.05 (1H, s), 8.53 (1H, d, J=2.0 Hz), 7.91 (1H, s), 7.74-7.83 (2H, m), 7.51-7.58 (2H, m), 1.58 (6H, s). HPLC-MS: m/z 335 [M+H]⁺.

Further non-limiting examples include the following.

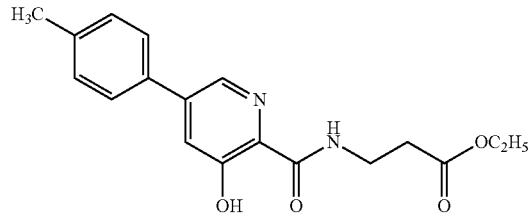 [SMILES: CCOC(=O)CCNC(=O)c1ncc(-c2ccc(C)cc2)cc1O]

3-[(3-Hydroxy-5-(4-methylphenyl)-pyridine-2-carbonyl)-amino]-propionic acid ethyl ester: ¹H NMR (250 MHz, CDCl₃) δ ppm 12.12 (1H, s), 8.44 (1H, t, J=5.9 Hz), 8.31 (1H, d, J=1.8 Hz), 7.44-7.55 (3H, m), 7.30 (2H, d, J=7.9 Hz), 4.21 (2H, q, J=7.2 Hz), 3.76 (2H, q, J=6.4 Hz), 2.68 (2H, t, J=6.2 Hz), 2.43 (3H, s), 1.30 (3H, t, J=7.2 Hz). HPLC-MS: m/z 329 [M+H]⁺.

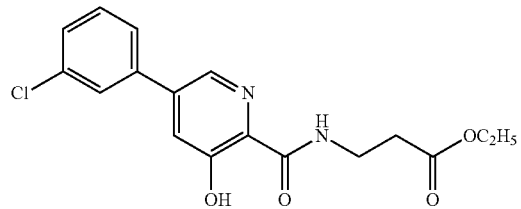 [SMILES: CCOC(=O)CCNC(=O)c1ncc(-c2cccc(Cl)c2)cc1O]

3-[(3-Hydroxy-5-(3-chlorophenyl)-pyridine-2-carbonyl)-amino]-propionic acid ethyl ester: ¹H NMR (400 MHz, CDCl₃) δ ppm 12.16 (1H, s), 8.45 (1H, t, J=5.7 Hz), 8.25 (1H, d, J=1.6 Hz), 7.55 (1H, s), 7.37-7.47 (4H, m), 4.20 (2H, q, J=7.1 Hz), 3.75 (2H, q, J=6.3 Hz), 2.68 (2H, t, J=6.2 Hz), 1.28 (3H, t, J=7.1 Hz). HPLC-MS: m/z 349 [M+H]⁺.

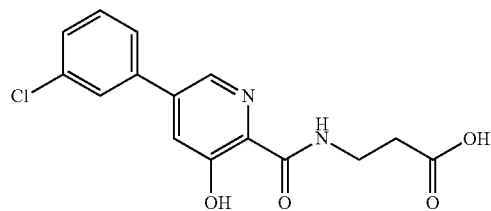 [SMILES: O=C(O)CCNC(=O)c1ncc(-c2cccc(Cl)c2)cc1O]

3-{[5-(3-Chlorophenyl)-3-hydroxy-pyridine-2-carbonyl]-amino}-propionic acid: ¹H NMR (250 MHz, DMSO-d₆) δ ppm 12.63 (1H, br s), 12.37 (1H, br s), 9.20 (1H, t, J=5.6 Hz), 8.50 (1H, d, J=1.8 Hz), 7.91 (1H, s), 7.72-7.84 (2H, m), 7.54 (2H, m), 3.54 (2H, q, J=6.8 Hz), 2.58 (2H, t, J=6.9 Hz). HPLC-MS: m/z 321 [M+H]⁺.

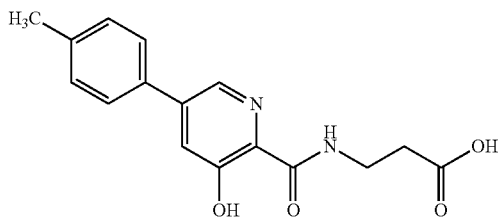 [SMILES: Cc1ccc(-c2cnc(C(=O)NCCC(=O)O)c(O)c2)cc1]

3-[(3-Hydroxy-5-(4-methylphenyl)-pyridine-2-carbonyl)-amino]-propionic acid: ¹H NMR (250 MHz, DMSO-d₆) δ ppm 12.59 (1H, br s), 9.15 (1H, t, J=5.9 Hz), 8.46 (1H, d, J=1.8 Hz), 7.70 (2H, d, J=8.2 Hz), 7.66 (1H, d, J=2.0 Hz), 7.33 (2H, d, J=8.1 Hz), 3.54 (2H, q, J=6.7 Hz), 2.57 (2H, t, J=7.0 Hz), 2.36 (3H, s). HPLC-MS: m/z 301 [M+H]⁺.

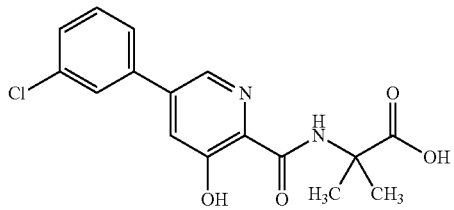 [SMILES: CC(C)(NC(=O)c1ncc(-c2cccc(Cl)c2)cc1O)C(=O)O]

2-{[5-(3-Chlorophenyl)-3-hydroxypyridine-2-carbonyl]-amino}-2-methyl-propionic acid: ¹H NMR (250 MHz, DMSO-d₆) δ ppm 12.99 (1H, br s), 12.25 (1H, s), 9.05 (1H, s), 8.53 (1H, d, J=2.0 Hz), 7.91 (1H, s), 7.74-7.83 (2H, m), 7.51-7.58 (2H, m), 1.58 (6H, s). HPLC-MS: m/z 335 [M+H]⁺.

The second aspect of Category IV relates to compounds having the formula:

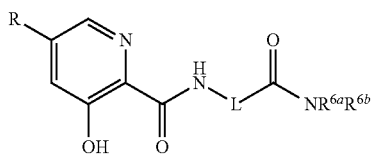

wherein non-limiting examples of R, R⁶ᵃ, R⁶ᵇ, and L units are further described herein below in Table IX.

TABLE IX

| No. | R⁶ᵃ | R⁶ᵇ | R | L |
|---|---|---|---|---|
| 346 | —H | —H | 2-fluorophenyl | —C(CH₃)₂— |
| 347 | —H | —H | 3-fluorophenyl | —C(CH₃)₂— |
| 348 | —H | —H | 4-fluorophenyl | —C(CH₃)₂— |
| 349 | —H | —H | 2-chlorophenyl | —C(CH₃)₂— |
| 350 | —H | —H | 3-chlorophenyl | —C(CH₃)₂— |
| 351 | —H | —H | 4-chlorophenyl | —C(CH₃)₂— |
| 352 | —H | —H | 2-methylphenyl | —C(CH₃)₂— |
| 353 | —H | —H | 3-methylphenyl | —C(CH₃)₂— |
| 354 | —H | —H | 4-methylphenyl | —C(CH₃)₂— |
| 355 | —CH₃ | —H | 2-fluorophenyl | —C(CH₃)₂— |
| 356 | —CH₃ | —H | 3-fluorophenyl | —C(CH₃)₂— |
| 357 | —CH₃ | —H | 4-fluorophenyl | —C(CH₃)₂— |
| 358 | —CH₃ | —H | 2-chlorophenyl | —C(CH₃)₂— |
| 359 | —CH₃ | —H | 3-chlorophenyl | —C(CH₃)₂— |
| 360 | —CH₃ | —H | 4-chlorophenyl | —C(CH₃)₂— |
| 361 | —CH₃ | —H | 2-methylphenyl | —C(CH₃)₂— |
| 362 | —CH₃ | —H | 3-methylphenyl | —C(CH₃)₂— |
| 363 | —CH₃ | —H | 4-methylphenyl | —C(CH₃)₂— |
| 364 | —CH₃ | —CH₃ | 2-fluorophenyl | —C(CH₃)₂— |
| 365 | —CH₃ | —CH₃ | 3-fluorophenyl | —C(CH₃)₂— |
| 366 | —CH₃ | —CH₃ | 4-fluorophenyl | —C(CH₃)₂— |
| 367 | —CH₃ | —CH₃ | 2-chlorophenyl | —C(CH₃)₂— |
| 368 | —CH₃ | —CH₃ | 3-chlorophenyl | —C(CH₃)₂— |
| 369 | —CH₃ | —CH₃ | 4-chlorophenyl | —C(CH₃)₂— |
| 370 | —CH₃ | —CH₃ | 2-methylphenyl | —C(CH₃)₂— |
| 371 | —CH₃ | —CH₃ | 3-methylphenyl | —C(CH₃)₂— |
| 372 | —CH₃ | —CH₃ | 4-methylphenyl | —C(CH₃)₂— |
| 373 | —CH₂CH₃ | —H | 2-fluorophenyl | —CH(CH₃)— |
| 374 | —CH₂CH₃ | —H | 3-fluorophenyl | —CH(CH₃)— |
| 375 | —CH₂CH₃ | —H | 4-fluorophenyl | —CH(CH₃)— |
| 376 | —CH₂CH₃ | —H | 2-chlorophenyl | —CH(CH₃)— |
| 377 | —CH₂CH₃ | —H | 3-chlorophenyl | —CH(CH₃)— |
| 378 | —CH₂CH₃ | —H | 4-chlorophenyl | —CH(CH₃)— |
| 379 | —CH₂CH₃ | —H | 2-methylphenyl | —CH(CH₃)— |
| 380 | —CH₂CH₃ | —H | 3-methylphenyl | —CH(CH₃)— |
| 381 | —CH₂CH₃ | —H | 4-methylphenyl | —CH(CH₃)— |
| 382 | —CH₂CH₃ | —CH₂CH₃ | 2-fluorophenyl | —CH(CH₃)— |
| 383 | —CH₂CH₃ | —CH₂CH₃ | 3-fluorophenyl | —CH(CH₃)— |
| 384 | —CH₂CH₃ | —CH₂CH₃ | 4-fluorophenyl | —CH(CH₃)— |
| 385 | —CH₂CH₃ | —CH₂CH₃ | 2-chlorophenyl | —CH(CH₃)— |
| 386 | —CH₂CH₃ | —CH₂CH₃ | 3-chlorophenyl | —CH(CH₃)— |
| 387 | —CH₂CH₃ | —CH₂CH₃ | 4-chlorophenyl | —CH(CH₃)— |
| 388 | —CH₂CH₃ | —CH₂CH₃ | 2-methylphenyl | —CH(CH₃)— |
| 389 | —CH₂CH₃ | —CH₂CH₃ | 3-methylphenyl | —CH(CH₃)— |
| 390 | —CH₂CH₃ | —CH₂CH₃ | 4-methylphenyl | —CH(CH₃)— |

Another subgenus of the Compounds of Formula (I) can be prepared by the procedures outlined herein below in Scheme XI and described in Example 9.

Scheme XI

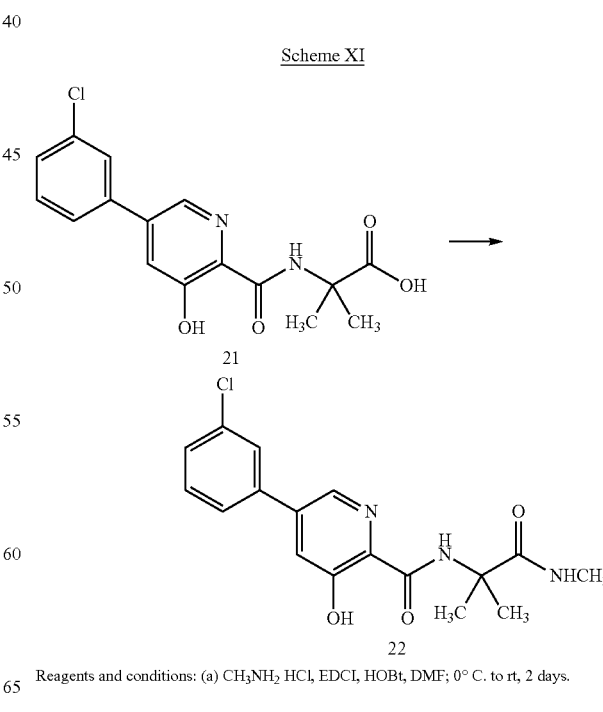

Reagents and conditions: (a) CH₃NH₂ HCl, EDCI, HOBt, DMF; 0° C. to rt, 2 days.

Example 9

5-(3-Chlorophenyl)-N-(2-methylamino2-oxo-1,1-dimethyethyl)-3-hydroxy-pyridin-2-yl amide (22)

Preparation of 5-(3-chlorophenyl)-N-(2-methylamino2-oxo-1,1-dimethyethyl) hydroxy-pyridin-2-yl amide (22): To a solution of 2-{[5-(3-chlorophenyl)-3-hydroxy-pyridine-2-carbonyl]-amino}-2-methyl-propionic acid, 21, (0.030 g, 0.09 mmol) in DMF (2 mL) at room temperature under $N_2$ is added 1-(3-dimethylamino-propyl)-3-ethyl-carbodiimide (EDCI) (0.021 g, 0.13 mmol), 1-hydroxybenzotriazole (HOBt) (0.012 g, 0.09 mmol) and diisopropylethylamine (DIPEA) (0.047 ml, 0.27 mmol). The reaction is stirred for 5 minutes then methylamine hydrochloride (0.09 g, 0.13 mmol) is added. After stirring for 2 days, the solvent is removed under reduced pressure and the residue partitioned between $CH_2Cl_2$ and $H_2O$. The organic layer is separated, washed with sat. NaCl, dried ($Na_2SO_4$), filtered and concentrated under reduced pressure. The crude product is purified over silica (MeOH:$CH_2Cl_2$ 1:99) to afford 0.025 g (80% yield) of the desired compound as a colorless oil. $^1$H NMR (250 MHz, $CDCl_3$) δ ppm 11.93 (1H, br s), 8.50 (1H, s), 8.26 (1H, d, J=1.8 Hz), 7.56 (1H, d, J=1.4 Hz), 7.38-7.50 (4H, m), 6.50 (1H, br s), 2.87 (3H, d, J=4.7 Hz), 1.71 (6H, s). HPLC-MS: m/z 348 [M+H]$^+$.

Another subgenus of the compounds of Formula (I) relates to compounds having the formula:

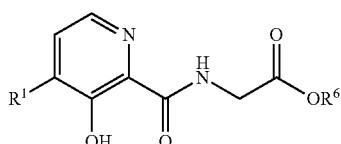

which can be exemplified by compounds having the formula:

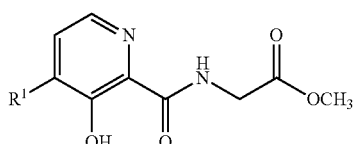

wherein the $R^1$ units are substituted or unsubstituted phenyl. Non-limiting examples of these units are described in Table X herein below.

TABLE X

| No. | $R^1$ |
|---|---|
| 391 | 2-fluorophenyl |
| 392 | 3-fluorophenyl |
| 393 | 4-fluorophenyl |
| 394 | 2-chlorophenyl |
| 395 | 3-chlorophenyl |
| 396 | 4-chlorophenyl |
| 397 | 2-cyanophenyl |
| 398 | 3-cyanophenyl |
| 399 | 4-cyanophenyl |
| 400 | 2-methylphenyl |
| 401 | 3-methylphenyl |
| 402 | 4-methylphenyl |
| 403 | 2-ethylphenyl |

TABLE X-continued

| No. | $R^1$ |
|---|---|
| 404 | 3-ethylphenyl |
| 405 | 4-ethylphenyl |
| 406 | 2-methoxyphenyl |
| 407 | 3-methoxyphenyl |
| 408 | 4-methoxyphenyl |
| 409 | 2-ethoxyphenyl |
| 410 | 3-ethoxyphenyl |
| 411 | 4-ethoxyphenyl |
| 412 | 2-iso-propoxyphenyl |
| 413 | 3-iso-propoxyphenyl |
| 414 | 4-iso-propoxyphenyl |
| 415 | 2-carbamoylphenyl |
| 416 | 3-carbamoylphenyl |
| 417 | 4-carbamoylphenyl |
| 418 | 2-(aziridine-1-carbonyl)phenyl |
| 419 | 3-(aziridine-1-carbonyl)phenyl |
| 420 | 4-(aziridine-1-carbonyl)phenyl |
| 421 | 2-(azetidine-1-carbonyl)phenyl |
| 422 | 3-(azetidine-1-carbonyl)phenyl |
| 423 | 4-(azetidine-1-carbony l)phenyl |
| 424 | 2-(pyrrolidine-1-carbonyl)phenyl |
| 425 | 3-(pyrrolidine-1-carbonyl)phenyl |
| 426 | 4-(pyrrolidine-1-carbonyl)phenyl |
| 427 | 2-(piperidine-1-carbonyl)phenyl |
| 428 | 3-(piperidine-1-carbonyl)phenyl |
| 429 | 4-(piperidine-1-carbonyl)phenyl |
| 430 | 2-(acetylamino)phenyl |
| 431 | 3-(acetylamino)phenyl |
| 432 | 4-(acetylamino)phenyl |
| 433 | 2-(ethanecarbonylamino)phenyl |
| 434 | 3-(ethanecarbonylamino)phenyl |
| 435 | 4-(ethanecarbonylamino)phenyl |
| 436 | 2-(cyclopropanecarbonylamino)phenyl |
| 437 | 3-(cyclopropanecarbonylamino)phenyl |
| 438 | 4-(cyclopropanecarbonylamino)phenyl |

Another subgenus of the compounds of Formula (I) can be prepared by the procedure outlined in Scheme XII and described in Example 10 herein below.

Scheme XII

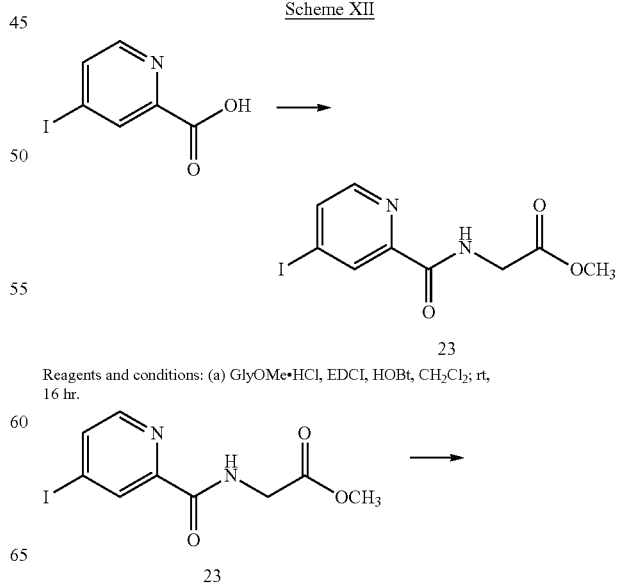

Reagents and conditions: (a) GlyOMe•HCl, EDCI, HOBt, $CH_2Cl_2$; rt, 16 hr.

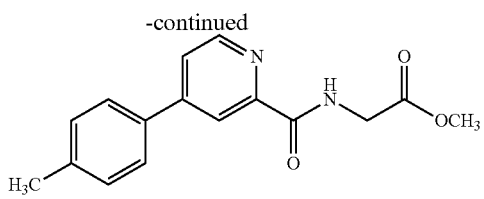

24

Reagents and conditions: (b) 4-methylphenyl boronic acid, Pd(dppf)Cl₂, K₃PO₄, dioxane/H₂O; 70° C., 16 hr.

Example 10

[(4-(4-Methylphenyl)pyridine-2-carbonyl)amino]-acetic acid methyl ester (24)

Preparation of [(4-iodo-pyridine-2-carbonyl)-amino]-acetic acid methyl ester (23): To a solution of 4-iodo-picolinic acid (1.41 g, 5.66 mmol) in CH₂Cl₂ (35 mL) at room temperature under N₂ is added 1-(3-dimethylaminopropyl)-3-ethylcarbodiimide (EDCI) (1.62 g, 8.49 mmol) and 1-hydroxybenzotriazole (HOBt) (0.077 g, 0.57 mmol). The solution is stirred for 5 minutes and glycine methyl ester hydrochloride (1.07 g, 8.49 mmol) is added and the reaction is stirred 16 hours. The reaction volume is concentrated under reduced pressure and the crude material was partitioned between EtOAc and 1M K₂CO₃. The aqueous phase is removed and the organic phase washed with H₂O, sat. NaCl, dried (MgSO₄), filtered and concentrated under reduced pressure to afford a brown oil which is purified over silica (EtOAc:heptane gradient 1:4) to afford 0.805 g (44% yield) of the desired product as a colorless solid. HPLC-MS: m/z 321 [M+H]⁺.

Preparation of [(4-(4-methylphenyl)pyridine-2-carbonyl)amino]-acetic acid methyl ester (24): To a degassed solution of [(4-iodo-pyridine-2-carbonyl)-amino]-acetic acid methyl ester, 23, (0.150, 0.47 mmol) in 1,4-dioxane (4 mL) and MeOH (2 mL) is added K₃PO₄ (0.109 mg, 0.52 mmol), Pd(dppf)Cl₂ (0.038 g, 0.047 mmol) and 4-methylphenyl boronic acid (0.064 g, 0.47 mmol). The reaction is heated to 70° C. in a sealed tube under N₂ for 16 hours. The solvents are then removed under reduced pressure and the solid which remains is partitioned between CH₂Cl₂ and 1M K₂CO₃. The aqueous phase is removed and the organic phase washed with H₂O, sat. NaCl, dried (MgSO₄), filtered and concentrated under reduced pressure. The crude material is purified over silica (EtOAc:heptane gradient 1:4 to 3:7) to afford 0.113 g (85% yield) of the desired compound. ¹H NMR (400 MHz, CDCl₃) δ ppm 8.60 (1H, dd, J=5.1, 0.7 Hz), 8.55 (1H, t, J=4.8 Hz), 8.43-8.44 (1H, m), 8.43 (1H, s), 7.66 (1H, dd, J=5.1, 1.8 Hz), 7.63 (2H, d, J=8.4 Hz), 7.32 (2H, d, J=8.1 Hz), 4.31 (1H, d, J=5.9 Hz), 3.81 (2H, s), 2.43 (3H, s). HPLC-MS: m/z 285 [M+H]⁺.

The following are non-limiting examples of compounds described immediately above.

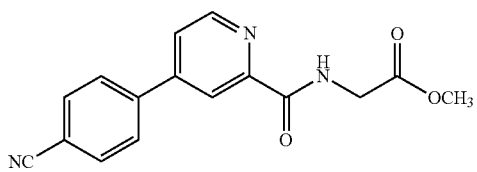 [SMILES: COC(=O)CNC(=O)c1cc(-c2ccc(C#N)cc2)ccn1]

{[4-(4-Cyanophenyl)pyridine-2-carbonyl]amino}-acetic acid methyl ester: ¹H NMR (400 MHz, CDCl₃) δ ppm 8.63 (1H, d, J=5.1 Hz), 8.45 (1H, t, J=5.3 Hz), 8.36 (1H, d, J=1.8 Hz), 7.74 (4H, s), 7.59 (1H, dd, J=5.1, 1.8 Hz), 4.24 (2H, d, J=5.9 Hz), 3.74 (3H, s). HPLC-MS: m/z 296 [M+H]⁺.

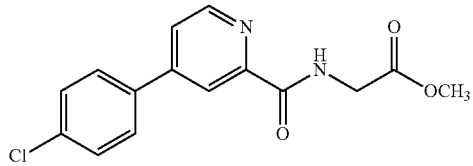 [SMILES: COC(=O)CNC(=O)c1cc(-c2ccc(Cl)cc2)ccn1]

{[4-(4-Chlorophenyl)pyridine-2-carbonyl]amino}-acetic acid methyl ester: ¹H NMR (400 MHz, CDCl₃) δ ppm 8.56 (1H, dd, J=4.9, 0.9 Hz), 8.47 (1H, t, J=5.1 Hz), 8.33 (1H, dd, J=2.0, 0.9 Hz), 7.51-7.61 (3H, m), 7.41 (2H, m), 4.23 (2H, d, J=5.5 Hz), 3.74 (3H, s). HPLC-MS: m/z 305 [M+H]⁺.

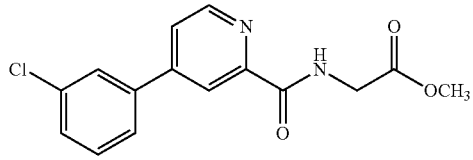 [SMILES: COC(=O)CNC(=O)c1cc(-c2cccc(Cl)c2)ccn1]

{[4-(3-Chlorophenyl)pyridine-2-carbonyl]amino}acetic acid methyl ester: ¹H NMR (400 MHz, CDCl₃) δ ppm 8.57 (1H, dd, J=5.1, 0.7 Hz), 8.47 (1H, t, J=5.1 Hz), 8.33 (1H, m), 7.62 (1H, m), 7.57 (1H, dd, J=5.1, 1.8 Hz), 7.47-7.54 (1H, m), 7.31-7.42 (2H, m), 4.24 (2H, d, J=5.9 Hz), 3.74 (3H, s). HPLC-MS: m/z 305 [M+H]⁺.

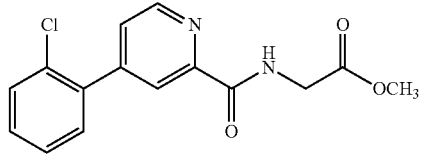 [SMILES: COC(=O)CNC(=O)c1cc(-c2ccccc2Cl)ccn1]

{[4-(2-Chlorophenyl)pyridine-2-carbonyl]-amino}-acetic acid methyl ester: ¹H NMR (400 MHz, CDCl₃) δ ppm 8.57 (1H, dd, J=5.1, 0.7 Hz), 8.46 (1H, t, J=4.6 Hz), 8.20 (1H, dd, J=1.8, 0.7 Hz), 7.50 (1H, dd, J=5.1, 1.8 Hz), 7.42-7.46 (1H, m), 7.30 (1H, d, J=1.8 Hz), 7.28-7.32 (2H, m), 4.23 (2H, d, J=5.5 Hz), 3.74 (3H, s). HPLC-MS: m/z 305 [M+H]⁺.

The second aspect of Category V encompasses compounds having the formula:

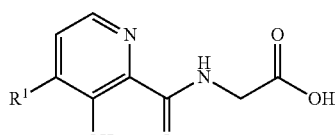

wherein R¹ units are substituted or unsubstituted phenyl, non-limiting examples of which are described in Table XI herein below.

TABLE XI

| No. | R¹ |
|---|---|
| 439 | 2-fluorophenyl |
| 440 | 3-fluorophenyl |
| 441 | 4-fluorophenyl |
| 442 | 2-chlorophenyl |
| 443 | 3-chlorophenyl |
| 444 | 4-chlorophenyl |
| 445 | 2-cyanophenyl |
| 446 | 3-cyanophenyl |
| 447 | 4-cyanophenyl |
| 448 | 2-methylphenyl |
| 449 | 3-methylphenyl |
| 450 | 4-methylphenyl |
| 451 | 2-ethylphenyl |
| 452 | 3-ethylphenyl |
| 453 | 4-ethylphenyl |
| 454 | 2-methoxyphenyl |
| 455 | 3-methoxyphenyl |
| 456 | 4-methoxyphenyl |
| 457 | 2-ethoxyphenyl |
| 458 | 3-ethoxyphenyl |
| 459 | 4-ethoxyphenyl |
| 460 | 2-iso-propoxyphenyl |
| 461 | 3-iso-propoxyphenyl |
| 462 | 4-iso-propoxyphenyl |
| 463 | 2-carbamoylphenyl |
| 464 | 3-carbamoylphenyl |
| 465 | 4-carbamoylphenyl |
| 466 | 2-(aziridine-1-carbonyl)phenyl |
| 467 | 3-(aziridine-1-carbonyl)phenyl |
| 468 | 4-(aziridine-1-carbonyl)phenyl |
| 469 | 2-(azetidine-1-carbonyl)phenyl |
| 470 | 3-(azetidine-1-carbonyl)phenyl |
| 471 | 4-(azetidine-1-carbonyl)phenyl |
| 472 | 2-(pyrrolidine-1-carbonyl)phenyl |
| 473 | 3-(pyrrolidine-1-carbonyl)phenyl |
| 474 | 4-(pyrrolidine-1-carbonyl)phenyl |
| 475 | 2-(piperidine-1-carbonyl)phenyl |
| 476 | 3-(piperidine-1-carbonyl)phenyl |
| 477 | 4-(piperidine-1-carbonyl)phenyl |
| 478 | 2-(acetylamino)phenyl |
| 479 | 3-(acetylamino)phenyl |
| 480 | 4-(acetylamino)phenyl |
| 481 | 2-(ethanecarbonylamino)phenyl |
| 482 | 3-(ethanecarbonylamino)phenyl |
| 483 | 4-(ethanecarbonylamino)phenyl |
| 484 | 2-(cyclopropanecarbonylamino)phenyl |
| 485 | 3-(cyclopropanecarbonylamino)phenyl |
| 486 | 4-(cyclopropanecarbonylamino)phenyl |

The compounds of the second aspect can be prepared by the procedure outlined in Scheme XIII and described in Example 11 herein below.

Scheme XIII

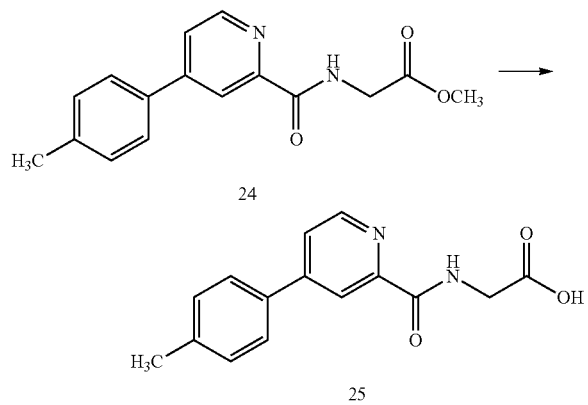

Reagents and conditions: (a) LiOH, THF, H₂O; rt, 16 hr.

Example 11

[(4-(4-Methyl-phenyl)pyridine-2-carbonyl)-amino]-acetic acid (25)

Preparation of [(4-(4-Methyl-phenyl)pyridine-2-carbonyl)-amino]-acetic acid (25): To a solution of [(4-(4-methyl-phenyl)pyridine-2-carbonyl)-amino]-acetic acid methyl ester, 24, (0.092 g, 0.32 mmol) in THF (2 mL) at room temperature is added H₂O (1 mL) and LiOH·H₂O (0.027 g, 0.64 mmol). The reaction is stirred for 16 hours after which time the solution is acidified using 1M HCl. The solvents are removed under reduced pressure and the solid that remains is suspended in a mixture of THF:MeOH and filtered. The filtrate is concentrated under reduced pressure and the resulting solid is triturated with MeOH and collected by filtration to provide 0.012 g (12% yield) of the desired compound as a colorless solid. ¹H NMR (250 MHz, MeOD) δ ppm 8.69 (1H, d, J=4.8 Hz), 8.38 (1H, s), 7.86 (1H, d, J=6.2 Hz), 7.72 (2H, d, J=8.1 Hz), 7.38 (1H, d, J=7.9 Hz), 4.21 (1H, s), 2.44 (2H, s). HPLC-MS: m/z 271 [M+H]⁺.

The following are non-limiting examples of compounds compounds of Formula (I).

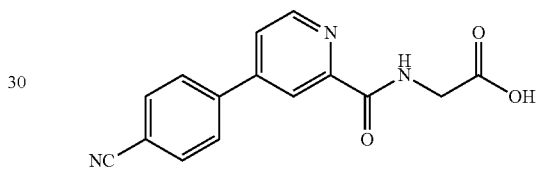

{[4-(4-Cyanophenyl)pyridine-2-carbonyl]amino}-acetic acid: ¹H NMR (250 MHz, MeOD) δ ppm 8.69 (1H, d, J=6.0 Hz), 8.38 (1H, br s), 7.71-8.01 (2H, m), 4.10 (2H, s). HPLC-MS: m/z 282 [M+H]⁺.

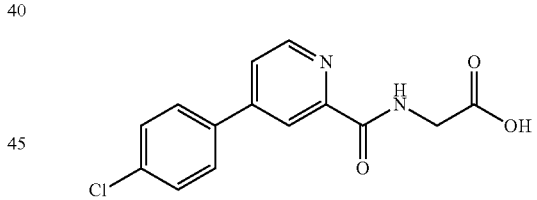

{[4-(4-Chlorophenyl)pyridine-2-carbonyl]-amino}-acetic acid: ¹H NMR (250 MHz, MeOD) δ ppm 8.75 (1H, s), 8.44 (1H, br s), 7.85 (3H, m), 7.57 (2H, d, J=7.8 Hz), 4.23 (2H, s). HPLC-MS: m/z 291 [M+H]⁺.

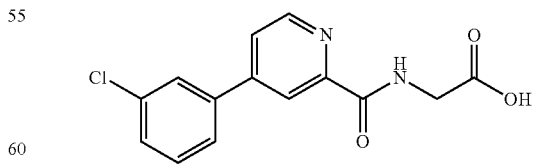

{[4-(3-Chlorophenyl)pyridine-2-carbonyl]amino}-acetic acid: ¹H NMR (400 MHz, MeOD) δ ppm 8.63 (1H, d, J=5.5 Hz), 8.27 (1H, br s), 7.73 (1H, s), 7.77 (1H, d, J=4.0 Hz), 7.64 (1H, d, J=7.0 Hz), 7.36-7.49 (3H, m), 4.09 (2H, s). HPLC-MS: m/z 291 [M+H]⁺.

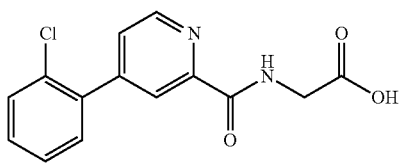 [SMILES: O=C(O)CNC(=O)c1cc(-c2ccccc2Cl)ccn1]

{[4-(2-Chlorophenyl)pyridine-2-carbonyl]amino}-acetic acid: $^1$H NMR (250 MHz, MeOD) δ ppm 8.63 (1H, d, J=4.9 Hz), 8.05-8.10 (1H, m), 7.55 (1H, dd, J=4.9, 1.6 Hz), 7.46 (1H, dt, J=3.9, 2.1 Hz), 7.35 (4H, d, J=2.7 Hz), 4.08 (2H, s). HPLC-MS: m/z 291 [M+H]$^+$.

Another subgenus of the compounds of Formula (I) have the formula:

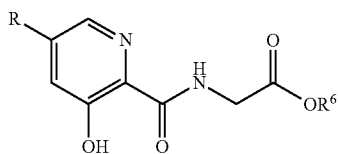

wherein non-limiting examples of R and R$^6$ are further described herein below in Table XII.

TABLE XII

| No. | R | R$^6$ |
|---|---|---|
| 487 | —H | —H |
| 488 | —H | —CH$_3$ |
| 489 | —H | —CH$_2$CH$_3$ |
| 490 | —H | —CH$_2$CH$_2$CH$_3$ |
| 491 | —H | —C(CH$_3$)$_3$ |
| 492 | —OH | —H |
| 493 | —OH | —CH$_3$ |
| 494 | —OH | —CH$_2$CH$_3$ |
| 495 | —OH | —CH$_2$CH$_2$CH$_3$ |
| 496 | —OH | —C(CH$_3$)$_3$ |
| 497 | —Cl | —H |
| 498 | —Cl | —CH$_3$ |
| 499 | —Cl | —CH$_2$CH$_3$ |
| 500 | —Cl | —CH$_2$CH$_2$CH$_3$ |
| 501 | —Cl | —C(CH$_3$)$_3$ |
| 502 | —OCH$_3$ | —H |
| 503 | —OCH$_3$ | —CH$_3$ |
| 504 | —OCH$_3$ | —CH$_2$CH$_3$ |
| 505 | —OCH$_3$ | —CH$_2$CH$_2$CH$_3$ |
| 506 | —OCH$_3$ | —C(CH$_3$)$_3$ |
| 507 | —CN | —H |
| 508 | —CN | —CH$_3$ |
| 509 | —CN | —CH$_2$CH$_3$ |
| 510 | —CN | —CH$_2$CH$_2$CH$_3$ |
| 511 | —CN | —C(CH$_3$)$_3$ |
| 512 | —F | —H |
| 513 | —F | —CH$_3$ |
| 514 | —F | —CH$_2$CH$_3$ |
| 515 | —F | —CH$_2$CH$_2$CH$_3$ |
| 516 | —F | —C(CH$_3$)$_3$ |

The compounds described above can be prepared by the procedures outlined in Schemes XIV-XVI and described in Examples 12-14 herein below.

Scheme XIV

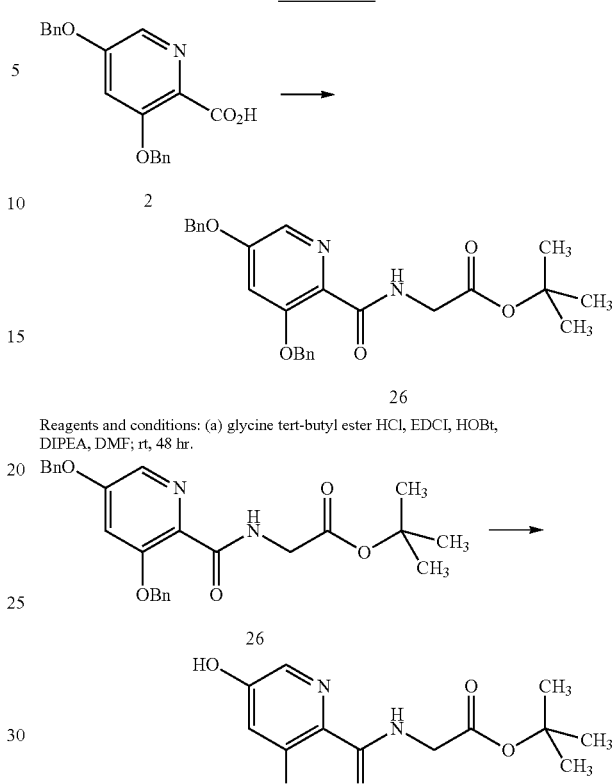

Reagents and conditions: (a) glycine tert-butyl ester HCl, EDCI, HOBt, DIPEA, DMF; rt, 48 hr.

Reagents and conditions: (b) H$_2$: Pd/C, EtOH, rt, 22 hr.

Example 12

[(3,5-Dihydroxy-pyridine-2-carbonyl)-amino]-acetic acid tert-butyl ester (27)

Preparation of [(3,5-bis-benzyloxy-pyridine-2-carbonyl)-amino]-acetic acid tert-butyl ester (26): To a solution of 3,5-bis-benzyloxy-pyridine-2-carboxylic acid, 2, (2.36 g, 6.36 mmol) in DMF (20 mL) at room temperature under N$_2$ is added 1-(3-dimethyl-aminopropyl)-3-ethylcarbodiimide (EDCI) (1.83 g, 9.54 mmol) and 1-hydroxybenzo-triazole (HOBt) (0.086 g, 0.64 mmol). The mixture is stirred for 15 minutes after which time glycine tert-butyl ester hydrochloride (1.60 g, 9.54 mmol) and diisopropylethylamine (DIPEA) (3.32 ml, 19.08 mmol) are added. The resulting solution is stirred at room temperature for 48 hours then concentrated under reduced pressure. The resulting brown oil is purified over silica (EtOAc) to afford 3.04 g (99% yield) of the desired compound as a yellow solid. $^1$H NMR (250 MHz, CDCl$_3$) δ ppm 8.19 (1H, t, J=5.2 Hz), 8.01-8.08 (2H, m), 7.27-7.54 (9H, m), 6.97 (1H, d, J=2.4 Hz), 5.24 (2H, s), 5.13 (2H, s), 4.17 (2H, d, J=5.2 Hz), 1.51 (9H, s). HPLC-MS: m/z 449 [M+H]$^+$.

Preparation of [(3,5-dihydroxy-pyridine-2-carbonyl)-amino]-acetic acid tert-butyl ester (27): A solution of [(3,5-bis-benzyloxy-pyridine-2-carbonyl)-amino]-acetic acid tert-butyl ester, 26, (3.04 g, 6.79 mmol) in EtOH (100 mL) containing 10% Pd/C (0.300 g) is stirred under an atmosphere of H$_2$ for 22 hours. The suspension is then filtered through Celite™, concentrated under reduced pressure, and the crude product purified over silica (2.5% MeOH/CH$_2$Cl$_2$) to afford 1.20 g (66% yield) of the desired compound as a colorless oil. $^1$H NMR (250 MHz, CDCl$_3$) δ ppm 11.90 (1H, br s), 8.94 (1H, br s), 8.20 (1H, t, J=5.6 Hz), 7.76 (1H, d, J=2.4 Hz), 6.77 (1H, d, J=2.1 Hz), 4.13 (2H, d, J=5.5 Hz), 1.53 (9H, s). HPLC-MS: m/z 269 [M+H]$^+$.

Scheme XV

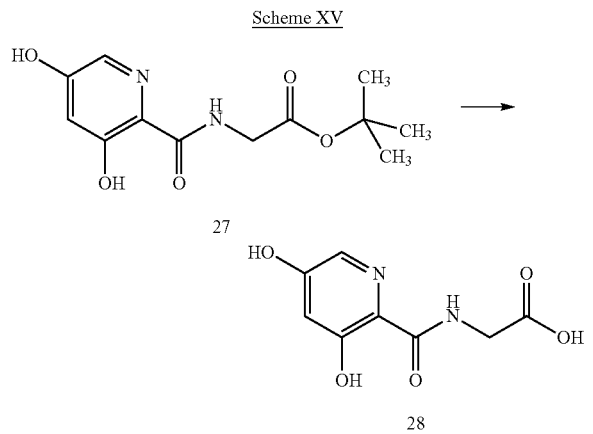

Reagents and conditions: (a) TFA, CH$_2$Cl$_2$; rt, 16 hr.

Example 13

[(3,5-Dihydroxy-pyridine-2-carbonyl)-amino]-acetic acid (29)

Preparation of [(3,5-dihydroxy-pyridine-2-carbonyl)-amino]-acetic acid (29): To a solution of [(3,5-dihydroxy-pyridine-2-carbonyl)-amino]-acetic acid tert-butyl ester, 28, (0.10 g, 0.37 mmol) in CH$_2$Cl$_2$ (4 mL) at room temperature is added trifluoroacetic acid (1 mL). The reaction is stirred for 16 hours at room temperature and then concentrated under reduced pressure. The solid that remains is collected by filtration, washed with Et$_2$O to afford 0.070 g (89% yield) of the desired compound as a colorless solid. $^1$H NMR (250 MHz, DMSO-d$_6$) δ ppm 10.86 (1H, br s), 9.00 (1H, t, J=6.1 Hz), 7.77 (1H, d, J=2.4 Hz), 6.69 (1H, d, J=2.4 Hz), 3.95 (1H, d, J=6.2 Hz). HPLC-MS: m/z 213 [M+H]$^+$.

Scheme XVI

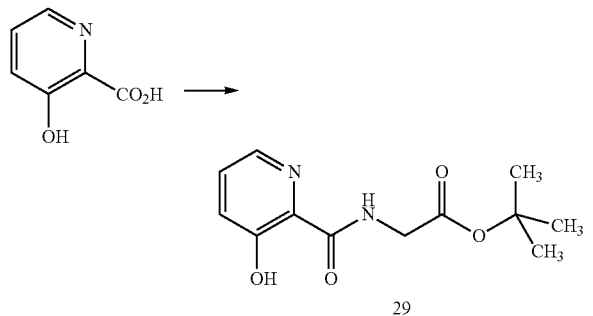

Reagents and conditions: (a) glycine tert-butyl ester HCl, EDCI, HOBt, DIPEA, DMF; rt, 3 days.

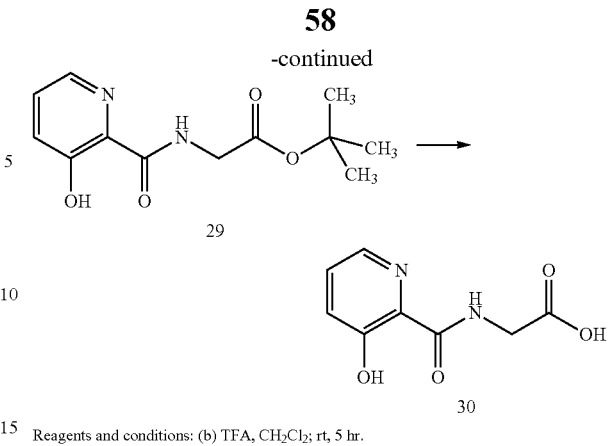

Reagents and conditions: (b) TFA, CH$_2$Cl$_2$; rt, 5 hr.

Example 14

[(3-Hydroxy-pyridine-2-carbonyl)-amino]-acetic acid (30)

Preparation of [(3-hydroxy-pyridine-2-carbonyl)-amino]-acetic acid tert-butyl ester (29): To a solution of 3-hydroxypicolinic acid (0.20 g, 1.44 mmol) in DMF (5 mL) at 0° C. under N$_2$ is added diisopropylethylamine (DIPEA) (0.75 ml, 4.3 mmol), 1-(3-dimethyl-aminopropyl)-3-ethyl-carbodiimide (EDCI) (0.412 g, 2.9 mmol) and 1-hydroxy-benzo-triazole (HOBt) (0.019 g, 0.14 mmol). The resulting mixture is stirred for 5 min before glycine tert-butyl ester HCl (0.36 g, 2.9 mmol) is introduced. The resulting solution is stirred at room temperature for 3 days then concentrated under reduced pressure. The reaction mixture is diluted with EtOAc then washed with 1M HCl, sat. NaCl, and the organic layer is dried (MgSO$_4$), filtered and concentrated under reduced pressure to a crude oil that is purified over silica (EtOAc/heptane 1:4) to afford 0.078 g (22% yield) of the desired compound as an off-white solid. $^1$H NMR (400 MHz, CDCl$_3$) δ ppm 11.80 (1H, s), 8.39 (1H, br s), 8.02 (1H, dd, J=4.4, 1.5 Hz), 7.27 (1H, dd, J=8.8, 4.4 Hz), 7.25 (1H, dd, J=8.4, 1.5 Hz), 4.06 (2H, d, J=5.5 Hz), 1.44 (9H, s). HPLC-MS: m/z 197 [M-tBu]$^+$.

Preparation of [(3-Hydroxy-pyridine-2-carbonyl)-amino]-acetic acid (30): To a solution of [(3-hydroxy-pyridine-2-carbonyl)-amino]-acetic acid tert-butyl ester, 29, (0.070 g, 0.277 mmol) in CH$_2$Cl$_2$ (4 mL) is added TFA (1 mL). The resulting solution is stirred for 5 hours then concentrated under reduced pressure to afford 0.054 g (99% yield) of the desired compound as a colorless solid. $^1$H NMR (400 MHz, MeOD) δ ppm 8.09 (1H, d, J=3.3 Hz), 7.36-7.59 (2H, m), 4.08 (2H, s). HPLC-MS: m/z 197 [M+H]$^+$.

Category VII of the present disclosure relates to compounds having the formula:

wherein non-limiting examples of R and R$^6$ are further described herein below in Table XIII.

TABLE XIII

| No. | R | R⁶ |
|---|---|---|
| 517 | 3-fluorophenyl | —H |
| 518 | 4-fluorophenyl | —H |
| 519 | 3-chlorophenyl | —H |
| 520 | 4-chlorophenyl | —H |
| 521 | 3-cyanophenyl | —H |
| 522 | 4-cyanophenyl | —H |
| 523 | 3-methylphenyl | —H |
| 524 | 4-methylphenyl | —H |
| 525 | 3-ethylphenyl | —H |
| 526 | 4-ethylphenyl | —H |
| 527 | 3-methoxyphenyl | —H |
| 528 | 4-methoxyphenyl | —H |
| 529 | 3-ethoxyphenyl | —H |
| 530 | 4-ethoxyphenyl | —H |
| 531 | 3-fluorophenyl | —CH₃ |
| 532 | 4-fluorophenyl | —CH₃ |
| 533 | 3-chlorophenyl | —CH₃ |
| 534 | 4-chlorophenyl | —CH₃ |
| 535 | 3-cyanophenyl | —CH₃ |
| 536 | 4-cyanophenyl | —CH₃ |
| 537 | 3-methylphenyl | —CH₃CH₃ |
| 538 | 4-methylphenyl | —CH₃ |
| 539 | 3-ethylphenyl | —CH₃ |
| 540 | 4-ethylphenyl | —CH₃ |
| 541 | 3-methoxyphenyl | —CH₃ |
| 542 | 4-methoxyphenyl | —CH₃ |
| 543 | 3-ethoxyphenyl | —CH₃ |
| 544 | 4-ethoxyphenyl | —CH₃ |
| 545 | 3-fluorophenyl | —CH₂CH₃ |
| 546 | 4-fluorophenyl | —CH₂CH₃ |
| 547 | 3-chlorophenyl | —CH₂CH₃ |
| 548 | 4-chlorophenyl | —CH₂CH₃ |
| 549 | 3-cyanophenyl | —CH₂CH₃ |
| 550 | 4-cyanophenyl | —CH₂CH₃ |
| 551 | 3-methylphenyl | —CH₂CH₃ |
| 552 | 4-methylphenyl | —CH₂CH₃ |
| 553 | 3-ethylphenyl | —CH₂CH₃ |
| 554 | 4-ethylphenyl | —CH₂CH₃ |
| 555 | 3-methoxyphenyl | —CH₂CH₃ |
| 556 | 4-methoxyphenyl | —CH₂CH₃ |
| 557 | 3-ethoxyphenyl | —CH₂CH₃ |
| 558 | 4-ethoxyphenyl | —CH₂CH₃ |

The compounds which encompass Category VII of the present disclosure can be prepared by the procedures outlined in Schemes XVII and XVIII and described in Examples 15 and 16 herein below.

Scheme XVII

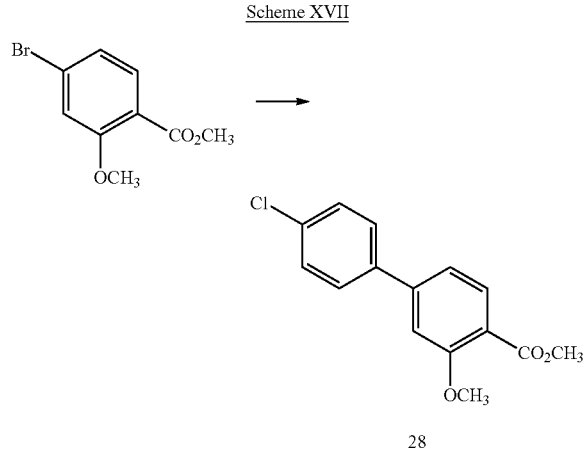

Reagents and conditions: (a) (4-ClC₆H₄)B(OH)₂, Pd(dppf)Cl₂, K₃PO₄, 1,4-dioxane, MeOH; 80° C., 3 hr.

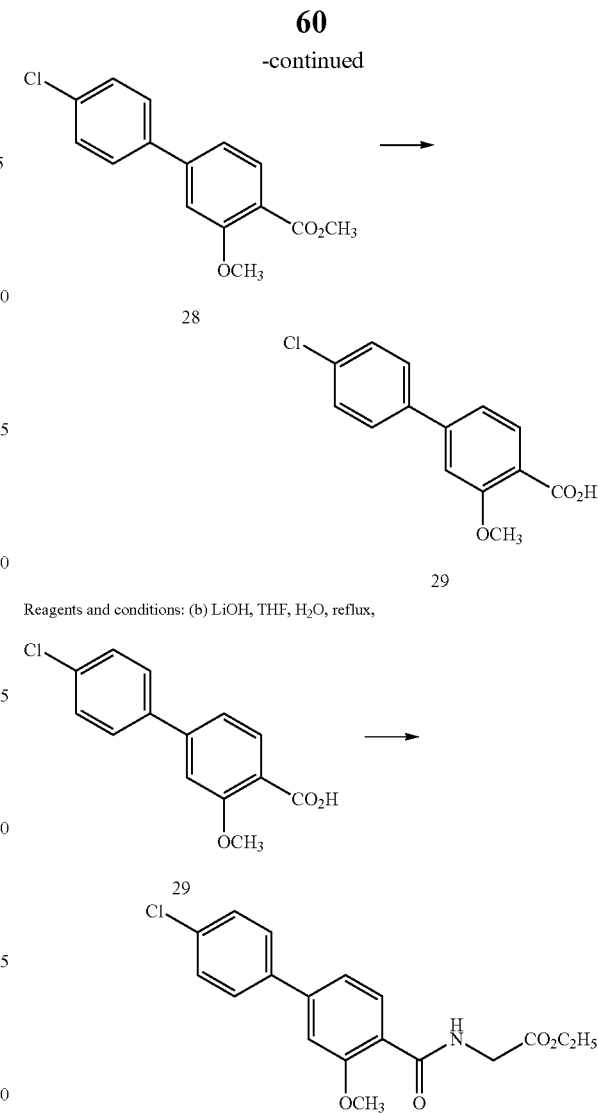

Reagents and conditions: (b) LiOH, THF, H₂O, reflux,

Reagents and conditions: (c) GlyOEt•HCl, EDCI, HOBt, DIPEA, DMF, CH₂Cl₂; rt,

Example 15

3-Methoxy-4'-methyl-biphenyl-4-carboxylic acid methyl ester (30)

Preparation of 4'-chloro-3-methoxy-biphenyl-4-carboxylic acid methyl ester (28): To a degassed solution of methyl 4-bromo-2-methoxybenzoate (0.70 g, 2.86 mmol) in 1,4-dioxane (10 mL) and MeOH (2.5 mL) is added 4-chlorophenyl boronic acid (0.536 g, 3.43 mmol), Pd(dppf)Cl₂ (0.233 g, 0.286 mmol) and K₃PO₄ (0.728 g, 3.43 mmol). The resulting suspension is heated to 80° C. and stirred for 3 hours. After this time, the reaction is cooled to room temperature and filtered through Celite™. The solids that form are collected and washed with additional MeOH before the filtrate is concentrated under reduced pressure. The crude material is purified over silica (hexanes:EtOAc; 6:1 to 4:1) to provide 0.615 g (78% yield) of the desired compound as orange crystals. ¹H NMR (400 MHz, CDCl₃) δ ppm 7.89 (1H, d, J=8.0 Hz), 7.52-7.56 (2H, m), 7.44 (2H, d, J=8.7 Hz), 7.17 (1H, d, J=8.0 Hz), 7.12 (1H, d, J=1.6 Hz), 3.99 (3H, s), 3.92 (3H, s). HPLC-MS: m/z 277 [M+H]⁺.

Scheme XVIII

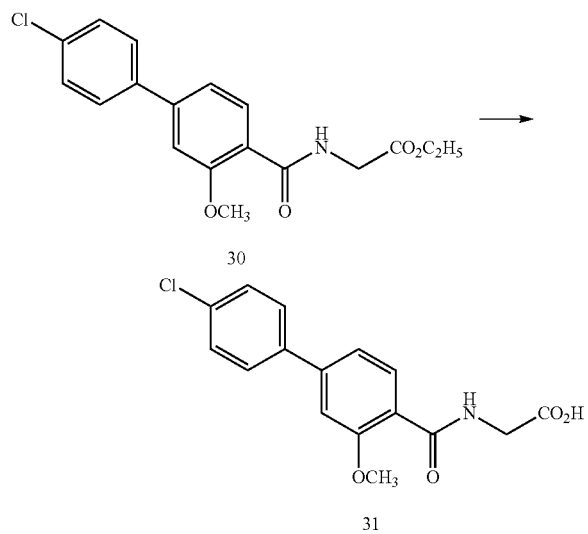

Reagents and conditions: (a) LiOH, THF, H₂O; reflux, 2 hr.

Example 16

4'-Chloro-3-methoxy-biphenyl-4-carboxylic acid

Preparation of 4'-chloro-3-methoxy-biphenyl-4-carboxylic acid (31): To a solution of 4'-chloro-3-methoxy-biphenyl-4-carboxylic acid methyl ester, 30, (0.615 g, 2.22 mmol) in THF (20 mL) and H₂O (5 mL) is added LiOH (0.932 g, 22.2 mmol). The resulting suspension is heated to reflux for 2 hours. The reaction is cooled and concentrated under reduced pressure. The crude product is acidified using conc. HCl and the resulting solid is collected by filtration, washed with H₂O to afford 0.532 g (91% yield) of the desired compound as a grey solid. ¹H NMR (400 MHz, CDCl₃) δ ppm 10.69 (1H, br s), 8.26 (1H, d, J=8.1 Hz), 7.53 — 7.58 (2H, m), 7.44 — 7.50 (2H, m), 7.33 (1H, dd, J=8.1, 1.6 Hz), 7.20 (1H, d, J=1.3 Hz), 4.17 (3H, s). HPLC-MS: m/z 263 [M+H]⁺.

The following are non-limiting examples of additional compounds of Formula (I).

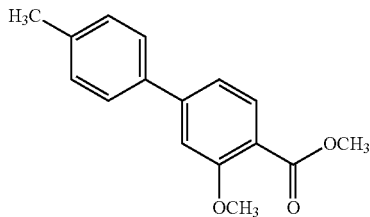

3-Methoxy-4'-methyl-biphenyl-4-carboxylic acid methyl ester: ¹H NMR (250 MHz, CDCl₃) δ ppm 7.89 (1H, d, J=7.9 Hz), 7.52 (2H, d, J=8.2 Hz), 7.25-7.32 (2H, m), 7.15-7.24 (2H, m), 3.99 (3H, s), 3.92 (3H, s), 2.42 (3H, s). HPLC-MS: m/z 257 [M+H]⁺.

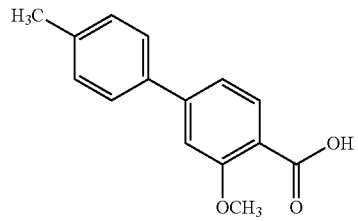 [SMILES: COc1cc(-c2ccc(C)cc2)ccc1C(=O)O]

3-Methoxy-4'-methyl-biphenyl-4-carboxylic acid: ¹H NMR (400 MHz, CDCl₃) δ ppm 10.74 (1H, br s), 8.24 (1H, d, J=8.1 Hz), 7.52 (2H, d, J=8.1 Hz), 7.36 (1H, dd, J=8.1, 1.5 Hz), 7.30 (2H, d, J=7.9 Hz), 7.23 (1H, d, J=1.4 Hz), 4.16 (3H, s), 2.43 (3H, s). HPLC-MS: m/z 243 [M+H]⁺.

Additional compounds of Formula (I) the formula:

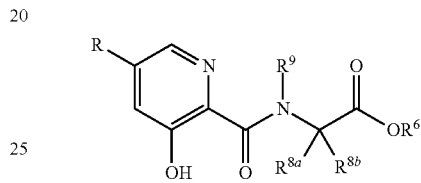

wherein non-limiting examples of $R^{8a}$, $R^{8b}$, $R^9$ and $R^6$ are further described herein below in Table.

TABLE XIV

| No. | R | $R^6$ | $R^{8a}$ | $R^{8b}$ | $R^9$ |
|---|---|---|---|---|---|
| 559 | 3-chlorophenyl | —H | —CH₃ | —H | —H |
| 560 | 3-chlorophenyl | —CH₃ | —CH₃ | —H | —H |
| 561 | 3-chlorophenyl | —H | —CH₃ | —CH₃ | —H |
| 562 | 3-chlorophenyl | —CH₃ | —CH₃ | —CH₃ | —H |
| 563 | 3-chlorophenyl | —H | —CH₃ | —CH₃ | —CH₃ |
| 564 | 3-chlorophenyl | —CH₃ | —CH₃ | —CH₃ | —CH₃ |
| 565 | 4-chlorophenyl | —H | —CH₃ | —H | —H |
| 566 | 4-chlorophenyl | —CH₃ | —CH₃ | —H | —H |
| 567 | 4-chlorophenyl | —H | —CH₃ | —CH₃ | —H |
| 568 | 4-chlorophenyl | —CH₃ | —CH₃ | —CH₃ | —H |
| 569 | 4-chlorophenyl | —H | —CH₃ | —CH₃ | —CH₃ |
| 570 | 4-chlorophenyl | —CH₃ | —CH₃ | —CH₃ | —CH₃ |
| 571 | 4-methylphenyl | —H | —CH₃ | —H | —H |
| 572 | 4-methylphenyl | —CH₃ | —CH₃ | —H | —H |
| 573 | 4-methylphenyl | —H | —CH₃ | —CH₃ | —H |
| 574 | 4-methylphenyl | —CH₃ | —CH₃ | —CH₃ | —H |
| 575 | 4-methylphenyl | —H | —CH₃ | —CH₃ | —CH₃ |
| 576 | 4-methylphenyl | —CH₃ | —CH₃ | —CH₃ | —CH₃ |

The compounds described above can be prepared by the procedures outlined herein below in Schemes XIX and XX and described in Examples 17 and 18 herein below.

Scheme XIX

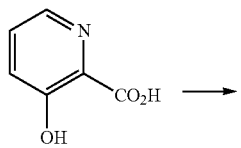

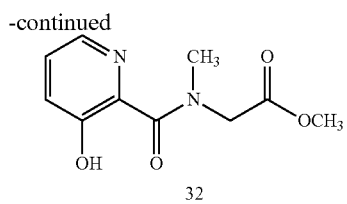

32

Reagents and conditions: (a) 2-(N-methylamino)acetic acid ester HCl, EDCI, HOBt, DIPEA, DMF; rt, 32 hr.

Example 17

[(3-Hydroxy-pyridine-2-carbonyl)-methyl-amino]-acetic acid ethyl ester (32)

Preparation of [(3-hydroxy-pyridine-2-carbonyl)methylamino]acetic acid ethyl ester (31): To a solution of 3-hydroxy picolinic acid (0.40 g, 2.88 mmol) in DMF (5 mL) is added diisopropylethylamine (DIPEA) (1.50 ml, 8.63 mmol), 1-(3-dimethylamino-propyl)-3-ethylcarbodiimide (EDCI) (0.825 g, 4.31 mmol) and 1-hydroxybenzotriazole (HOBt) (0.039 g, 0.29 mmol). The reaction mixture is stirred for 5 minutes then methylamino-acetic acid ester hydrochloride (0.663 g, 4.31 mmol) is added. The reaction is stirred at room temperature for 32 hours after which the solvent is removed under reduced pressure. The residue is partitioned between EtOAc and 1M HCl and the organic layer separated, dried (MgSO$_4$), filtered and concentrated under reduced pressure. The crude material is purified over silica (EtOAc:hexanes 1:1) to afford 0.10 g (15% yield) of the desired compound as a colourless solid. HPLC-MS: m/z 240 [M+H]$^+$.

Scheme XX

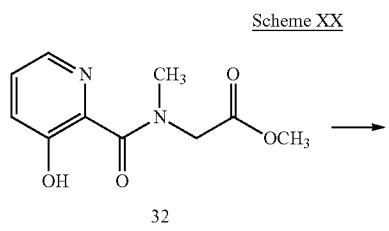

Reagents and conditions: (a) NaOH, THF, H$_2$O; reflux, 3 hr.

Example 18

[(3-Hydroxy-pyridine-2-carbonyl)-methyl-amino]-acetic acid (33)

Preparation of [(3-hydroxy-pyridine-2-carbonyl)-methyl-amino]-acetic acid (33): To a solution of [(3-hydroxy-pyridine-2-carbonyl)methylamino]acetic acid ethyl ester, 32, (0.10 g, 0.42 mmol) in THF (4 mL) is added H$_2$O (1 mL) and NaOH (0.90 g, 2.25 mmol). The reaction is stirred for 3 hours then concentrated under reduced pressure. The remaining oil is acidified to pH ~1 with 1M HCl and the solution is concentrated under reduced pressure to give an off-white solid. The solid is suspended in CHCl$_3$:isopropanol (1:1) then collected by filtration. The solid is washed with additional CHCl$_3$:isopropanol (1:1) then transferred to a flask and triturated with Et$_2$O to afford 0.075 g (85% yield) of the desired compound as a pale yellow solid. $^1$H NMR (250 MHz, MeOD) δ ppm (rotamers) 8.26 (1H, br s), 7.63-7.74 (1H, m), 7.56-7.63 (1H, m), 4.38 (1H, s), 4.32 (1H, s), 3.20 (1.5H, s), 3.12 (1.5H, s). HPLC-MS: m/z 211 [M+H]$^+$.

The following are non-limiting examples of the compounds described above.

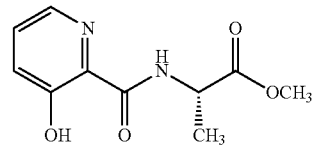 [SMILES: COC(=O)[C@H](C)NC(=O)c1ncccc1O]

2-(S)-[(3-Hydroxy-pyridine-2-carbonyl)-amino]-propionic acid methyl ester: $^1$H NMR (250 MHz, CDCl$_3$) δ ppm 11.86 (1H, s), 8.47 (1H, br s), 8.10 (1H, dd, J=4.1, 1.7 Hz), 7.28-7.43 (2H, m), 4.63-4.84 (1H, m), 3.81 (3H, s), 1.57 (3H, d, J=7.3 Hz). HPLC-MS: m/z 225 [M+H]$^+$.

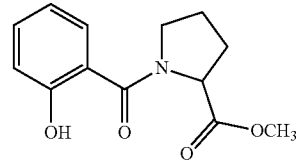 [SMILES: COC(=O)C1CCCN1C(=O)c1ccccc1O]

1-(3-Hydroxy-pyridine-2-carbonyl)-pyrrolidine-2-carboxylic acid methyl ester: $^1$H NMR (250 MHz, CDCl$_3$) δ ppm (rotamers) 12.86 (0.67H, br s), 12.44 (0.33H, br s), 8.14 (0.33H, t, J=2.9 Hz), 7.98 (0.67H, dd, J=3.7, 2.1 Hz), 7.24-7.31 (2H, m), 5.38 (0.67H, dd, J=8.5, 3.4 Hz), 4.63-4.75 (0.33H, m), 4.37 (0.67H, t, J=6.7 Hz), 3.80-4.01 (1.33H, m), 3.79 (1H, s), 3.70 (2H, s), 1.87-2.44 (4H, m). HPLC-MS: m/z 251 [M+H]$^+$.

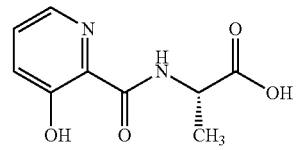

2S-[(3-Hydroxy-pyridine-2-carbonyl)-amino]-propionic acid: $^1$H NMR (250 MHz, DMSO-d$_6$) δ ppm 12.87 (1H, br s), 12.28 (1H, s), 9.19 (1H, d, J=7.5 Hz), 8.19 (1H, dd, J=4.3, 1.4 Hz), 7.50-7.65 (1H, m), 7.37-7.49 (1H, m), 3.95-4.95 (1H, m), 1.45 (3H, d, J=7.3 Hz). HPLC-MS: m/z 211 [M+H]$^+$.

Administration of one or more of the compounds of Formula (I), alone in the form of pharmaceutical compositions, optionally in combination with other pharmaceutically active compounds or compositions, can be effective in treatment of the following disease states or conditions:

i) as human protein HIF-1α prolyl hydroxylase inhibitors; and thereby providing a means for regulating blood flow, oxygen delivery and energy utilization in ischemic tissues;

ii) the compounds of the present disclosure are efficacious in regulating blood flow, oxygen delivery and energy utilization in ischemic tissues; and iii) the compounds of the present disclosure provide stabilized HIF-1α by blocking a degradation pathway mediated by HIF prolyl hydroxylase.

Each of the disease states or conditions which the formulator desires to treat may require differing levels or amounts of the compounds described herein to obtain a therapeutic level. The formulator can determine this amount by any of the testing procedures known to the artisan or ordinary skil in the art.

The compounds of the present disclosure can be HIF-1α prolyl hydroxylase inhibitors when administered in pharmaceutically effective amounts, and thereby provide increased angiogenic response or cellular responses which are activated by transcription factors that are directly or indirectly affected by an increase in cellular HIF-1α concentration. Non-limiting examples of these diseases or disease states are listed herein below, inter alia, Peripheral Vascular Disease (PVD), Coronary Artery Disease (CAD), heart failure, ischemia, and anemia. The compounds disclosed herein are especially effective in the treatment of anemia.

Stimulation of EPO production: anemia

HIF-1 is a transcription factor that also regulates the hypoxia-inducible EPO gene. HIF-1 binding is required for EPO transcriptional activation in response to hypoxia (Semenza, G. L., "Regulation of erythropoietin production: New insights into molecular mechanisms of oxygen homeostasis", *Hematol. Oncol. Clin. North Am.*, Vol. 8, pp. 863-884 (1994)). In particular, HIF-1α binds to the 3' hypoxia-response element of the EPO gene which results in the marked enhancement of EPO transcription (Semenza, G. L., et al. "Transcriptional regulation of genes encoding glycolytic enzymes by hypoxia-inducible factor 1", *J. Biol. Chem., Vol.* 269, pp. 23757-63 (1994)). EPO, in turn, is essential for maintenance of red blood cells by controlling the proliferation and differentiation of erythroid progenitor cells into red blood cells (Krantz, S. B., "Erythropoietin," Blood, Vol. 77, pp 419-434 (1991)). During fetal development, the liver serves as the primary source of EPO. Shortly before birth, production of EPO in the liver decreases and the kidney becomes the primary source of EPO. However, in adults other organs such as the liver and brain produce small but significant amounts of EPO. A erythropoietin deficiency is associated with anemia. In humans, the most prevalent form of anemia is associated with kidney failure.

EPO has been described in the treatment of anemia: associated with chemotherapy; that occurs as a consequence of AIDS; and due to prematurity and autologous blood donation. EPO has even been suggested as a general use agent in pre-operative elective surgery.

Angiogenesis

Angiogenesis, the sprouting of new blood vessels from the pre-existing vasculature, plays a crucial role in a wide range of physiological and pathological processes (Nguyen, L. L. et al., *Int. Rev. Cytol.,* 204, 1-48, (2001). Angiogenesis is a complex process, mediated by communication between the endothelial cells that line blood vessels and their surrounding environment. In the early stages of angiogenesis, tissue or tumor cells produce and secrete pro-angiogenic growth factors in response to environmental stimuli such as hypoxia. These factors diffuse to nearby endothelial cells and stimulate receptors that lead to the production and secretion of proteases that degrade the surrounding extracellular matrix. The activated endothelial cells begin to migrate and proliferate into the surrounding tissue toward the source of these growth factors (Bussolino, F., *Trends Biochem. Sci.,* 22, 251-256, (1997)). Endothelial cells then stop proliferating and differentiate into tubular structures, which is the first step in the formation of stable, mature blood vessels. Subsequently, periendothelial cells, such as pericytes and smooth muscle cells, are recruited to the newly formed vessel in a further step toward vessel maturation.

Angiogenesis is regulated by a balance of naturally occurring pro- and anti-angiogenic factors. Vascular endothelial growth factor, fibroblast growth factor, and angiopoeitin represent a few of the many potential pro-angiogenic growth factors. These ligands bind to their respective receptor tyrosine kinases on the endothelial cell surface and transduce signals that promote cell migration and proliferation. Whereas many regulatory factors have been identified, the molecular mechanisms of this process are still not fully understood.

There are many disease states driven by persistent unregulated or improperly regulated angiogenesis. In such disease states, unregulated or improperly regulated angiogenesis may either cause a particular disease or exacerbate an existing pathological condition. For example, ocular neovascularization has been implicated as the most common cause of blindness and underlies the pathology of approximately 20 eye diseases. In certain previously existing conditions such as arthritis, newly formed capillary blood vessels invade the joints and destroy cartilage. In diabetes, new capillaries formed in the retina invade the vitreous humor, causing bleeding and blindness.

Both the growth and metastasis of solid tumors are also angiogenesis-dependent (Folkman et al., "Tumor Angiogenesis," Chapter 10, 206-32, in The Molecular Basis of Cancer, Mendelsohn et al., eds., W. B. Saunders, (1995)). It has been shown that tumors which enlarge to greater than 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner, *New Eng. J. Med.,* 324, 1, 1-8 (1991). When used as drugs in tumor-bearing animals, natural inhibitors of angiogenesis may prevent the growth of small tumors (O'Reilly et al., *Cell,* 79, 315-28 (1994). In some protocols, the application of such inhibitors leads to tumor regression and dormancy even after cessation of treatment (O'Reilly et al., *Cell,* 88, 277-85 (1997)). Moreover, supplying inhibitors of angiogenesis to certain tumors may potentiate their response to other therapeutic regimens (Teischer et al., *Int. J. Cancer,* 57, 920-25 (1994)).

Peripheral Vascular Disease

Peripheral vascular disease (PVD) is the term used to describe the clinical syndrome of vascular insufficiency outside of the coronary circulation and typically involving the circulation to the lower extremities. There are an estimated 8-12 million patients in the US with peripheral vascular disease; another 16.5 million undiagnosed. Atherosclerosis is by far the leading cause of peripheral vascular disease (PVD), although a number of discrete disease processes can contribute to its development and progression (i.e. diabetes, immune vasculitis and trauma). Atherosclerotic PVD can present in three ways:

1) Asymptomatic PVD diagnosed on the basis of noninvasive testing (usually physical exam);
2) Intermittent claudication with symptoms of leg pain with exercise; and 3) Critical limb ischemia with leg pain at rest and limb-threatening ischemic changes (usually non-healing or infected cutaneous ulcerations).

The age-adjusted (average age 66 years) prevalence of PVD in the US population is approximately 12%. Of those patients with claudication, 20-30% will have progressive symptoms and 10% will require amputation for critical limb ischemia. Although patients with symptomatic PVD suffer significant decreases in mobility, muscle mass, bone density and quality of life, there are currently no effective medical therapies available.

The present disclosure provides compounds which when administered in vivo inhibit HIF-1α prolyl hydroxylase thereby leading to increased expression of HIF-regulated genes, inter alia, angiogenic factors, erythropoietin, and glycolytic enzymes thereby resulting in improvement in blood flow, oxygen delivery and energy utilization in ischemic tissues.

Although many disease states are driven by persistent unregulated or improperly regulated angiogenesis, some disease states could be treated by increased angiogenesis. Tissue growth and repair are biologic events wherein cellular proliferation and angiogenesis occur. Thus an important aspect of wound repair is the revascularization of damaged tissue by angiogenesis.

Wounds

Chronic, non-healing wounds are a major cause of prolonged morbidity in the aged human population. This is especially the case in bedridden or diabetic patients who develop severe, non-healing skin ulcers. In many of these cases, the delay in healing is a result of inadequate blood supply either as a result of continuous pressure or of vascular blockage. Poor capillary circulation due to small artery atherosclerosis or venous stasis contributes to the failure to repair damaged tissue. Such tissues are often infected with microorganisms that proliferate unchallenged by the innate defense systems of the body which require well vascularized tissue to effectively eliminate pathogenic organisms. As a result, most therapeutic intervention centers on restoring blood flow to ischemic tissues thereby allowing nutrients and immunological factors access to the site of the wound.

Atherosclerotic Lesions

Atherosclerotic lesions in large vessels may cause tissue ischemia that could be ameliorated by modulating blood vessel growth to the affected tissue. For example, atherosclerotic lesions in the coronary arteries may cause angina and myocardial infarction that could be prevented if one could restore blood flow by stimulating the growth of collateral arteries. Similarly, atherosclerotic lesions in the large arteries that supply the legs may cause ischemia in the skeletal muscle that limits mobility and in some cases necessitates amputation, which may also be prevented by improving blood flow with angiogenic therapy.

Diabetes/Hypertension

Diseases such as diabetes and hypertension are characterized by a decrease in the number and density of small blood vessels such as arterioles and capillaries. These small blood vessels are important for the delivery of oxygen and nutrients. A decrease in the number and density of these vessels contributes to the adverse consequences of hypertension and diabetes including claudication, ischemic ulcers, accelerated hypertension, and renal failure. These common disorders and many other less common ailments, such as Burgers disease, could be ameliorated by increasing the number and density of small blood vessels using angiogenic therapy.

The present disclosure further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Formulations

The present disclosure also relates to compositions or formulations which comprise the human protein HIF-1α prolyl hydroxylase inhibitors according to the present disclosure. In general, the compositions of the present disclosure comprise:

a) an effective amount of one or more human protein HIF-1α prolyl hydroxylase inhibitor according to the present disclosure which are effective for treating PVD, CAD, heart failure, ischemia, and anemia; and b) one or more excipients.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

Non-limiting examples of compositions according to the present disclosure include:

a) from about 0.001 mg to about 1000 mg of one or more human protein HIF-1α prolyl hydroxylase inhibitor according to the present disclosure; and b) one or more excipients.

Another example according to the present disclosure relates to the following compositions:

a) from about 0.01 mg to about 100 mg of one or more human protein prolyl HIF-1α prolyl hydroxylase inhibitor according to the present disclosure; and b) one or more excipients.

A further example according to the present disclosure relates to the following compositions:

a) from about 0.1 mg to about 10 mg of one or more human protein HIF-1α prolyl hydroxylase inhibitor according to the present disclosure; and b) one or more excipients.

The term "effective amount" as used herein means "an amount of one or more HIF-1α prolyl hydroxylase inhibitors, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present disclosure can be administered as frequently as necessary to achieve a therapeutic amount.

The present disclosure further relates to the use of one or more of the HIF-1α prolyl hydroxylase inhibitors disclosed herein for making a medicament for treating anemia.

The present disclosure further relates to the use of one or more of the HIF-1α prolyl hydroxylase inhibitors disclosed herein for making a medicament for treating angiogenesis.

The present disclosure further relates to the use of one or more of the HIF-1α prolyl hydroxylase inhibitors disclosed herein for making a medicament for treating peripheral vascular disease.

The present disclosure further relates to the use of one or more of the HIF-1α prolyl hydroxylase inhibitors disclosed herein for making a medicament for treating wounds.

The present disclosure further relates to the use of one or more of the HIF-1α prolyl hydroxylase inhibitors disclosed herein for making a medicament for treating atherosclerotic lesions.

The present disclosure further relates to the use of one or more of the HIF-1α prolyl hydroxylase inhibitors disclosed herein for making a medicament for treating diabetes.

The present disclosure further relates to the use of one or more of the HIF-1α prolyl hydroxylase inhibitors disclosed herein for making a medicament for treating hypertension.

The present disclosure further relates to the use of one or more of the HIF-1α prolyl hydroxylase inhibitors disclosed herein for making a medicament for treating a disease affected by the level of VEGF, GAPDH and erythropoietin.

The present disclosure further relates to the use of one or more of the HIF-1α prolyl hydroxylase inhibitors disclosed herein for making a medicament for treating a disorder chosen from Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors and acquired immune deficiency syndrome.

The present disclosure further relates to the use of one or more of the HIF-1α prolyl hydroxylase inhibitors disclosed herein for making a medicament for treating a disorder chosen from diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndrome, toxoplasmosis, trauma and post-laser complications, diseases associated with rubeosis, and proliferative vitreoretinopathy.

Method of Use

By increasing the transcription of these HIF-1 target genes, the HIF-1α prolyl hydroxylase inhibitors of the present disclosure provide a method for increasing the vascularization of tissue in a subject. As used herein, "vascularization of tissue" means a pro-angiogenic response whereby blood vessels or other vessels or ducts develop at or around the afflicted tissue. The afflicted tissue need not be hypoxic or ischemic per se, but rather the HIF-1α prolyl hydroxylase inhibitors help to sustain or further stimulate the body's pro-angiogenic response to hypoxia. A non-limiting example of "vascularization" includes capillary proliferation in a non-healing wound or along the border of ischemic tissue. Thus, these compounds enhance the ability of the body to revascularize damaged tissues or increase vasculature (e.g. to prevent hypoxic damage). Non-limiting examples of "tissue" include: cardiac tissue, such as myocardium and cardiac ventricles; skeletal muscle; neurological tissue, such as from the cerebellum; internal organs, such as the stomach, intestine, pancreas, liver, spleen, and lung; and distal appendages such as fingers and toes.

Stimulated by a build up of the cellular concentration of HIF-1α is the production of Vascular Endothelial Growth Factor (VEGF) which is known for its ability to induce vascular leakage. Oxygen tension has been shown to be a key regulator of VEGF gene expression, both in vitro and in vivo. During VEGF induction it is demonstrated that VEGF induces the formation of functional neo-vessels in the mouse cornea and enhanced blood flow in a dog model of coronary artery disease. The HIF-1α prolyl hydroxylase inhibitors of the present disclosure provide enhancement in the expression of multiple hypoxia inducible genes including VEGF, GAPDH and erythropoietin (EPO). Additionally, the HIF-1α prolyl hydroxylase inhibitors of the present disclosure provide enhanced the accumulation of HIF1-α in the cytoplasm and nucleus. Transgenic mice expressing a constitutively active HIF-1α in the skin have increased dermal vascularity and had a 13-fold increase in VEGF levels The present disclosure also relates to a method for controlling human protein HIF1α prolyl hydroxylase. The present method comprises the step of administering to a human or higher mammal an effective amount of a composition comprising one or more human protein HIF-1α prolyl hydroxylase inhibitors according to the present disclosure.

The present disclosure also relates to the use of the human protein HIF-1α prolyl hydroxylase inhibitors according to the present disclosure in the manufacture of a medicament for the treatment of atrial arrhythmias and related disorders. The present disclosure also relates to hypoxia inducible factor HIF-1α prolyl hydroxylase inhibition in myocardial remodeling and function, thereby providing means for inducing angiogenesis in a patient experiencing ischemia.

The present disclosure relates to a method for treating anemia comprising administering to a human or mammal in need of treatment an effective amount of one or more human protein HIF-1α prolyl hydroxylase inhibitors according to the present disclosure.

The present disclosure relates to a method for regulating anemia comprising administering to a human or mammal in need of treatment an effective amount of one or more human protein HIF-1α prolyl hydroxylase inhibitors according to the present disclosure.

The present disclosure relates to a method for preventing anemia comprising administering to a human or mammal in need of treatment an effective amount of one or more human protein HIF-1α prolyl hydroxylase inhibitors according to the present disclosure.

Procedures

EGLN-1 Activity Assay

The EGLN-1 (or EGLN-3) enzyme activity is determined using mass spectrometry (matrix-assisted laser desorption ionization, time-of-flight MS, MALDI-TOF MS- for assay details, see reference (Greis et al., 2006). Recombinant human EGLN-1-179/426 is prepared as described above and in the Supplemental Data. Full-length recombinant human EGLN-3 is prepared in a similar way, however it is necessary to use the His-MBP-TVMVEGLN-3 fusion for the assay due to the instability of the cleaved protein. For both enzymes, the HIF-1a peptide corresponding to residues 556-574 (DLDLEALAPYIPADDDFQL) (SEQ ID NO. 1) is used as substrate. The reaction is conducted in a total volume of 50 uL containing TrisCl (5 mM, pH 7.5), ascorbate (120 µM), 2-oxoglutarate (3.2 µM), HIF-1α (8.6 µM), and bovine serum albumin (0.01%). The enzyme, quantity predetermined to hydroxylate 20% of substrate in 20 minutes, is added to start the reaction. Where inhibitors are used, compounds are prepared in dimethyl sulfoxide at 10-fold final assay concentration. After 20 minutes at room temperature, the reaction is stopped by transferring 10 µL of reaction mixture to 50 µL of a mass spectrometry matrix solution (α-cyano-4-hydroxycinnamic acid, 5 mg/mL in 50% acetonitrile/0.1% TFA, 5 mM $NH_4PO_4$). Two microliters of the mixture is spotted onto a MALDI-TOF MS target plate for analysis with an Applied Biosystems (Foster City, CA) 4700 Proteomics Analyzer MALDI-TOF MS equipped with a Nd:YAG laser (355 nm, 3 ns pulse width, 200 Hz repetition rate). Hydroxylated peptide product is identified from substrate by the gain of 16 Da. Data defined as percent conversion of substrate to product is analyzed in GraphPad Prism 4 to calculate $IC_{50}$ values.

VEGF ELISA Assay

HEK293 cells are seeded in 96-well poly-lysine coated plates at 20,000 cells per well in DMEM (10% FBS, 1% NEAA, 0.1% glutamine). Following overnight incubation, the cells are washed with 100 uL of Opti-MEM (Gibco, Carlsbad, CA) to remove serum. Compound in DMSO is serially diluted (beginning with 100 µM) in Opti-MEM and added to the cells. The conditioned media is analyzed for VEGF with a Quantikine human VEGF immunoassay kit (R&D Systems, Minneapolis, MN). Optical density measurements at 450 nm are recorded using the Spectra Max 250 (Molecular Devices, Sunnyvale, CA). Data defined as % of DFO stimulation is used to calculate $EC_{50}$ values with GraphPad Prism 4 software (San Diego, CA).

Mouse Ischemic Hindlimb Study

All animal work is conducted in accordance with the Guide for the Care and Use of Laboratory Animals (National Academy of Sciences; Copyright 01996) and the Institutional Animal Care and Use Committee guidelines at Procter and Gamble Pharmaceuticals. We studied 9-10 week old male C57Bl/6 mice from Charles River Laboratory (Portage, MI). The mice are orally dosed with vehicle (aqueous carbonate buffer, 50 mM; pH 9.0) or compound 1 in vehicle at 50 mg/kg or 100 mg/kg. The animals are dosed three times: day 1 at 8 am and 5 pm, day 2 at 8 am. One hour after the first dose, unilateral arterial ligation is performed under anesthesia using isoflurane. The femoral artery is ligated proximal to the origin of the popliteal artery. The contralateral limb underwent a sham surgical procedure. Ligation is performed in an alternating fashion between right and left hindlimbs. Two hours after 8 am dosing on day 2, we obtained blood by ventricular stick while the mice are anesthetized with isoflurane. Serum samples for EPO analysis are obtained using gel clot serum separation tubes. Heart, liver, and gastrocnemius muscles are harvested, snap-frozen in liquid nitrogen, and stored in −80° C. until use.

Mouse Serum EPO Assay

The mouse serum EPO is detected using Mouse Quantikine Erythropoietin ELISA kit from R&D Systems according to manufacturer's instructions.

Mouse Tissue HIF Western Blot Analysis

Tissues from mice stored at −80° C. are powdered with mortar and pestle chilled with liquid nitrogen. Nuclear extracts are prepared using an NE-PER kit (Pierce Biotechnology). For immunoprecipitation, nuclear extract is added to monoclonal antibody to HIF-1α (Novus, Littleton, CO) at a tissue to antibody ratio of 200:1. The suspension is incubated in a conical micro centrifuge tube for 4 hours at 4° C. Protein A/G-coupled agarose beads (40 ul of a 50% suspension) are then added to the tube. Following overnight tumbling at 4° C., the beads are washed 3 times with ice-cold phosphate buffered saline. The beads are then prepared for SDS-PAGE with 40 ul of Laemmli sample buffer. Proteins separated on SDS-PAGE are transferred onto nitrocellulose sheets with XCell-II Blot Module system (Invitrogen, Carlsbad, CA). The blots are blocked with 5% BSA prior to incubation with a rabbit antibody to HIF-1α at 1:100 dilution (Novus). The blots are then washed with Tris-buffered saline/Tween-20 buffer and incubated with horseradish peroxidase-conjugated goat anti-rabbit secondary antibody (Pierce, Rockford, IL). Blots are developed with the ECL reagent (Amersham, Piscataway, NJ). Images of blots are captured with an Epson Expression 1600 scanner.

Table XV below provides non-limiting examples of the in vivo response for compounds according to the present disclosure.

TABLE XV

| Compound | EGLIN1 $IC_{50}$ µM | EGLIN3 $IC_{50}$ µM | VEGF $EC_{50}$ µM | EPO response |
|---|---|---|---|---|
| {[5-(3-chloro-phenyl)-3-hydroxy-pyridine-2-carbonyl]-amino}-acetic acid methyl ester | 2.8 | 21.4 | 9.9 (39) | yes |

TABLE XV-continued

| Compound | EGLIN1 IC$_{50}$ μM | EGLIN3 IC$_{50}$ μM | VEGF EC$_{50}$ μM | EPO response |
|---|---|---|---|---|
| 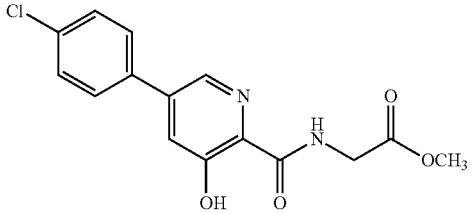 {[5-(4-Chloro-phenyl)-3-hydroxy-pyridine-2-carbonyl]-amino}-acetic acid methyl ester | 3.7 | — | >100 | ND* |
| 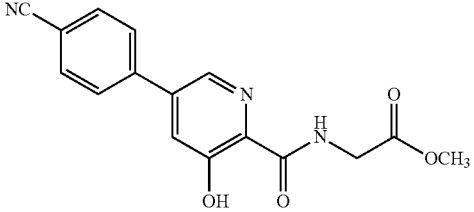 {[5-(4-Cyano-phenyl)-3-hydroxy-pyridine-2-carbonyl]-amino}-acetic acid methyl ester | 5.8 | — | >100 | ND |
| 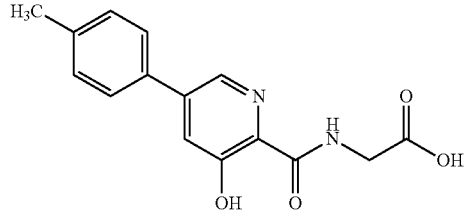 [(3-Hydroxy-5-(4-methylphenyl)pyridine-2-carbonyl)-amino]-acetic acid | 0.65 | 0.18 | 42.1 | yes |
| 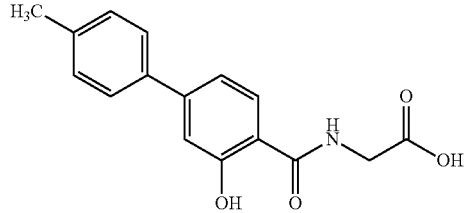 [(3-Hydroxy-4′-methyl-biphenyl-4-carbonyl)-amino]-acetic acid | 20 | — | >100 | yes |
| 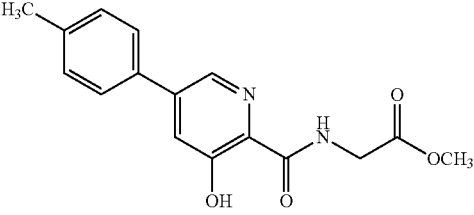 [(3-Hydroxy-5-(4-methylphenyl)-pyridine-2-carbonyl)-amino]-acetic acid methyl ester | 4.1 | 52.3 | 8.2 | ND |

TABLE XV-continued

| Compound | EGLIN1 IC$_{50}$ μM | EGLIN3 IC$_{50}$ μM | VEGF EC$_{50}$ μM | EPO response |
|---|---|---|---|---|
| 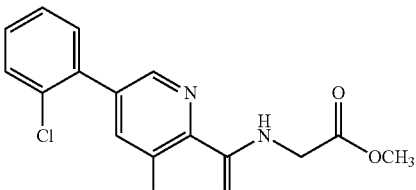 {[5-(2-Chloro-phenyl)-3-hydroxy-pyridine-2-carbonyl]-amino}-acetic acid methyl ester | 6.8 | 37.5 | 7.7 | yes |
| 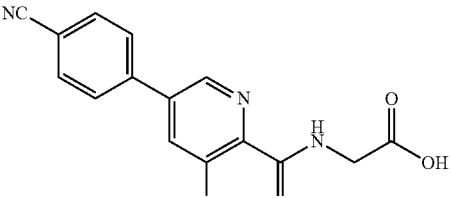 {[5-(4-Cyanophenyl)-3-hydroxypyridine-2-carbonyl]-amino}-acetic acid | 0099 | 0.56 | 4.3 | yes |
| 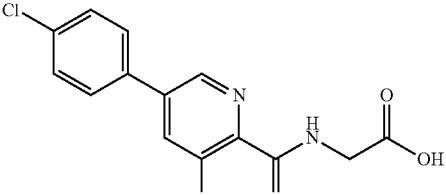 {[5-(4-Chlorophenyl)-3-hydroxypyridine-2-carbonyl]amino}-acetic acid | 0.24 | 0.083 | — | yes |
| 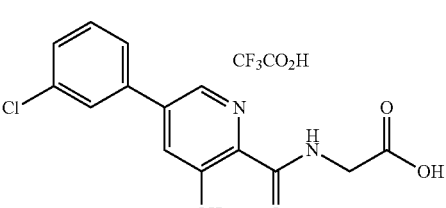 {[5-(3-Chlorophenyl)-3-hydroxypyridine-2-carbonyl]amino}-acetic acid trifluoroacetic acid salt | 0.41 | — | 7.6 | ND |
| 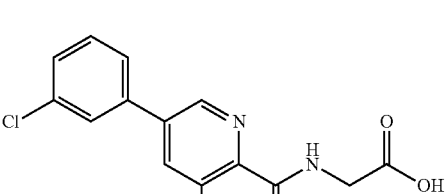 {[5-(3-Chlorophenyl)-3-hydroxypyridine-2-carbonyl]amino}-acetic acid | 1.1 | 0.39 | — | yes |

TABLE XV-continued

| Compound | EGLIN1 IC$_{50}$ μM | EGLIN3 IC$_{50}$ μM | VEGF EC$_{50}$ μM | EPO response |
|---|---|---|---|---|
| 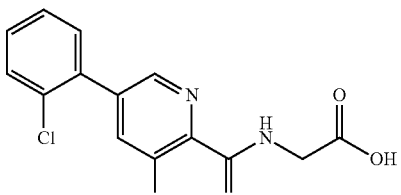<br>{[5-(2-Chlorophenyl)-3-hydroxypyridine-2-carbonyl]amino}-acetic acid | 1.1 | 0.39 | — | yes |
| 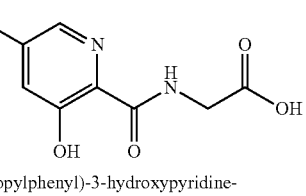<br>{[5-(4-Isopropylphenyl)-3-hydroxypyridine-2-carbonyl]amino}-acetic acid | 0.44 | — | 15 | — |
| 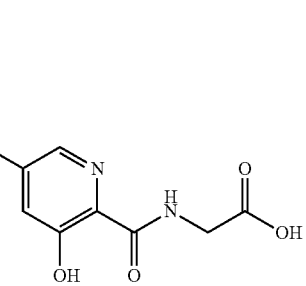<br>{[5-(4-Chlorophenyl)-3-hydroxypyridine-2-carbonyl]amino}-acetic acid | 0.3 | — | >100 | — |
| 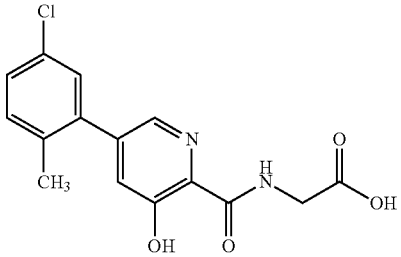<br>{[5-(4-Isopropoxyphenyl)-3-hydroxypyridine-2-carbonyl]amino}-acetic acid | 1.6 | — | >100 | — |
| <br>{[5-(2-Methyl-5-chlorophenyl)-3-hydroxypyridine-2-carbonyl]amino}-acetic acid | 2.5 | — | 3.3 | — |

TABLE XV-continued

| Compound | EGLIN1 IC$_{50}$ μM | EGLIN3 IC$_{50}$ μM | VEGF EC$_{50}$ μM | EPO response |
|---|---|---|---|---|
| 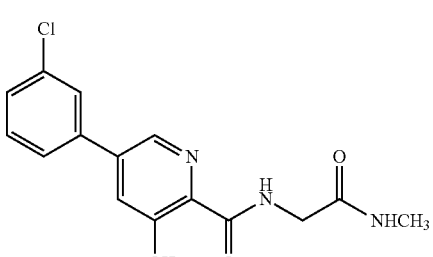<br>5-(3-Chlorophenyl)-N-(2-methylamino-2-oxoethyl)-3-hydroxypyridin-2-yl amide | 1.2 | 1.3 | 1.4 | yes |
| 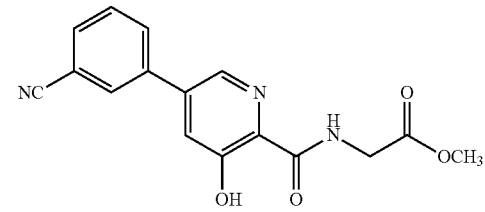<br>{[5-(3-Cyano-phenyl)-3-hydroxy-pyridine-2-carbonyl]-amino}-acetic acid methyl ester | 5.1 | — | >100 | ND |
| 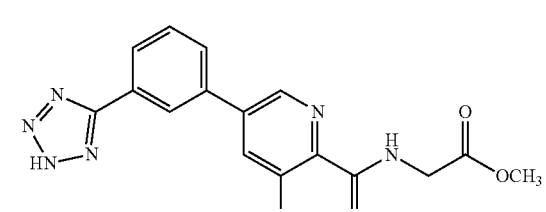<br>({3-Hydroxy-5-[3-(2H-tetrazol-5-yl)-phenyl]-pyridine-2-carbonyl}-amino)-acetic acid methyl ester | 2.6 | — | >100 | ND |
| 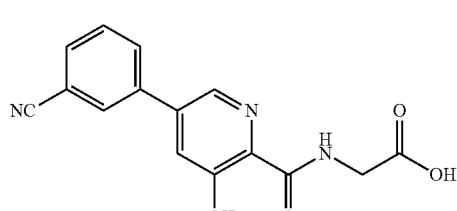<br>{[5-(3-Cyanophenyl)-3-hydroxypyridine-2-carbonyl]amino}-acetic acid | 0.19 | — | >100 | ND |

TABLE XV-continued

| Compound | EGLIN1 IC$_{50}$ μM | EGLIN3 IC$_{50}$ μM | VEGF EC$_{50}$ μM | EPO response |
|---|---|---|---|---|
| {[5-(3-Carbamoyl-phenyl)-3-hydroxypyridine-2-carbonyl]-amino}-acetic acide methyl ester | 11.2 | — | 50.1 | ND |
| ({3-Hydroxy-5-[3-(pyrrolidine-1-carbonyl)-phenyl]-pyridine-2-carbonyl}-amino)-acetic acid methyl ester | 2.5 | — | >100 | ND |
| ({3-Hydroxy-5-[3-(pyrrolidine-1-carbonyl)-phenyl]-pyridine-2-carbonyl}amino)-acetic acid | 0.3 | — | >100 | ND |
| ({3-Hydroxy-5-[3-(2H-tetrazol-5-yl)-phenyl]-pyridine-2-carbonyl}-amino)-acetic acid | 0.4 | — | >100 | ND |
| ({5-[3-(Cyclopropanecarbonyl-amino)-phenyl]-3-hydroxy-pyridine-2-carbonyl}-amino)-acetic acid methyl ester | 9.2 | — | — | ND |

*ND = not determined.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

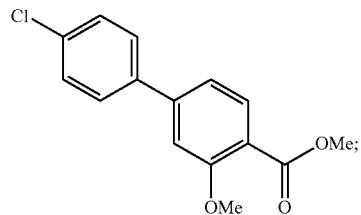

What is claimed is:

1. A process for preparing a compound having the formula:

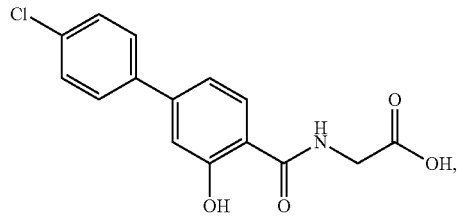 [SMILES: O=C(O)CNC(=O)c1ccc(-c2ccc(Cl)cc2)cc1O]

comprising:

(a) reacting a 4-chlorophenyl boronic acid:

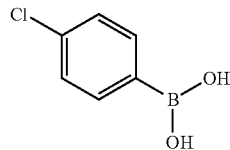

with methyl 4-bromo-2-methoxybenzoate:

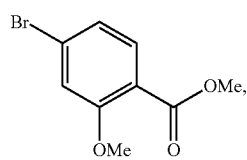

in the presence of a catalyst to form 4'-chloro-3-methoxy-biphenyl-4-carboxylic acid methyl ester:

(b) reacting 4'-chloro-3-methoxy-biphenyl-4-carboxylic acid methyl ester obtained from step (a) with lithium hydroxide to form 4'-chloro-3-methoxy-biphenyl-4-carboxylic acid:

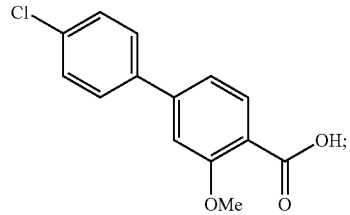 [SMILES: COc1cc(-c2ccc(Cl)cc2)ccc1C(=O)O]

and (c) reacting 4'-chloro-3-methoxy-biphenyl-4-carboxylic acid obtained from step (b) with glycine ethyl ester, in the presence of coupling agents to form [(4'-chloro-3-methoxy-biphenyl-4-carbonyl)-amino]-acetic acid ethyl ester:

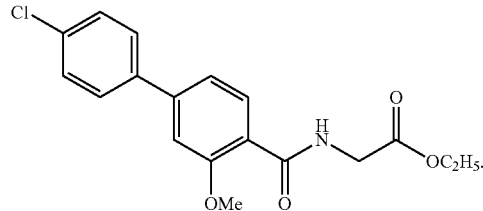 [SMILES: CCOC(=O)CNC(=O)c1ccc(-c2ccc(Cl)cc2)cc1OC]

2. The process of claim 1, further comprising reacting [(4'-chloro-3-methoxy-biphenyl-4-carbonyl)-amino]-acetic acid ethyl ester:

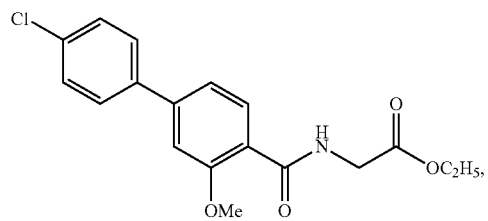 [SMILES: CCOC(=O)CNC(=O)c1ccc(-c2ccc(Cl)cc2)cc1OC]

with BBr₃ to form [(4'-Chloro-3-hydroxy-biphenyl-4-carbonyl)-amino]-acetic acid:

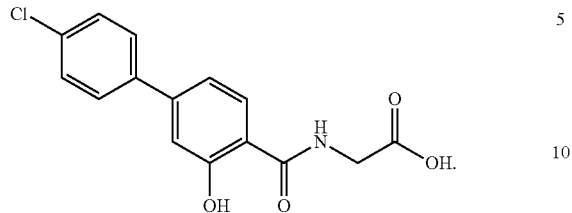

3. The process of claim 1, wherein the catalyst in step (a) is [1,1'-bis (diphenylphosphino)ferrocine]dichloro palladium(II).

4. The process of claim 1, wherein the reaction in step (a) is conducted in the presence of a base that is K₃PO₄.

5. The process of claim 1, wherein the coupling reagents in step (c) are 1-(3-dimethylaminopropyl)-3-ethylcarbodiimide (EDCl) and 1-hydroxybenzotriazole (HOBt).

* * * * *

UNITED STATES PATENT AND TRADEMARK OFFICE
CERTIFICATE OF CORRECTION

PATENT NO. : 11,883,386 B2
APPLICATION NO. : 17/815391
DATED : January 30, 2024
INVENTOR(S) : Richard Masaru Kawamoto et al.

Page 1 of 1

It is certified that error appears in the above-identified patent and that said Letters Patent is hereby corrected as shown below:

In the Specification

Column 77, beneath third compound structure:
Delete "{[5-(4-Chlorophenyl)-3-hydroxypyridine-2-carbonyl]amino}-acetic acid"
Replace with – {[5-(4-Fluorophenyl)-3-hydroxypyridine-2-carbonyl]amino}-acetic acid –

Signed and Sealed this
Sixth Day of May, 2025

Coke Morgan Stewart
*Acting Director of the United States Patent and Trademark Office*